(12) United States Patent
Shapiro et al.

(10) Patent No.: US 10,397,751 B2
(45) Date of Patent: *Aug. 27, 2019

(54) GEOLOCATION BRACELET, SYSTEM, AND METHODS

(71) Applicant: Fynd Technologies, Inc., Hollywood, FL (US)

(72) Inventors: Ryan J. Shapiro, Bay Harbors Island, FL (US); Thomas Harrah, Parkland, FL (US)

(73) Assignee: FYND TECHNOLOGIES, INC., Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/913,817

(22) Filed: Mar. 6, 2018

(65) Prior Publication Data

US 2019/0208363 A1 Jul. 4, 2019

Related U.S. Application Data

(63) Continuation of application No. 15/693,394, filed on Aug. 31, 2017, now Pat. No. 10,157,528, which is a
(Continued)

(51) Int. Cl.
*G08B 1/08* (2006.01)
*H04W 4/029* (2018.01)
(Continued)

(52) U.S. Cl.
CPC ............. *H04W 4/029* (2018.02); *A61B 5/681* (2013.01); *G16H 50/30* (2018.01); *H04M 7/006* (2013.01)

(58) Field of Classification Search
CPC ....... H04W 4/029; A61B 5/681; G16H 50/00; G08B 1/08
See application file for complete search history.

(56) References Cited

U.S. PATENT DOCUMENTS

2002/0024443 A1* 2/2002 Hawkins ................ G08B 21/22
340/573.1
2008/0001735 A1* 1/2008 Tran .................... G06F 19/3418
340/539.22
(Continued)

*Primary Examiner* — Phung Nguyen
(74) *Attorney, Agent, or Firm* — James S. Nolan

(57) ABSTRACT

An identity, position, health, tracking and/or monitoring apparatus is provided. The identity, position, health, tracking and/or monitoring apparatus includes a housing configured to removably secure the tracking or monitoring apparatus to a person, such as a child, pet, etc. or an object. Particularly, the tracking and/or monitoring apparatus may be connectable to a flexible and/or stretchable band that may be worn around a part of the body, such as a wrist, necklace, waist, or ankle of a user. The tracking and/or monitoring apparatus may include one or more of a processing unit, a geolocating module, a communications module, an artificial intelligence module, and/or a music playing module. In various embodiments, the tracking and/or monitoring apparatus is configured for locating, tracking, and/or monitoring a user of the device as well as an associated biological or environmental condition of the user. In particular instances, the tracking and/or monitoring apparatus is configured for performing cellular or VOIP communications.

20 Claims, 16 Drawing Sheets

Related U.S. Application Data continuation of application No. 15/451,368, filed on Mar. 6, 2017, now Pat. No. 9,940,808.

(60) Provisional application No. 62/613,014, filed on Jan. 2, 2018, provisional application No. 62/084,433, filed on Nov. 25, 2014, provisional application No. 62/467,789, filed on Mar. 6, 2017.

(51) Int. Cl.
  *H04M 7/00* (2006.01)
  *A61B 5/00* (2006.01)
  *G16H 50/30* (2018.01)

(56) References Cited

U.S. PATENT DOCUMENTS

| | | | | |
|---|---|---|---|---|
| 2012/0015778 | A1* | 1/2012 | Lee | A63B 71/0622 482/8 |
| 2013/0278631 | A1* | 10/2013 | Border | G02B 27/017 345/633 |

* cited by examiner

GEOLOCATION BRACELET, SYSTEM, AND METHODS

CROSS REFERENCE TO RELATED APPLICATIONS

The present application claims priority to and the benefit of U.S. provisional patent application No. 62/467,789, filed Mar. 6, 2017, and 62/613,014, filed Jan. 2, 2018. The present application is also a continuation-in-part application of U.S. non-provisional patent application Ser. No. 15/451,368, filed Mar. 6, 2017, entitled GEOLOCATION BRACELET, SYSTEM, AND METHODS, now U.S. Pat. No. 9,940,808, issued Apr. 10, 2018, and Ser. No. 15/693,394, filed Aug. 31, 2017, entitled GEOLOCATION BRACELET, SYSTEM, AND METHODS, now U.S. Pat. No. 10,157,528, issued Dec. 18, 2018, which are continuing applications of U.S. non-provisional patent application Ser. No. 14/950,352, filed Nov. 24, 2015, entitled, "GEOLOCATION BRACELET, SYSTEM, AND METHODS", now U.S. Pat. No. 9,654,917, issued May 16, 2017, which claims priority to and the benefit of U.S. provisional patent application No. 62/084,433, filed Nov. 24, 2014. The contents and disclosures of each of the aforementioned applications are hereby incorporated by reference in their entirety herein for any and all purposes.

FIELD OF THE DISCLOSURE

An identity, geolocation (e.g., position), and/or health status monitoring and/or tracking apparatus that has a thin profile, is low cost, and is curved.

BACKGROUND TO THE DISCLOSURE

The monitoring of children is an important aspect of keeping them safe. Parents of newborns often monitor their infants while sleeping by means of an electronic monitoring system. This system typically includes a pair of radio units often including one or more of a transmitter and/or a receiver. The first radio unit includes a transmitter that is placed in the room of the sleeping newborn so as to listen to the infant's sleeping and breathing. If, in any given instance, the child starts crying or evidences a problem in breathing, the transmitter can pick up the sounds of the child and transmit them to its companion unit containing a receiver, whereby upon receipt of the radio transmission of the sounds, the parent or other monitoring person, can be alerted to come and check on the child.

In other instances, the parents of a child may monitor that child and/or the child's caretaker by placing a video monitoring device in the room of the child, which monitoring device may be configured to keep a video record of the child within the room and/or transmit the same, such as over an internal WIFI network, such as to an auxiliary receiving unit, so as to allow the parent to monitor the child within the room. In further instances, the parent may keep track of the child by tracking the child's possession of a mobile telephonic device. For instance, in various instances, a mobile device, such as in the possession of a child, may be triangulated by the respective cell towers it comes into range with, and the position of the cell phone can be transmitted, such as over the cellular network, to a third party monitor, such as a parent.

However, although there are many benefits in using various of the devices set forth above, such as for the monitoring, tracking, and/or protecting of children, each of these devices have drawbacks. For instance, while baby monitors are useful for monitoring an infant while it is sleeping, and video cameras may be useful for monitoring the room of a child, they are limited in usefulness in that they are limited to monitoring sounds and images and not tracking movement of the child, such as while outside of the home. The mobile monitoring system provided by various tracking software installed on a person's mobile telephone is useful in tracking the movement of the respective phone. However, although useful, such a monitoring and tracking system also suffers from some drawbacks in that such monitoring systems rely on the mobile device being tracked and are, therefore, dependent on the battery life of the phones. Since, phones are used for several different purposes, besides tracking and monitoring the whereabouts of the phone, this battery life does not last long, making the use of the phone as a tracking device less than ideal. Additionally, mobile phones are typically big, and include a relatively large touch screen for viewing messages and videos.

What is needed therefore is a device, system, and method of using the same that is configured for identifying, locating, tracking and/or monitoring one or more conditions of a user. It would additionally be beneficial if such a device were also inexpensive, easy to manufacture, mobile, and had a long lasting battery life. The devices, systems, and methods of their use as described herein meet these and other such needs.

SUMMARY OF THE DISCLOSURE

In one aspect, provided herein is a thin profile personal tracking device, such as a geolocation device, for locating a person, pet, and/or object within a geographical region that is easy to use and simple to manufacture. In various instances, the device may be configured to function as an identity, position, and/or health status tracking and/or monitoring apparatus. The personal tracking and geolocation, identity, position, and/or health monitoring devices and systems provided herein may be configured as a small, curved, and/or articulated chip, e.g., microchip, that is attachable or otherwise capable of being mounted to a substrate, for easy transport, and/or may be configured to be coupled with or otherwise made part of a secondary article, such as a bracelet or pendant, so as to be capable of being worn. In various instances, the microchip has a thin profile, is lightweight, uses low energy, and may be curved or articulated, such as for ease of use, such as within the bounds of a curved piece of jewelry, such as a bracelet, for instance, a sports band, watch, or pendant. For example, in one particular implementation, the geolocation device may be a chip, which chip may include one or more processors, e.g., micro- or nano-processors, that is capable of being coupled to or otherwise carried within a band, such as a sports band or may be configured as a pendant that may be coupled to a necklace or collar or carabineer coupling device, and may be used to track the whereabouts of the wearer, which may be especially useful where the wearer is a child or pet, such as a child or pet prone to wandering off or in an environment that renders the child or pet susceptible to abduction. The tracking device may also be used to track and/or monitor an object Accordingly, in one aspect, a substrate having electronic circuitry printed thereon is provided. For instance, in various implementations the substrate may be a circuit board and the electronic circuitry may be configured to function as a central processing unit (CPU) or a Graphics Processing Unit (GPU). For example, in particular embodiments, the printed substrate may include one or more microchips having one or more CPUs or GPUs thereon, such as a CPU or GPU that is capable of performing various processing functions. In various embodiments, the printed circuit board (PCB) may be made of a rigid, semi-rigid, semi-flexible, flexible and/or articulated material, or a combination of the same.

Particularly, in certain instances, the substrate may have an elongated body that is defined by a proximal portion, which includes a proximal end, a distal portion, which includes a distal end, and a medial portion separating the proximal portion from the distal portion. In such an instance, the proximal, medial, and distal portions may be circumscribed by a circumferential portion. In other instances, the elongated body may simply be defined by the circumferential portion that bounds the first surface and the second surface of the elongated body. In such an instance, the elongated body may not need or include a first and/or second end portions, e.g., proximal and/or distal ends. In some instances, the first and second surfaces may be opposed to one another and form a waterproof encasing cavity therewith, the elongated body being sized and configured to be worn around a limb of a human, such as the wrist or ankle of a child. In various implementations, the circuit board may be curved and/or may be composed of several segments, and/or may be articulated.

Accordingly, in certain instances, the PCB may be a combination of rigid and flexible materials so as to allow the components to be securely mounted on the rigid sections, while allowing the flexible sections to flex so that the overall board may be able to bend, and/or otherwise twist, stretch, articulate, or to curve such as to bend and/or conform to the wrists of a wearer of the band, such as a small child. Particularly, the substrate may be composed of one or more layers, such as conductive layers, e.g., of metal portions such as copper, that have been layered on top of an insulating layer, such as an insulating layer made of a glass epoxy. In addition to including electronic circuitry, the printed substrate, e.g., a microchip having a microprocessor thereon, may additionally include or otherwise be operationally coupled with one or more other modules, such as a memory, a communications module, an input/output module, and an energy source, such as a low energy power source and/or battery. In certain embodiments, the microchip may include an onboard memory and/or communications module, and may be operably coupled to one or more sensors and/or one or more displays. In particular embodiments, as described herein below, the microchip may be a plurality of microchips, such as in a serial and/or a stacked configuration.

For instance, in various instances, a substrate is provided wherein the substrate may be a circuit board or otherwise include one or more of a microprocessor(s), a memory, a communications module, and an energy source, such as a low energy power source, e.g., a battery, powering the same, such as where one or more processors are provided in a serial and/or stacked configuration. In certain instances, the substrate may include an input/output module, a sensing mechanism, and/or may be coupled to a display. In particular embodiments, the microchip(s) may be any suitable processing unit, such as an Intel® or Arm® core processing unit. The memory may be any suitable memory such as a RAM, ROM, NAND flash or FRAM. The communications module may include one or both of a suitable transmitter and/or a suitable receiver.

For example, a typical transmitter may be a radio frequency (RF) transmitter, a cellular transmitter, WIFI, and/or a Bluetooth®, such as a low energy Bluetooth® transmitter unit. In some instances, a typical receiver may include a satellite based geolocation system or other mechanism for determining the position of an object in three-dimensional space. For instance, the geolocation system may include one or more technologies such as a Global Navigation Satellite System (GNSS). Exemplary GNSS systems that enable accurate geolocation can include GPS in the United States, Globalnaya navigatsionnaya sputnikovaya sistema (GLONASS) in Russia, Galileo in the European Union, and/or BeiDou System (BDS) in China.

The energy source may be any suitable source of energy such as a battery, such as Lithium Cadmium or Zink Manganese battery or wireless charging, solar, thermal, or motion re-chargeable battery. For instance, in various instances, the device, e.g., bracelet, may include a battery, which battery may be configured for being wirelessly charged. Particularly, the bracelet may be configured for being charged via induction and/or in accordance with a wireless charging standard, such as A4WP, Qi, and the like. For example, the bracelet may include a wireless power receiver that is adapted for receiving a charge over a distance from a power transmitter. In such an instance, the transmitter and receiver may include magnetic coils and/or antennas that are tuned together so as to transmit and receive an electrical and/or magnetic field that induces a current that may be used to charge an associated battery.

In various instances, the preservation of battery life is an important goal to be achieved by the devices and systems presented herein. Accordingly, in particular instances, the system components and/or methods of the disclosure may be configured so as to restrict certain, e.g., non-essential, functions, as determined by the user or the system itself, such as in response to a declining or critical battery charge, time of day/night, day of the week, location, or the like. Such non-essential functions may be those functions directed to entertainment, displaying information, conducting non essential communications, and the like, while essential functions may be as locating, tracking, monitoring, and contacting guardians will still work for a prolonged period of time. In particular embodiments, the user or the system itself may control the functionality of the various features of the device, or they may be determined by pre-determined settings, allowing the turning on or off of the features, and in some instances, may be determined by battery level and/or one or more predicted conditions. For instance, the settings may be configured for turning off entertainment features, e.g., restricting access thereto, during school hours, and turning them on, e.g., allowing access thereto, after school hours, at night, on the weekend, or while at home, and the like. Likewise, the system may be configured such that when the battery life is greater than a certain percentage all functionality is on and/or accessible, but when it falls below a certain percentage, certain determined non-essential functions are powered down or turned off, such as when the battery level falls below a certain level, such as below 50%, below 40%, below 30%, below 25%, below 20%, below 15%, below 10%, below 5%, below 3%, and the like. In particular implementations, the turning off of functionality may be staggered such that as certain conditions, e.g., battery level, are reached, particular functionality is turned off, some sooner than others. In some instances, this may be determined by the system, such as by a suitably configured A/I module of the system.

In order to prolong battery life and/or to increase rapidity of charging, in certain instances, the device may be configured for being coupled to a power transmitter that is adapted for wireless charging, such as for inductive charging. For instance, the device may be configured for receiving a voltage and converting the received voltage into a high frequency alternating current that may be transmitted via a suitably configured transmitter circuit that is coupled to the transmitter coil. Such alternating current flowing through the transmitter coil generates a magnetic field that is received by the receiver coil of the wearable device, thereby generating a corresponding current within the receiver coil that may then be converted into direct current via a suitable transformer and stored as energy within the battery, thereby recharging the battery of the device, such as wirelessly. In various instances, the coils may be configured to resonate and/or oscillate in response to one another, e.g., at the same or similar frequency, such as through magnetic resonance whereby wireless charging over longer distances may be achieved.

In particular instances the circuit board containing the microprocessor(s), which may be configured so as to be worn by a user, such as by a child whose location is to be monitored and/or tracked, may include and/or may otherwise be coupled to an input/output module, one or more displays, and/or one or more sensors. Input, such as input from a user, or a person associated with the user, may be received in any form, including, but not limited to, acoustic, speech, or tactile input. Accordingly, a typical input device may include, but is not limited to, keyboards, touch screens or other touch-sensitive devices such as single or multi-point resistive or capacitive trackpads, voice recognition hardware and software, optical scanners, optical pointers, digital image capture devices and associated interpretation software, a Universal Serial Bus (USB) port, Secure Digital Input Output (SD/SDIO) port, flash drive port, lightning port, and the like. A typical output device may be a display such as a capacitive sensing control panel display. In various instances, the display may be the typical display of a mobile computing device, such as the display of a mobile phone and/or tablet computer, and the like.

A typical sensor may be any form of data collection mechanism capable of detecting a relevant characteristic and configured for transmitting that data to the microprocessor for processing and/or transmission and/or display such as to the user or other third party, for instance, a parent, guardian, or medical personnel charged with taking care of the wearer of the circuit board. For instance, in certain instances, the sensor may be a motion and/or orientation sensor, such as a distance measuring sensor, such as a pedometer, a speed or velocity sensor, including an accelerometer, for example, a multi-axis accelerometer, a gyroscope, strain gauges, and/or a piezoelectric sensor, optical sensor, energy sensor, a thermometer, compass, and the like. In various instances, the sensor may be configured so as to be a physiological data collector that may be configured to collect physiological data, such as data associated with a person, e.g., child or adult, and/or his or her state of health and/or performance in an activity, such as an activity requiring mental or physical exertion. For example, the sensor may be a physiologic sensor and/or data collector, such as a temperature gauge or body or environmental thermometer, so as to measure the temperature of the user and/or his environment; a heart rate monitor or pulse meter, so as to measure the heart rate of the user; a blood pressure monitor, to measure the users blood pressure; a blood glucose monitor, to measure blood glucose of the user; a myoelectric sensor; a carbon dioxide ($CO_2$) sensor; a breathing rate monitor; a pulse oximeter; oxygen saturation monitors; hemoglobin sensors; an electrocardiogram; an electroencephalography monitor; and/or a pressure monitor; and the like.

In various instances, one or more thermal sensors may be included. For instance, a thermal sensor may include a thermocouple, an infra-red (IR) thermal sensor, and/or other temperature sensing technology. Additionally, in various embodiments, sensors capable of determining one or more characteristics regarding the physical environment may be included, for example, sensors that detect changes in the immediate environment may include temperature sensors, altimeters, wind sensors, humidity sensors, and the like. In various instances, this environmental data can be integrated with one or more of the above referenced physiological data for a determination as to where geographically the sensor is and/or what the condition is of the user of the sensor. In various instances, the information captured, compiled, and/or processed by the one or more sensors set forth above may be communicated to the user, such as in a visual, auditory, or tactile manner, such as via a display, a graphic, a light, e.g., an LED light, light sequence, or series of light, such as from green to yellow to red and infra-red, a sounded alarm or bell, or a vibration, and the like.

These signals may also be arranged to increase or decrease in intensity and/or frequency dependent on the results of the collected and/or compiled data. For example, the amplitude, timing, and duration of an auditory, visual, and/or tactile signal can be varied to indicate to a user or a monitor of the user the nature of the changed input. Particularly, a monitoring and/or tracking device of the disclosure can indicate, e.g., vibrate, in response to a data signal from a sensor, relay, beacon, or other device of the system when a user enters or leaves a certain range of a target distance, target location, target time, physiologic characteristic (e.g., heart rate for a specified time period, breath rate, or number of footfalls, etc.), and the like, or combination thereof. Hence, the tracking device, as well as the location and/or status monitoring device can be configured to vibrate to alert the monitoring entity that the tracking device is going and/or has gone out of range from the target distance, target location, target time, physiologic characteristic (e.g., heart rate for a specified time period, breath rate, or number of footfalls, etc.), and the like, or combination thereof.

Accordingly, in one aspect, a wearable thin profile waterproof geolocation device such as for locating an object, e.g., a child, within a geographical region. In such instances, the geolocation device may include a substrate having an elongated body that is defined by a circumferential portion. The circumferential portion may have two ends, e.g., a first proximal end and a second distal end, which are configured for being joined together, or the circumferential portion may be of a single molded piece having a first surface and a second surface that have been coupled together, e.g., by molding. Hence, in particular instances, the substrate may include a circumferential portion that bounds a first surface and a second surface of the elongated body, such as where the first surface is opposite the second surface and forms a cavity therewith, e.g., a waterproof cavity. In some instances, the elongated body may be sized and configured to be worn around a limb of a human, such as an arm, ankle, or neck of a child.

The substrate may be configured to house a semi-flexible digital logic circuit board arrangement, which may be contained within the cavity of the elongated body of the substrate. In such an instance, the semi-flexible digital logic circuit board arrangement may include a plurality of rigid circuit board portions connected by one or more flexible portions, such as where the digital logic circuit board arrangement is positioned between the first and second surfaces of the elongated body of the substrate. In particular instances, one or more of the rigid circuit board portions of the digital logic circuit board arrangement may include one or more of a central processing unit (CPU) and/or graphics processing unit (GPU), a communications module, a memory, and a battery, such as where the CPU and/or GPU is operably connected to one or both the memory and the battery.

In some instances, the digital logic circuit board arrangement may further include a pairing device such as for pairing the geolocation and tracking device with a remote master device, e.g., via a wireless communication channel. In such an instance, the pairing may be defined by a distance between the geolocation device and the master device such that if the distance between the geolocation device and the master device exceeds a predetermined range, an alarm is set off in one or more of the geolocation device and the master device.

In another aspect, a system for determining and/or displaying information about a user, his or her position and/or location, and/or a state of his or her condition of health is provided. In certain instances, the system may also be configured for transmitting the data to a third party, such as a third party interested in identifying, monitoring, and/or tracking the user and/or the user's activities and/or health. For instance, in various embodiments, the system may include one or more of a geolocation device, such as that described above, a network, a data processing unit, one or more external sensors, e.g., a beacon or relay, and/or a receiver, such as a computing device, e.g., a mobile computing device and/or other viewing system.

For example, the system may provide a geolocation and/or tracking device, such as that described above, which geolocation device may include one or more of a microprocessor(s), a memory, a communications module, an input/output port, and/or a sensor(s). In such an instance, the geolocation device may be contained within a housing, such as within the bounds of a bracelet, necklace, pendant, ring, keychain, any other wearable device, or the like, which may be worn, such as by a child, adult, or animal or object the tracking or monitoring of which may be desired, such as by a parent wanting to ensure the safety of the child. In particular, the geolocation and/or monitoring device may function in part to display the identity of the user and/or a condition of the users health. As indicated, in various instances, the device may contain a communications module that not only includes a receiver, such as via triangulation of satellite data, such as a GPS receiver, such as for determining the location of the device, e.g., providing location data, but also includes a transmitter, such as for transmitting such position and other data to the receiving device.

Consequently, the system may be configured to track and/or monitor the user and/or the condition of the user. Hence, in such instances the system may include a receiver, such as a computing device that is suitably configured for receiving a transmission, for instance, a signal, such as a digital or analog signal, from the transmitter of the geolocation device. Additionally, the system may include a network, such as a cellular, WIFI, or other network interface that is configured for effectuating the transfer of data from the transmitter of the geolocation device to the receiver of the computing device. In various instances the system may include a data processing system, for processing the data prior to or after transmission. Further, in some instances, the system may include a viewing system, such as a display screen, for instance, a liquid crystal display (LCD), light emitting diode (LED) display, plasma display, or the like.

In another aspect, a method for monitoring and/or tracking a person or an object is provided. The method may include one or more of providing a geolocating device, such as that set forth above, attaching the geolocating device to a person, pet, or an object to be monitored and/or tracked, and employing a receiver to monitor and/or track the person, pet, or object, such as over a network joining the two. More particularly, the method may include providing the geolocating device and employing the system described above to monitor and/or track the person, pet, or object. In various instances, the system may include a relay, such as a beacon, that is configured to receive a signal from the geolocating device so as to thereby determine the location of the device, and further transferring that information, such as via the Internet, cellular, or other network, to the receiver so as to thereby allow a third party to monitor the position and other data collected by the device.

In a further aspect, a method for tracking an object, e.g., a child or pet, such as on a continuous or on an as needed only basis is provided. For instance, an application, e.g., an "app", may be provided such as where the "app" is configured to initiate an as needed or continuous basis tracking procedure, such as in response to an activating event, such as from a master device that is paired with a bracelet, pendant, or other wearable configured as described herein for geolocation. Particularly, in one embodiment, the master device and the geolocation device may be paired, such as via the app, such as where an adult supervisor, e.g., a parent, has a mobile computing device, e.g., the master device, running a suitably configured app, and a child is wearing a suitably configured geolocation bracelet or band, which wearable itself is also running the app. In such an instance, the app may be configured so as to provide a tracking and/or monitoring function such that when the parent or guardian or pet owner activates the app, the wearable running the corresponding app is itself activated and in response thereto sends the location of the wearable, e.g., the child rearing a bracelet, thereby allowing the parent to verify and/or locate where the child or pet is within a geographic region.

More particular, through the tracking and/or monitoring application, the user, e.g., "User 1" may initiate an active tracking and/or monitoring procedure that enables the tracking function, e.g., the tracker and/or monitoring, to begin sending continuous or intermittent updates (e.g., about once per second), which updates may give pertinent information on the position, speed, activity, health, or other characteristic of the wearable and/or wearer thereof. For example, in particular embodiments, the app may be presented as a user interface on a mobile or home computing device. The user interface may be a simple "push and hold" tracking and/or monitoring or just one-time "push" tracking button, or representation thereof. The pushing or otherwise activating of the button correspondingly activates the tracking, monitoring, and/or updating functionality, thereby allowing User 1, e.g., Master User, to track User 2, e.g., Servant User, such as at that particular moment and/or over a given period of time. Such a feature as this enables accurate tracking and/or monitoring when needed, without using battery or other resources when not needed.

In an additional aspect, the devices of the system, such as a paired master and/or servant device, may be configured for limited time sharing of a characteristic, e.g., location, health status, of one device or wearer thereof vis a vis the other, such as by both devices running a suitably configured "app". For instance, the geolocation bracelet, e.g., being worn by User 2, can share its location, e.g., at the push of a suitably configured button or a representation thereof, to User 1, such as by transmitting a web link from User 2 to User 1. In such an instance, the app may be configured so as to be accessible via a mobile or stationary computer, such as by the sending of and clicking on the link and/or otherwise accessing a web-based portal. The link can be sent via email, text, SMS, or other suitably configured social media interface, such as FACEBOOK®, TWITTER®, INSTAGRAM®, WHATSAPP®, and the like.

Accordingly, both the master and servant paired devices may communicate one with the other, such as via sharing one or more links, e.g., via a link to a web portal, such as a website. In such an instance, the devices and/or app may be configured to share and/or show the location (or other characteristic) and/or tracking history and/or current location information of the selected device or its user, such as during the duration of the sharing event, e.g., for a given time period. Once the time period expires, the link will de-activate and the web portal will no longer be accessible and/or updated. For instance, during the sharing period, updates may be sent on a regular and/or periodic basis, which updates may include data, such as location and/or biological or other characteristic data of the user. Hence, during the sharing period the website may be continuously updated and/or may share a link such as an "Update Now" link that may be activated, e.g., clicked on, so as receive a real-time status update so as to allow users to get the most up to date, e.g., location, information. The user can select a time limit for the sharing, such as for minutes, to hours, e.g., 24 hours, to days, weeks, e.g., 1 or 2 weeks, to months, and etc. However, when the sharing period is over the site will now longer share the "Update Now" button and/or will no longer be accessible. This virtual "sharing" feature can be used for many particular use case applications, such as sharing a child's location with a guardian, relative, e.g., grandparents, while the child is staying with them, sharing the location with a neighbor who may be taking the child to an all-day activity, and even for monitoring sporting events such as cross country running or bicycling events.

In a further embodiment, the geolocation device may be configured for sharing and/or receiving messages to and/or from a paired, e.g., master device. Particularly, the devices and/or systems disclosed herein may be configured so as to provide and/or receive secure voice messages, such as between the master and servant paired devices, e.g., via a suitably configured tracking, monitoring, and/or messaging app. More particularly, in such an instance, a master (or servant) device and/or an "app" thereof may be configured so as to record a message, e.g., a short voice message, which may be sent to a predetermined and/or selected geolocation device(s), for instance, as a compressed data file.

Accordingly, the geolocation device may include a sound element, such as a small, micro-speaker from which the message may be played. Hence, once received by the other, e.g., servant, device a user thereof can then press an activator, e.g., a button or representation thereof, to play the message. A signal and/or message may then be sent back to the other, e.g., master, device so as to indicate to the sending device that the message has been played, e.g., the guardian will know that the child has pressed the "button" to play the message. In certain instances, the master, e.g., guardian, device can select a recently sent message and have it played again on the servant device, e.g., bracelet or pendant, so as to have it playable again with or without the button being pressed on the servant device and without sending the compressed file again. Likewise, the servant device may be activated in such a manner that a short message can be recorded and sent to the master device for playing thereon, such as in the form of another compressed data file. In various instances, pre-recorded messages can be activated and/or sent back and forth. In particular instances, one or more, e.g., all, of the messages may be stored in the cloud, and may be made available to for playing, downloading, and/or sharing, or posting, e.g., to social media sites.

In various instances, the paired devices may be configured in such a manner that one device is able to set up one or more reminders on the other device. For example, a master device may be configured so as to setup reminders, events, and/or appointments that are accessible by the servant device, or vice-versa, so as to remind the user of important times. Each reminding and/or scheduling event may be viewable, e.g., via a calendar, or playable as an audio file via a prompt from the device. Various sound effects can also be used to indicate the events. The reminders can be recorded via an audio prompt, or can be pre-recorded messages. Such messages can be any message such as a wakeup or other message plus alarm, e.g., "Time to get up!" or "Time to go to school bus pickup location" or "Time to brush teeth and go to bed!" or a sports/class alarm, etc. These events can be setup and managed using the app or an online database.

Additionally, in particular instances, an aspect of the disclosure is a wearable thin profile geolocation device, such as for tracking and/or monitoring a human or pet or object within a geographical region, and in some instances, may be configured for predicting a location, direction of travel, a status, and/or an environmental condition of a user of the device. In such instances, the device may include a housing having an elongated body, such as an elongated body that has first and a second elongated member, where each of the first and second elongated members are defined by a respective first and second extended surface portion and a circumferential portion. In certain embodiments, the circumferential portion may have a coupling or latching mechanisms, the latching member for allowing the first elongated member and the second elongated member to be coupled together to form the housing. In a particular iteration, the housing may form a waterproof cavity in between the first and second extended surface portions of the first and second elongated members.

Further, the thin profile geolocation device may include, such as within a cavity of the housing, logic board, such as a semi-flexible digital logic circuit board arrangement. In various instances, the semi-flexibile digital logic circuit board arrangement may have one or more rigid circuit board portions that may be connected by one or more flexible portions, where the one or more rigid circuit board portions may include one or more of a central processing unit (CPU) or graphics processing unit (GPU), a geoloacting module, a communications module, a music playing module, an artificial intelligence (A/I) module, a memory, and a battery, which may be operably inter-connected one with the other. In such instances, the A/I module may be configured for receiving a user command regarding the implementation of a function, interpreting the user command regarding the function, and directing the CPU or GPU to perform the commanded function, such as where, for example, the commanded function may pertain to one or more of determining and/or predicting a location, a direction of travel, a health status, an environmental condition, and the like of a person or pet wearing the geolocation device, and/or may pertain to the selecting and/or playing of music, and/or the initiating and conducting of cellular, VOIP, or other communications protocols. Additionally, the communications module may be configured for transmitting and/or receiving sensed, determined, and/or predicted location, direction of travel, health status, music, and/or environmental condition data to or from an associated computing device, which may be coupled, e.g., via a wireless network, to the geolocation device.

DETAILED DESCRIPTION OF THE DISCLOSURE

Figure 1A:
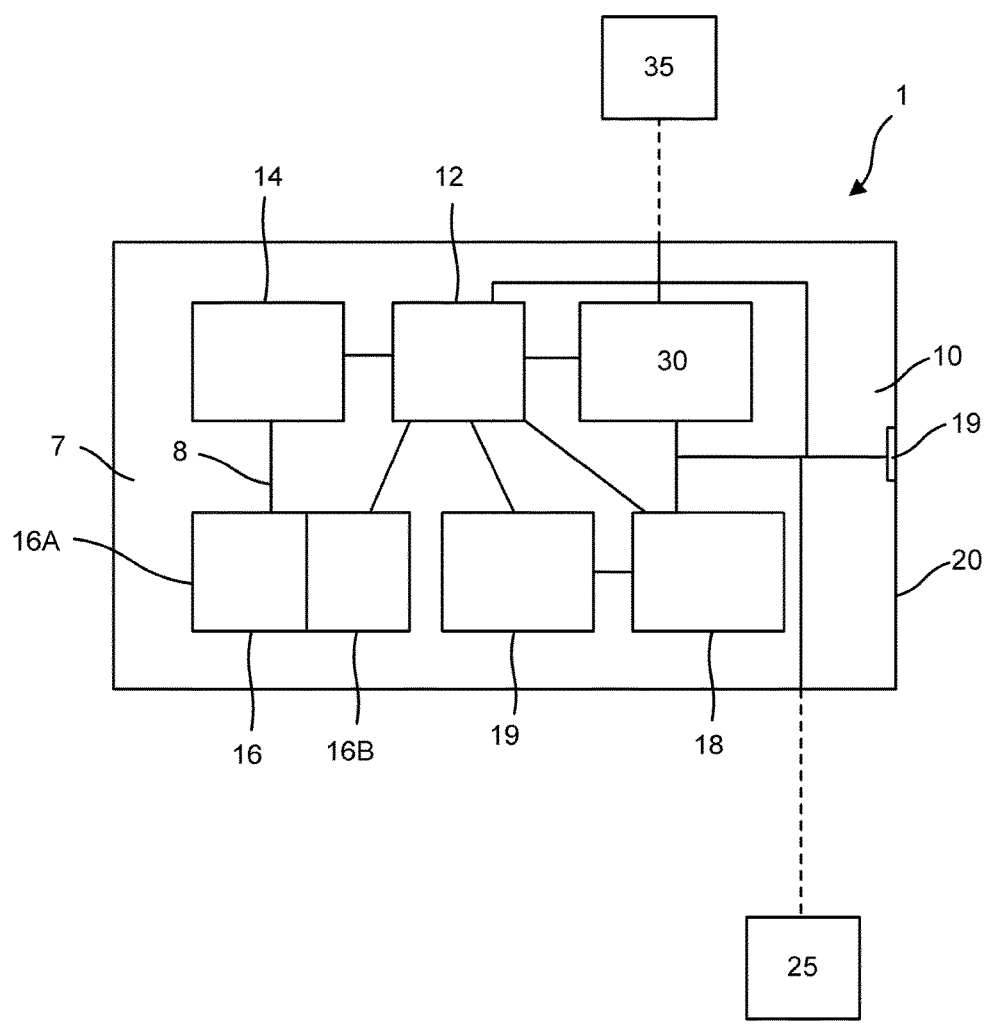
FIG. 1A is a diagram of an exemplary circuit board arrangement of a system including an identity, geolocation, and/or health status monitoring apparatus of the disclosure.

As summarized above, provided herein is a personal tracking and/or monitoring device such as an identity, position, and/or health monitoring apparatus that is simple to use and easy to manufacture. In various embodiments, the identity, position, and/or health monitoring apparatus may be contained within a housing, which housing may include a retention feature, such as wristband, collar, keychain, or the like, configured to removably secure the monitoring apparatus to a person, animal, or object, such as a child. For instance, in particular embodiments, the monitoring apparatus may include a band, such as a flexible and/or stretchable band that may be worn around a part of the body, such as a neck, wrist, or ankle, or attached to another article. The housing may be made of one piece, continuously joined end to end, so as to form a complete continuous loop that is a unitary unit which deforms in some manner during the attachment process and reforms once attached for ease of wearing. Alternatively, the housing may include first and second ends that are joinable via a clasping mechanism configured to clasp and secure the first and second ends together, such as around the neck, wrist, or ankle of the user. In certain instances, the monitoring apparatus is retained within the housing, such as between first and second surfaces of the housing; and in other instances, the monitoring apparatus may be removable from a band or necklace, in various manners, and the clasping mechanism may be configured for allowing the monitoring device to be removably attached therewith.

The identity, position, and/or health monitoring apparatuses, systems, and their methods of use provided herein below with reference to the appended figures are configurable and capable of one or more of identifying information about the user, or a condition of the user, the position or location of the user, and/or for monitoring a physiological condition of the user and/or his or her environment. Accordingly, in some instances, the identity, position, and/or health monitoring apparatus simply functions as an electronic identifier of the person wearing the apparatus. In other instances, the monitoring apparatus functions to simply monitor the position of the wearer of the apparatus, such as in relation to a second or third party monitoring device(s), such as a device to which it is paired. For instance, where the wearer is a child, the monitoring apparatus may be formed so as to be worn around the wrist or ankle of the child, and may be configured for communicating with a monitoring device, e.g., a "master" device that may be a mobile computing device, such as of the parent or guardian of the child, for example, to keep track of the child's position in relation to that of the parent or guardian. In further instances, the monitoring apparatus may simply function to identify a record, such as a record of a medical condition, such as an allergy to a medication, an alert as to having diabetes or glycaemia, or other such disease, and the like; and in some instances the monitoring device may function to monitor and/or collect physiological data of the wearer and/or his or her environment.

For example, in some embodiments, the identity, position, and/or health monitoring apparatus, e.g., geolocation device, may include a physiological and/or environmental data collector, such as one or more sensors, which may be configured to collect characteristic data, such as physiological data associated with the child, his or her environment, and/or their performance level in an activity, such as an activity requiring mental or physical exertion. In such an instance, the monitoring apparatus may include electronic circuitry that is configured to receive physiological and/or environmental data associated with the child and/or the child's environment, and in some instances, may further be configured for processing that physiological and/or environmental data, and/or wirelessly transmitting the physiological and/or environmental data to a secondary or tertiary monitoring device, such as a mobile electronic device of a second party, such as a parent of the child, or a third party, such as a health care monitor, for display thereby, such as on the mobile electronic device of the parent or desktop computer of the healthcare professional. In various embodiments, the monitoring apparatus may be configured for performing a combination or even all of: functioning as an electronic identifier, a position detector, and/or a physiological condition monitor.

Accordingly, in various embodiments, a system is provided, wherein the system includes one or more, e.g., a plurality, of devices that are capable of being communicably coupled together, e.g., paired, in a manner that communications of various forms may be transmitted and received from one to the other, either directly or via or tertiary serer and/or database, such as where the communications are encrypted/decrypted prior to and after receipt thereof. In such instances, one of the devices, e.g., a first device, may be configured to assume a dominant or controlling role over the other device, e.g., a second device, and as such the paired devices may be referred to herein as being within a master/servant relationship with respect to one another.

As can be seen with respect to FIG. 1A, in one aspect, a personal tracking, e.g., geolocation, device, such as an identity, position, and/or health monitoring apparatus 1 is provided. With reference to FIG. 1A, the apparatus includes a substrate 7 upon which electronic circuitry 8 has been printed, so as to form a printed circuit board 10. In particular embodiments, the electronic circuitry 8 is configured so as to form a central processing unit 12. The circuit board may include additional components such as a memory 14 and a communications module 16 that are operably coupled to the central processing unit 12, all of which may be powered by an onboard power source 18, such as a battery. In some instances, the circuit board 10 may include an input/output (I/O) 19 device operably coupled therewith. Together the circuit board 10 containing the central processing unit 12, the communications module 16, battery 18 and/or the memory 14 and/or I/O 19 may be configured as a chip 20 that is attachable or otherwise capable of being mounted to a housing 40, for easy transport, and/or may be configured to be coupled with or otherwise made part of a secondary article 50, such as a bracelet, so as to be capable of being worn by a user 100.

For instance, in one particular implementation, the geolocation device 1 may be a printed circuit board 10 that includes a chip 20 that is capable of being coupled to or otherwise carried by or within a band, such as a sports band capable of being worn, and may be used to track the whereabouts of the wearer, which may be especially useful where the wearer is a child, such as a child prone to wandering off or in an environment that renders the child susceptible to abduction. Accordingly, in one aspect, the chip 20 may simply include a substrate 7 having electronic circuitry 8 printed thereon, which electronic circuitry functions to collect and process information about the child, the child's location, his or her condition, and/or the environment that they are in. In various implementations, the substrate 7 may be a circuit board 10 and the electronic circuitry 8 may be configured to function as a central processing unit (CPU) or graphics processing unit (GPU) 12.

In particular embodiments, the electronic circuitry 8 may be configured so as to from a processing unit, such as CPU 12, which CPU 12 may comprise a microprocessor. The microprocessor 12 may be coupled to the substrate 7 to from at least part of circuit board 10. In various embodiments, the microprocessor 12 may be a microchip, which microchip 12 is capable of being coupled to the circuit board 10 and is configured for performing various processing functions related to identifying, locating, and/or sensing a condition of a user 100 to which the chip 20 is coupled. Additionally, in various instances, the microprocessor 12 may be configured so as to include an onboard memory, communications module, and/or an input/output for communicating with the circuit board 10. Hence, in certain embodiments, the identity, position, and/or health monitoring apparatus 1 is configured for communicating the same to a third party, such as over an associated network, e.g., to a paired master device or server and/or through a cellular telephone connection.

For example, in various embodiments, the identity, position, and/or health monitoring device may include any suitable processing unit, such as an Intel® or Arm® core processing unit and/or microprocessor. Particularly, the processing unit may be a high-frequency, low latency processor. For instance, in certain implementations, the processor may be a 1.3 Ghz 32-bit ARM® CPU. In one implementation, the processor may be a SNAPDRAGON® 1100 chipset. Additionally, as indicated, the processor may be coupled to one or more memories, such as any suitable memory, for instance, a RAM, ROM, NAND flash or FRAM. In various implementations a plurality of memory resources may be provided. Particularly, in various embodiments, the processor may be coupled to tens or hundreds, or even thousands, of memory resources. Particularly, the processor may be coupled to 10, or 50, or 100, or 250, or 500, or even 1000 or more of megabytes of FLASH and/or RAM memory.

Further, as indicated, in particular embodiments, the tracking and/or monitoring device may be configured for performing one or more communications, such as cellular communications, SMS text messaging, instant messaging, WIFI, Bluetooth, as well as RF communications, and the like. Particularly, in various implementations, the communications module may include one or both of a suitable transmitter and/or a suitable receiver. For example, a typical transmitter may be a radio frequency (RF) transmitter, a cellular transmitter, WIFI, and/or other wire replacement communication mechanisms, such as Bluetooth®, such as a low energy Bluetooth® transmitter unit. More particularly, in certain implementations the device may be configured for cellular communications and/or tracking, and as such, the device may include a SIM card and/or may be configured for pairing with a device having a SIM card, such as for SIM card sharing. Specifically, in certain iterations, the tracking and/or monitoring device may have LTE cellular connectivity capabilities, as well as GPS, which capabilities may be employed for one or more of tacking and/or communications, especially for tracking and/or monitoring an individual across regions and/or events. In various implementations, the device may be configured for being constantly connected to a network, such as an LTE network, so as to be able to be used constantly, e.g., without having to be powered up.

In various embodiments, as described herein below, the device may be configured for streaming data and/or music. As such, the devices may include one or both of WIFI and/or BLUETOOTH® connectivities. Consequently, in various instances, the device is configured for sending and receiving wireless communications, such as in a manner to download and/or receive, e.g., stream, music data files, and other information, wirelessly, such as through Bluetooth audio connectivity. In particular embodiments, the device is configured for connecting with wireless headphones, such as Bluetooth enabled headphones and/or microphone, e.g., for listening to downloaded and/or streaming audio files and/or for giving voice commands. Accordingly, in such a manner as this, a wearable device of the system may be configured for placing and receiving calls, such as through a voice enabled microphone of the device and/or suitably configured Bluetooth headsets and/or microphones.

Such cellular communications may be through an inherent SIM card and/or through the device sharing the cellular number of a paired or otherwise suitably synced smartphone. For instance, the device may be configured for sharing a phone number with a cellular phone service, such as through T-MOBILE'S DIGITS®, AT&T NUMBER-SYNC, or similar services offered by VERIZON®, SPRINT®, and the like. Hence, through one or more of these various elements may allow the tracking and/or monitoring device to send and/or receive audio and/or video files, initiate or receive voice calls, send text messages and/or SMSs, as well as stream music and receive audio files for playback. In particular embodiments, the device of the system may be configured for performing communications through one or more social media services, such as through WHATSAPP®, FACEBOOK MESSENGER®, TWITTER®, INSTAGRAM®, SNAPCHAT®, and the like. Likewise, through the microphone the device may be configured for connecting and/or communicating with one or more suitable digital assistants, such as those powered by GOOGLE®, AMAZON®, or the like, which interactions will allow for the device, such as a child using the device, to ask and/or seek answers to questions simply by speaking into a microphone of the device. In such embodiments, a speaker or wireless headset may be provided so as to receive and listen to the response.

Additionally, in particular embodiments, the tracking and/or monitoring devices are configured for connecting with a remote database, such as through a wireless cellular or WIFI enabled internet connection, such as for streaming music, such as live or pre-recorded music. For instance, the device may be configured for connecting with a streaming music service, such as SPOTIFY®, PANDORA®, or the like. Any suitable question may be asked and/or answered in this manner, such as what time it is, directions may be mapped and/or sought in audible format, and/or music may be streamed, such as by voice command.

Accordingly, in view of the above, the device and system may be configured for connecting to and/or switching from WIFI to cellular connectivity based on the signal strength of the connection and/or range, and the like. In such instances, a connection may be made first through WIFI, and may then switch to cellular connectivity, as necessary to ensure maximal connection strength. Specifically, the cellular components of the device may be configured to ensure a narrow to high frequency and bandwidth, as needed, such as a high enough frequency and bandwidth to ensure a high streaming quality ratio, such as for streaming high quality audio and/or video files. For instance, in various embodiments, the bandwidth may be at about 50, such as at about 100, about 250, about 500, or even about 1000 kbps, or higher, such as to ensure reliable and smooth music and/or streaming and/or playback. In such an instance, the included processor and/or memory may be configured for encoding and/or decoding high quality video and/or audio streaming. It is to be noted that as microprocessors become more efficient, and cellular connectivity stronger, battery usage lowers, and the battery is more able to supply power more efficiently. Hence, in various instances, the device may have a battery that is configured for supplying 1, or 2, or 3, or even a weeks worth of power to the device, such as in standby mode, and up to an hour, or 3, or 5, or 10 or even an entire day during streaming.

Such processing may be performed by a suitably configured Snapdragon 1100 CPU or other such processor, such as for performing LTE communications. Cellular capabilities may be at 2G, 3G, 4G, such as 4G LTE, or even 5G, so as to make the streaming of data both powerful and efficient. Hence, the cellular communications module may include a SNAPDRAGON® processing module, and/or may be a LTE Cat1 Module, a LTE Cat-M1 or NB-IoT module, or the like. In particular embodiments, the chipset may be an ALTAIR®, or SEQUANS, or other high bandwidth chipsets that are configured for high quality audio and/or visual transmission and receipt. Further, as indicated above, in various instances, a plurality of processors may be included in the devices, such as in a sequential and/or stacked configuration, and likewise for the memory resources.

In particular instances, the microprocessor may include a plurality of processors, e.g., microchips, which may have a stacked configuration. For instance, in various embodiments, instead of being spread across a plurality of circuit boards or circuit board elements, as described herein, in certain embodiments the microprocessors may be organized in such a manner that one is positioned on top of the other in close knit proximity. Such a configuration has the advantage of increasing processing power at the same time as requiring less power, generating less heat, and reducing bandwidth. Further, the stacked configuration allows for much smaller interconnects, than in a side by side organization, and as such greater processing speeds may be achieved. These interconnects are specially designed so as to allow communication between the stacked layers. These technologies include the Bump+RDL, through-silicon via (STV) stacking, e.g., employing vertical copper channels built into each die, as well as silicon transposer, and other such tightly coupled communication technologies, e.g., allowing for shorter wiring at higher bandwidths and lower power consumption.

Accordingly, in particular embodiments, the microprocessor may be a 3-D microprocessor such as is available from ARM RESEARCH®, AMD®, INTEL®, NIVIDIA®, e.g., AI VOLTA®, XYLINX®, SAMSUNG®, e.g., 64-99 layer V-NAND® chip, and the like. Hence, as discussed herein in detail, instead of the various components of the geolocating and/or health monitoring and communicating device being spread across a multiplicity of circuit boards arranged along a horizontal plane, they may instead, or in addition to, be positioned on a multiplicity of circuit boards arranged vertically, such as in a stacked 3-D configuration, e.g., 3-D wafer level chip packaging.

Specifically, the various components of the device may be etched, or otherwise positioned, so as to form a plurality of chipsets that are stacked one on top of the other and which may be hermetically sealed with one another, e.g., so as to form a package. In such a manner as this, two or five or ten or twenty or thirty or fifty or even 75 or 100 or more chips may be stacked forming layers one on top of the other, where processing functions may be performed discretely on a dedicated chip on a function by function basis, or may be spread across a plurality of chips.

Likewise, one or more memories may be in a stacked, e.g., on top of the logic circuit, or side by side orientation relative to the stacked chipset. This memory stacking allows for a very tight, short coupling with the processing function thereby allowing for much shorter interconnections and faster lookup times, making processing orders of magnitude faster and more powerful. In various embodiments, these configurations allow for 35-50% decrease in package size, 50% or more less power consumption, as well as an 8-10× bandwidth improvement. For instance, in certain embodiments, a DRAM or DIMM, NAND flash, or other memory device, may be tightly stacked on another CPU and/or GPU chip, which may be stacked on top of one or more chips and/or memories. In such an instance, where these two devices, e.g., in a horizontal configuration may be several mms or even a cm or more part, in the stacked configuration they may be less than a mm or even less than a micrometer apart. Accordingly, in various instances, a plurality of memories may also be in a stacked or interweaved configuration with the various stacked microchips. Further, in various embodiments, one or more of the cellular, Wifi, Bluetooth, GPS, image and/or position sensing, and other communication and/or locating functionalities may also be in a stacked configuration.

Accordingly, as can be seen in FIG. 1A, in various embodiments, in addition to including the microchip 12 having one or more microprocessors therein, the circuit board 10, and/or microchip itself, may additionally include or otherwise be operationally coupled, e.g., in a horizontal or 3-D arrangement, with one or more other modules, such as a memory 14, a communications module 16, an input/output module 19, all of which may be powered by a power source 18. Additionally, in certain embodiments, the circuit board 10 may be configured as a small chip 20 that may be operably coupled to one or more sensors 30 and/or one or more displays 25. More particularly, in various instances, a substrate 7 is provided wherein the substrate may be a circuit board 10 or otherwise include one or more of a microprocessor 12, a memory 14, a communications module 16, and an energy source 18, e.g., a battery, powering the same. In certain instances, the circuit board 10 may include an input/output module 19, a sensing mechanism 35 being operably connected to a sensory control unit 30 and/or the microprocessor 12, and/or may be coupled to a display 25. In particular embodiments, the microchip 12 may be any suitable processing unit, such as an Intel® or Arm® core processing unit and/or microprocessor. Other processors may also be included, such as a QUALCOMM® SNAPDRAGON®, ALTAIR®, or SEQUANS, or other high bandwidth processor may be included individually or simultaneously.

The memory 14 may be any suitable memory such as a RAM, ROM, NAND flash or FRAM. The communications module 16 may include one or both of a suitable transmitter 16A and/or a suitable receiver 16B. For example, a typical transmitter 16A may be a radio frequency (RF) transmitter, a cellular transmitter, WIFI, and/or a Bluetooth®, such as a low energy Bluetooth® transmitter unit. In some instances, a typical receiver 16B may include a satellite based geolocation system or other mechanism for determining the position of an object in three-dimesnsional space. For instance, the geolocation system may include one or more technologies such as a Global Navigation Satellite System (GNSS). Exemplary GNSS systems that enable accurate geolocation can include GPS in the United States, Globalnaya navigatsionnaya sputnikovaya sistema (GLONASS) in Russia, Galileo in the European Union, and/or BeiDou System (BDS) in China.

Figure 1B:
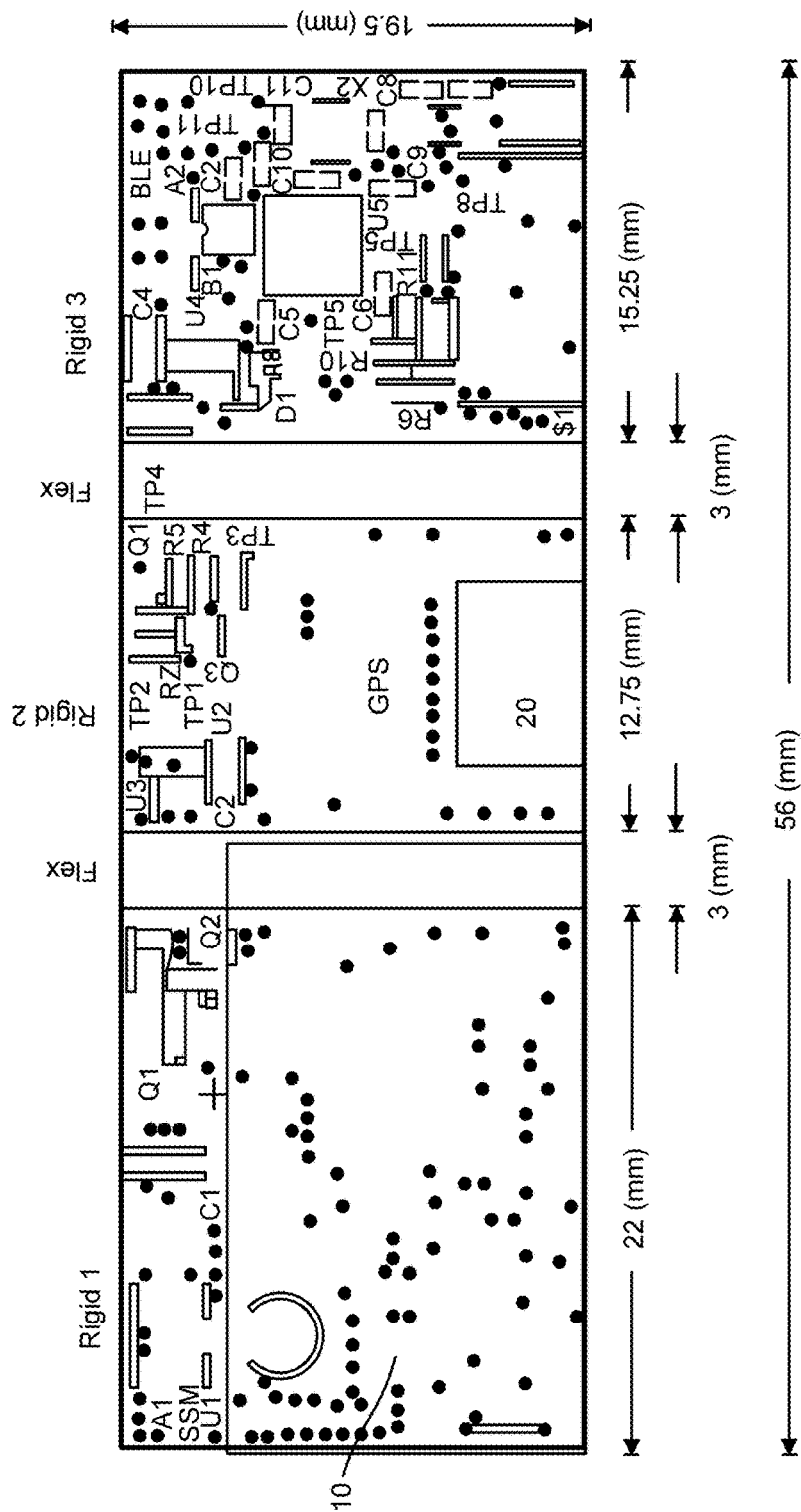
FIG. 1B is a view of an exemplary flexible identity, geolocation, and/or health status monitoring apparatus, configured to be encased within the bounds of an auxiliary retaining device, such as a bracelet.
Figure 1C:
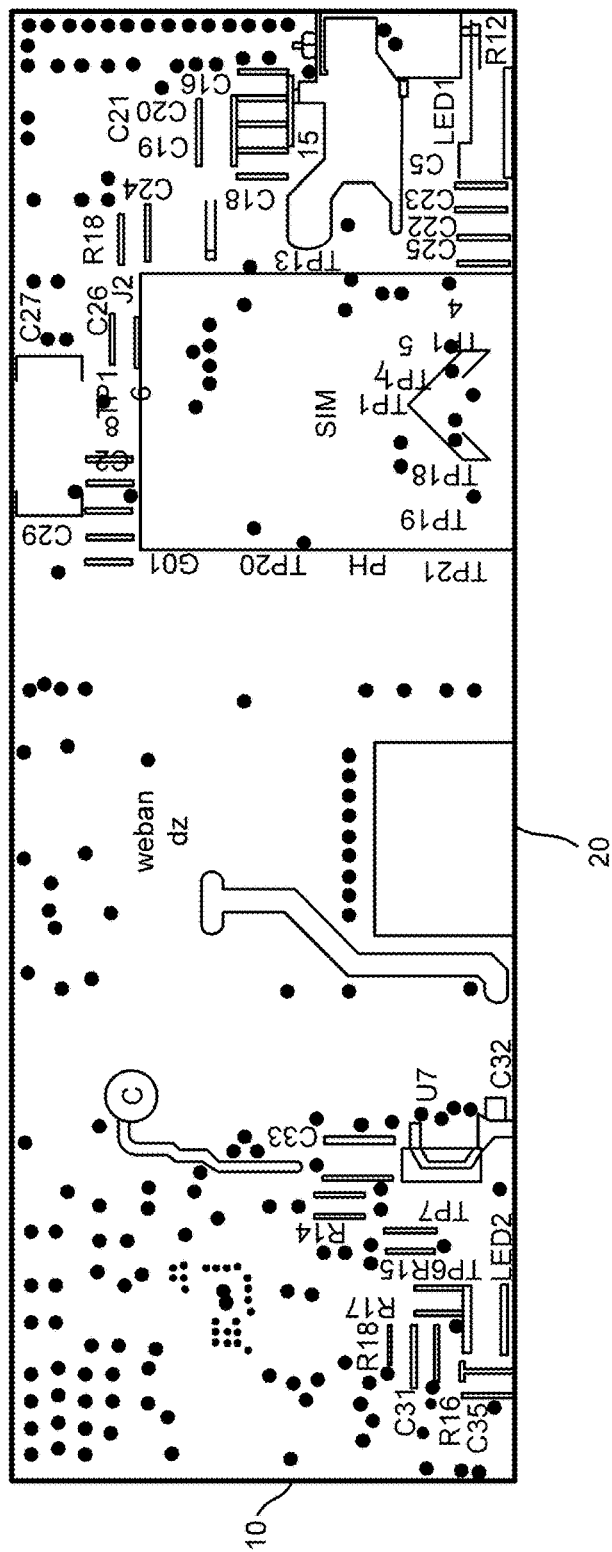
FIG. 1C is a view of another exemplary rigid or semi-rigid, identity, geolocation, and/or health status monitoring apparatus of the disclosure.

In various instances, as seen in FIG. 1B, the microchip 20 may part of a circuit board 10, such as a flexible or semi-flexible digital logic circuit board. The circuit board 10 may be a printed circuit board that includes the various components of the system 1. As described above these components may include one or more of a microchip 20, a memory 14, a communications module 16, an input/output module 19, a power source 18, and the like. One or more of these components may be operably connected to one another such as by one or more inter connects, such as flexibly printed interconnetcs. Additionally, in certain embodiments, the circuit board 10 may include one or more I/Os 19 and/or may be electronically coupled to one or more sensors 30. In particular instances, the circuit board 10 may be rigid or semi-rigid and may include or otherwise be coupled to a GPS module, as shown in FIG. 1B, and/or a SIM card and/or chip set, as shown in FIG. 1C.

Figure 1D:
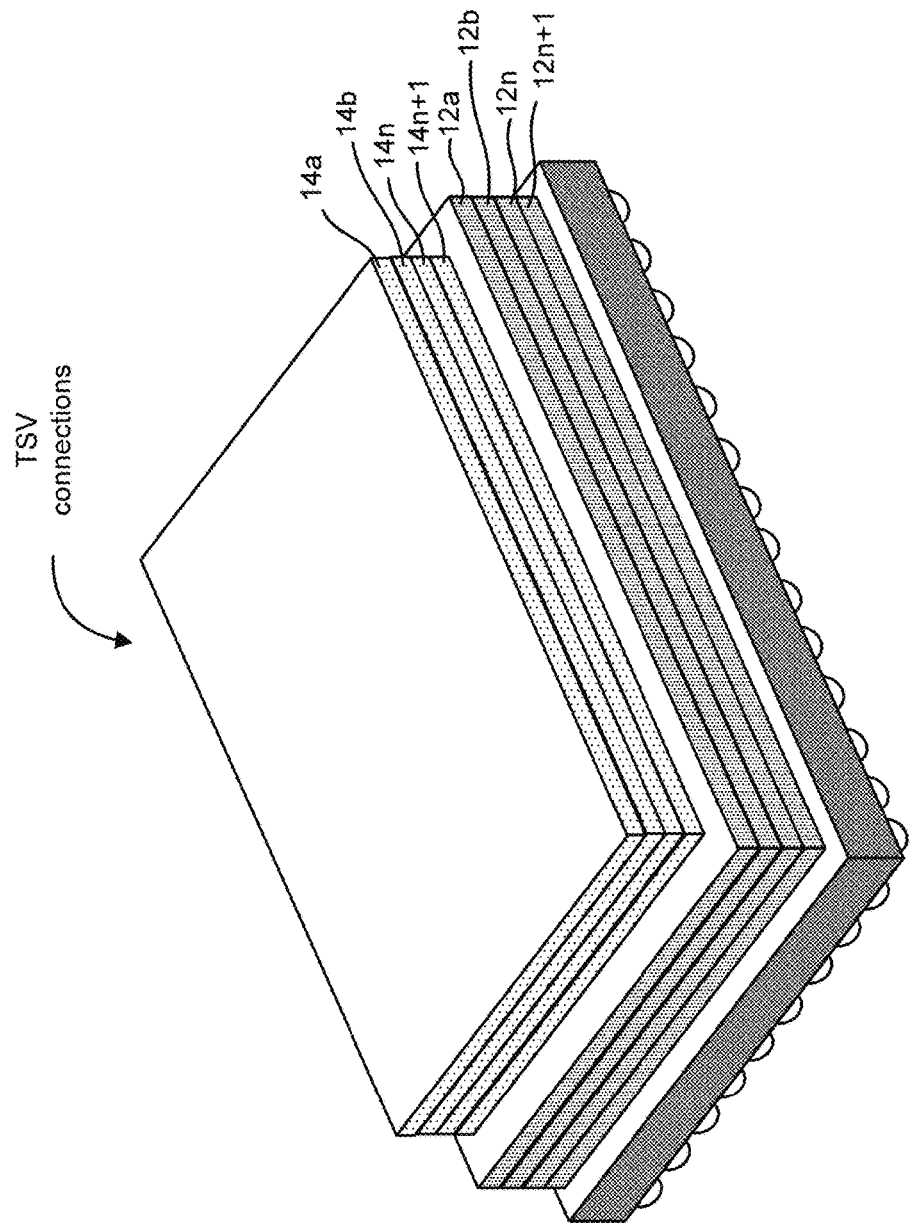
FIG. 1D presents a perspective view of a stacked microchip/memory arrangement, for use in the identity, geolocation, and/or health status monitoring apparatus of the disclosure.
Figure 1E:
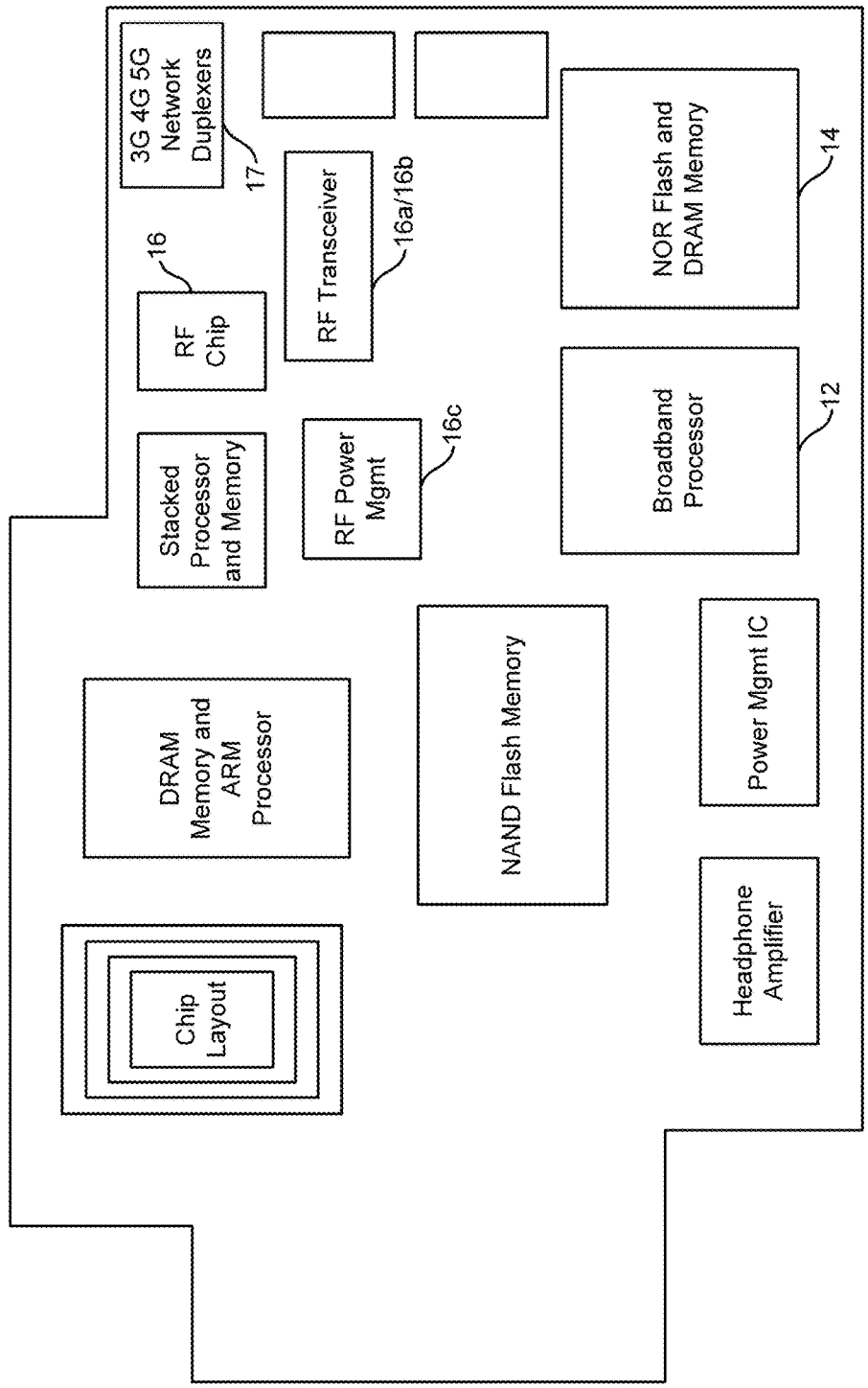
FIG. 1E presents an exemplary circuit board arrangement including the stacked microprocessor/memory of FIG. 1D, wherein the circuit board is further configured for enacting one or more communications, e.g., cellular communications, protocols.

In various instances, as shown in FIGS. 1D and 1E, the microchip and/or circuit board arrangement may be in a stacked configuration. For instance, the substrate or circuit board 10 may be configured so as to include a processor and/or memory stack, so as to include a multiplicity of stacked processors, such as processing layers 12a, 12b, ... 12n, and/or 12n+1 layers of processors. Additionally, in various embodiments, a plurality of stacked memories may also be included, such as memories 14a, 14b, ... 14n, and 14n+1. The processor and/or memory layers may be connected to one another through one or more tight-coupling interconnects, which interconnects may be configured to allow the various layers to communicate with one another while being spaced in very close proximity to one another, such as at a distance of 1 mm or less, such as 1 micrometer or less, such as 1 nanometer or less. In particular embodiments, the interconnect may be a TSV or similar pass through connection.

Likewise, FIG. 1E presents one particular embodiment of a stacked circuit board arrangement, incorporating the stacked processor/memory configuration of FIG. 1D. In this embodiment, the circuit board arrangement includes the stacked processors and memories 12 and 14, respectively, as well as a communications module that includes an RF module 16, an RF transceiver 16a and 16b, an RF power manager 16c, a 3G, 4G, and/or 5G network duplexer 17, and an additional broadband processor 12. A further memory 14, e.g., such as one or more of a DRAM, DIMM, NAND, Flash, and/or other memory may also be included, where these additional processor (e.g., broadband) and/or memory devices are not part of the stacked arrangement, although, it is noted that in other embodiments, they may be included in the stacked arrangement. Additionally included is a power managing integrated circuit as well as a headphone amplifier, such as for use with a pair of wireless, e.g., Bluetooth head phones. Further, as indicated one or more of a SIM card, GPS, and/or WIFI, Bluetooth, LE Bluetooth device, and the like, may also be included, such as in a stacked and/or horizontal configuration as disclosed herein, as shown with respect to FIG. 1A.

Accordingly, in particular instances, a geolocation and/or monitoring device of the disclosure may include an elongated substrate forming a flexible or semi-flexible or articulated digital logic circuit board arrangement, which circuit board may be contained within a cavity of an elongated body of the substrate or a first and/or second surface of an encasement housing the substrate, e.g., within a cavity thereof. In such an instance, the semi-flexible digital logic circuit board arrangement may include a plurality of rigid circuit board portions that may be connected by one or more flexible portions, such as where the digital logic circuit board arrangement is positioned between the first and second surfaces of the elongated body of the substrate. In some instances, the one or more of the rigid circuit board portions of the digital logic circuit board arrangement may include a central processing unit (CPU) or graphics processing unit (GPU), a communications module, a memory, and an energy source, e.g., a battery, such as where the CPU or GPU is operably connected to both the memory and the battery.

The energy source 18 may be any suitable source of energy such as a battery, such as a wireless charger, solar, thermal, motion, or other renewable energy source and/or rechargeable battery, such as a curved battery having a long energy life. For instance, a long battery life may be achieved through a combination of functions of components, such as through the use of Bluetooth Low Energy (BLE) RF technology. For example, the chip, chipset, and/or housing having a suitably configured transmitter and/or receiver, e.g., GPS, may be configured for being paired, such as in a master/servant relationship with another device such as a mobile phone device, such as with the smart-phone of a parent and/or guardian.

In such an instance, when the wearer of the device, e.g., the child, is within a selected range, e.g., within 5, 10, 15, 20, 25, 30, 40, 50, 60, 70, 75, or even 100 feet (meters or yards) from the connected device, the higher energy consuming functions, such as the GPS function, may be turned off, e.g., manually or automatically, and hence energy will be conserved because the higher energy functions, e.g., GPS and/or cellular communication functions, are not being employed. Particularly, in some instances, a typical power draw of the device while paired with a smartphone, tablet, or other BLE device may be less than 1000 uW, less than 500 uW, less than 250 uW, less than 150 uW, less than 100 uW, less than 75 uW, less than 50 uW, less than 25 uW, less than 15 uW, or even less than 10 uW. More particularly, the energy saving dynamics as herein described may be such that when paired with a BLE device, the device, e.g., bracelet, may run for over 1 or 2 years on a simple coin cell battery (e.g., a typical 2032 coin battery holds 600+ mWH of power, 600 mW/50 uW=600/0.05=12000 hours=500 days). Further, when the device is operated in the BLE mode exclusively, then the battery life may be up to about 3, 4, or 5 years, dependent on the configuration. Accordingly, given these results, the device may be configured to optimize its functionality with respect to prolonged and/or enhanced operation in the BLE connection mode.

However, when the geolocation device, e.g., bracelet loses connectivity with the master, e.g., parent's device, it may automatically switch to cellular communications mode, or may not immediately switch to cellular communication. For instance, in certain instances, it may first attempt to connect to any other previously paired device, such as switching from one parent's phone to another, of rom one relative to another, or from one safe location beacon to another. If such a connection is not established, it may also try again to connect with a previously paired, safe device, such as the Dad's phone. This allows for any momentary RF disruptions to be handled without substantially impacting the battery life of the device. For example, in some instances, only when a carefully selected amount of time with no connection and/or communication has passed will the device, e.g., bracelet, power up the GPS and/or cellular communication hardware. Further, the device may be configured such that at all times while not in a BLE connection, the bracelet may periodically and/or continually attempt to re-establish a BLE connection, which operation may be configured to take extremely little power.

For instance, in certain instances, the geolocation and/or status monitoring device, e.g., bracelet or pendant, may be configured for communicating with a controlling device, e.g., a master device, and possibly one or more other geolocation and status monitoring devices, or third party device, e.g., computer, such as to alert a user, parent, or third party monitor to the location of the geolocation device and/or status monitoring device. Such controlling devices can be standalone, dedicated devices such as devices that may be solely or at least primarily dedicated to communicating with and/or controlling the geolocation and/or status monitoring devices; or the control device may be a general purpose communication device (e.g. a home or portable computing device, such as a smartphone, a tablet computer, a laptop computer, a mini-tablet device, or the like) or server associated with a database.

The controlling device may be a single device or the user(s), e.g., parent and/or child, may switch between two or more controlling devices, such as where the parent or other monitor may track two or more geolocation devices, such as that of multiple children wearing the bracelets. In some instances, features and functions described elsewhere herein as part of a controlling device can be provided by one of a plurality of devices associated with multiple objects, e.g., children. Hence, in various embodiments, the geolocation and/or control devices disclosed herein can optionally include a processor and/or communications hardware that can permit the personal devices to communicate with one another, and in some embodiments to allow one or more, e.g., of the paired devices, to act as a controlling device.

Particularly, in some instances, a user, e.g., a parent, may require location data, or proximity information, and/or status data regarding his or her child or children and/or their environment. In many instances, the parent or operator of the controlling device will want to know the child is at a particular location, or within a certain radius of the parent, e.g., the parent's controlling device that is synched or otherwise linked via one or more wireless communication protocols to the geolocation and/or monitoring device, e.g., bracelet or pendant, associated with the child, pet, or object, and/or to know the status of one or more conditions of the child, pet, or object such as at a particular time. In certain of such instances, the controlling and/or geolocation device may, e.g., on a pre-determined schedule or intermittently, be programmed to expect a wireless communication signal from the other device, such as the geolocation and/or status monitoring device to the control device, or vice-versa, so as to allow the associated devices to communicate and/or track one another.

Consistent with the present disclosure, the controlling device and/or geolocation and/or status monitoring device may emit an alarm or warning if such a signal is present after a period of being absent, or absent after a period of being present. Additionally, the controlling device and/or geolocation and/or monitoring device may emit a signal, such as a visual or sound indication or vibratory warning when such a wireless communication signal from the geolocation and/or status monitoring device is detected, after a period of absence, or not detected, after a period of presence. The wireless communication signal may be arbitrarily received or may be received in response to a communication sent to the to or from the controlling device. The communications may use one or more communication protocols such as variants described in the IEEE 802 standard, or proprietary wireless communication techniques. For example, the controlling device and geolocation and/or monitoring device may use variants and/or combinations of wireless communications signals, such as Bluetooth®, ANT, WIFI cellular data (e.g., LTE), etc., as described above.

Further, as described above, in some instances, the controlling device may instead locate the geolocation and/or monitoring device using longer-distance wireless communication schemes, including cellular networks, such as by comparing absolute locations of the controlling device and the geolocation and/or monitoring device. For instance, absolute or near absolute location data may be obtained or derived by detecting and analyzing signals from a Global Navigation Satellite System (GNSS), such as the Global Positioning System (GPS). In some embodiments, signals from other known-location transmitters, for example cell phone signal towers, may be used in place of, or to augment, GNSS signals.

In some instances, the controlling device may transmit to and/or receive location information from the geolocation/status monitoring device by use of wireless data networks, such as WIFI, or cellular data networks, or wireless direct communications. Such wireless communications over a network may utilize dynamically assignable addresses such as one or more of those used in TCP/IP protocols, the controlling device may use IP and/or typically more-persistent and device-specific MAC addresses for direct controller-to-location/status device communication, or for network communication via a routing device. The signal strength of a radio signal communicated between the controlling device and the geolocation and/or status monitoring device may also be used to determine the distance between the device, e.g., bracelet or pendant, and the controlling device.

Determining the geolocation of the geolocation and/or status monitoring device may be aided with the addition of a magnetic compass or magnetometer that detects changes in direction of the monitoring and/or monitored device, which components may be part of the controller and/or geolocation and/or status monitoring device, e.g., bracelet or pendant. Determining the location of the geolocation and/or status monitoring device may be accomplished using the device itself, which can house a power source, such as a battery, a communications module, and a circuit board with a processor, as described above. Alternatively, the geolocation device may transmit the location data to the controlling device, and the controlling device may analyze the location data to determine the location and/or other characteristics of the geolocation and/or status monitoring device, or vice versa. In other instances, the location data collected by the monitored device may be stored on the device, and then accessed at a later time for analysis to determine locations of the monitored device over time. The monitoring and/or status, and/or controlling, device can determine and/or store the date and time and/or condition of the device when location data is collected.

The controlling or geolocation device may utilize a known location of the location, such as a location of geolocation and/or status monitoring device, compare this known location to its own known location, and issue a warning or emit an alarm when the location and status device is farther away from the controlling device than a predetermined threshold distance or is within a predetermined proximity of the controlling device, as described generally above. For instance, the location, control, and status device, such as a bracelet and/or mobile phone, may issue a warning or emit an alarm or other signal when the geolocation and/or control device is farther away from the other, e.g., geolocation device, than a predetermined threshold distance or is within a predetermined proximity of the other device, such as an electronic device such as a mobile computing device, tablet computer, or mobile phone. For example, a geolocation and/or status monitoring device, such as a bracelet or pendant, may be configured for lighting up when it approaches a user, e.g., parent, holding the controlling device, and/or vice versa, e.g., the control device, mobile phone, may be configured for lighting up, vibrating, sounding an alarm or otherwise signaling when the geolocation and/or status monitoring device approaches the control device, or vice versa. An alarm can include, but is not limited to, an audio alarm, a visual alarm, a vibratory alarm, a message sent to another device, or any combination thereof.

Besides being notified of the proximity or distance between the two devices, e.g., the controlling device and the geolocation device, a user may wish to actively track the movement of the device in real-time. For instance, the controlling device may have the ability to actively track the location or status of the location, control, and status device, such as on a map of the area surrounding a user or the area surrounding the geolocation and/or status monitoring device. For example, the controlling device may alternatively have the ability to actively track the location or status of the geolocation device such as by indicating the time and the distance between the user and the geolocation device and may chart the same such as on an electronic graph, table, or map. Such active tracking and/or monitoring may be accomplished via a dedicated software application on the controlling device and/or tracking device, a software application running on remote server, or via a website.

In some embodiments, the geolocation and/or status monitoring device may communicate directly or indirectly with a server via a private or public network (e.g., the Internet). For example, a shopping mall, town, or city, or transportation hub, such as an airport or airline, may provide communication beacons or nodes or relays, as described herein, at strategic locations for collecting information about/from a geolocation and/or status monitoring device. The node/relay may detect the presence of the geolocation and/or status monitoring device and report such detection to a computer server and/or a control device. In some instances the node or relay may obtain information specifically identifying the location status monitoring device, along with its status. A location of the location and status monitoring device may be derived with respect to proximity of the node/relay, or may be reported from the location and status monitoring device to the node/relay. The identifying information may be recorded at the node/relay for future use, or may be forwarded to a computer server for any of several purposes.

For instance, location and/or status information obtained by such nodes/relays may permit statistical evaluation of locations and statuses of the wearer of the bracelet to aid the monitoring and/or control device to evaluate location and/or status history of the child or other wearer of the band. Such a system may be employed by homes, communities, towns and/or cities to monitor locations and/or statuses of the children living in those places. Moreover, specific obtained geolocation and/or status information may be presented on an access-controlled website for access by an enrolled parent or authorized monitor of the geolocation and/or status monitoring device. In certain instances, the provider of the network and/or owner of the information may require a user to subscribe to a service in order to access the information. This service may be offered for valuable consideration. All, or a part of collected geolocation and/or status information for one or more location and status monitoring devices may be made available, in various levels of specificity and/or aggregation for offering to various third parties.

In particular instances, to facilitate one or more of these implementations, a software and/or hardware application may be present and executed by one or more of the controlling and/or geolocation device and may provide a user interface that can display information from or about the location and/or status of the geolocation and/or status monitoring device(s) and/or the control device. The interface may further provide input portions that permit the user to enter information and/or commands. For instance, such a software application may be in the form of a "mobile app" for use on or execution by a mobile smartphone or dedicated device or processor thereof, or may be in the form of a software application for execution in a conventional personal computer (e.g., desktop or laptop or tablet) or enterprise computer system.

In various instances, the application's display features may include input mechanisms including mechanical or virtual: buttons, sliders, switches, text inputs, menu selections, and the like for entering data or changing settings. Accordingly, input mechanisms may include physical or virtual inputs such as keys, buttons, sliders, switches, etc. Moreover, the software application may utilize sensors provided in the controlling device itself and/or the geolocation and/or status monitoring device, including, but not limited to attitude, altitude, barometric and/or temperature sensors, accelerometers, gyroscopes, light sensors, user proximity sensors, microphones, speakers, etc. The display may present information textually and/or graphically. Graphics may include use of geographic maps, graphs, arrows, contour maps, level meters or charts, dials, gauges, and the like, or combinations thereof. Various modifications to the herein described may be employed for presenting a user with a view of data and/or means to interact with the software application for control of a location, control, and status monitoring device or data associated therewith.

For instance, an exemplary software application may present a user with a one or more menus or screens configured at least for permitting viewing and/or selection of user preferences or settings, for viewing data received from or related to one or more geolocation and/or status monitoring devices, and for controlling functions and/or determining the status of the location and/or status monitoring device(s). The application may include communication settings such as for pairing/bonding a geolocation and/or status monitoring device with a relay and/or controlling device (e.g., the device executing the software application). In addition to such control and presentation of wireless (or wired) "handshaking", communication features may include transmission of commands and settings, receipt of sensor data or historical data, alarm/warning notifications (e.g., at loss or attainment of proximity), etc.

In one example the communication features may permit a user to select among multiple available signals for use in calculating a location of a geolocation and/or status monitoring device. Additionally, the user, e.g., parent, may be presented with a list of typical use scenarios that correspond to a particular set of available signals. For example, the user might select from among "tracking" and/or "proximity" settings, where an particular setting selection may permit utilization of signals typical of that setting (e.g., various radar, cellular, and/or other signals). For instance, selecting a "child tracker" setting may utilize GPS and/or cellular signals more typically available for outdoor use, while selecting a "proximity" setting may use only a device-specific type of communication (e.g., Bluetooth® Smart). Such communication modalities may also be useful in determining the status of or otherwise controlling the tracking, geolocation, and/or status determining device.

For display settings a user may, in certain software and/or hardware application implementations, select from among color schemes, graph types, data types for display, analysis types for calculation and display, percentage vs. absolute amounts, etc. The application may present options for whether, and in what way, to display certain information. For example, the settings may permit overlap of certain data (e.g., location and proximity) for presentation in a single screen, or may permit selection of the type and number of screens that a user may scroll through, each screen presenting different data, or a different view of data.

Moreover, the communication features of the software and/or hardware application may permit a user to interact with a third-party server or website in order to view sensor data, comparative data (e.g., with other users or pets, similar items, similar locations or destinations, etc.). Communications with a third party may include a subscription component permitting the user of the software application to initiate and maintain a subscription to third party services. That is, a party other than the software application user may provide subscription services for which the user may enroll. The communication features of the software application may directly or indirectly provide the user with a way to securely transmit personal and/or financial information for such subscription. The communication features of the software application may also permit a user, e.g., parent or pet owner, etc., to detect changes in the geolocation or status of the child wearing the wearable in real-time. In some implementations, the software includes a feature that allows the user to select whether updates from a geolocation and status device are transmitted in real-time or on a scheduled or random basis.

The application may be used to manage features of a controlling device that utilizes a non-graphical information display, which may include various light emitting devices (e.g. LEDs), speakers, vibratory elements, and the like configured to provide appropriate information to a user. For instance, the software application may control use of dedicated arrows or meter-bars to indicate direction and/or proximity of the geolocation and status monitoring device. The application, e.g., software application, may manage operation of an audio component for producing sound in response to particular events. Such sounds and/or visual and/or vibratory notification signals may be generated and emitted from the controlling device and/or from the geolocation and/or status monitoring device.

The application executed by the controlling device may cause the controlling or geolocation device to emit sounds/visual/vibratory notifications, or may transmit a command or other notification-causing data to the location and status monitoring device for emission of such notifications by the location, control, and/or status monitoring device. Hence, in some instances, the software application may cause transmission of a command to the geolocation and/or status monitoring device to emit a sound/visual/vibratory notification in which the sound/notification content is previously stored at the geolocation and status monitoring device, or vice versa. On the other hand, the software application may cause the controlling device to transmit sound/notification content data to the geolocation and status monitoring device such that the location and status monitoring device may emit the notification transmitted. In this way, the sound/visual/tactile notification for a particular geolocation and status monitoring device may be customized according to user preference or circumstance.

In particular embodiments, such as where the controlling and/or geolocation device includes a graphical or LED display, the display may be integrated with a touch screen or may be distinct from user input mechanisms. The graphical display may be controlled to present any combination of at least location, proximity/direction, status, maps, etc. In various instances, the display may be a projection, such as where the device includes a camera and/or miniature projection mechanism. Location may be presented at least as a description and/or as a map showing geographic location. The location may appear as a predetermined identifier on a map. For example, a graphical representation of the personal effect (e.g., child or children or other objects to be tracked) may appear on a map to help distinguish and identify the personal effect for visual confirmation of location. When multiple personal effects are monitored, each personal effect may appear separately in the graphical representation.

Proximity/direction may be presented by showing both the user and the proximate device (e.g., geolocation and/or status monitoring device) on a map, by providing a textual description, and/or a graphic representation of distance. For instance, the proximity may be presented as a distance (e.g., 10" ft or "20 ft" or more), as a level meter, and/or as a color-coded indicator (e.g., blue=near, red=distant). Direction may be indicated via a map, or by direction indicators (e.g., arrows) showing where the user may go to get closer to the location and status monitoring device(s). In embodiments having multiple location and status monitoring devices the proximity and direction indicators may include identifiers for each geolocation and status monitoring device. For example, an arrow tagged with a preset or user-selected identifier may point in the direction of a particular personal effect. The size, shape, and or color of the arrow may provide information regarding distance to the child. Multiple children may have corresponding identifiers.

The software application may include a "library" of objects, e.g., children to be tracked, from which a user may select to monitor the various location and/or status. For instance, a user may according to circumstance choose to monitor one or several children, such as during a particular trip. In another circumstance, the user may choose to monitor a geolocation and status monitoring device associated with a different item, person, or pet. This permits the user to monitor the location and status of the person or pet, etc. having a geolocation and/or status monitoring device to monitor the location and status of a geolocation and/or status monitoring device associated with a child. The user may, further have the option of concurrently displaying information for all or a subset of monitored geolocation and status monitoring devices. In yet other instances, the user may be able to query a specified number of monitored geolocation devices from the library and confirm that all selected devices are within a specified range of the controlling device or within a specified range of a geolocation and/or within a specified predetermined status, etc.

The software and/or hardware application may include a screen that presents location and/or status in a historical manner. For instance, the application may cause display of past and present locations and/or health status over time, thus providing a route and/or condition of the monitored geolocation and/or health status monitoring device. Similarly, historical information may include status over time. For example, presenting the number of times that a child or animal enters or leaves a particular location, such as a list or map of locations and/or times at which the same took place. In geolocation and/or health status monitoring device implementations having an associated image capture device, such as a miniature camera, a list or map showing historic travels may selectably permit display of a photo or video captured during one or more of such openings. Moreover, historic data may include any combination of information collected over time. Thus, the historic data may include any combination of data collected over time, including at least location, proximity, altitude, pressure, battery level, health status, etc. The historic data may be presented in any (or any combination) of graphs, charts, maps, color contours, lists, text descriptions, tactile presentations, vibrations, braille, audio descriptions or notifications, etc. Those having skill in the art will recognize that patterns and trends in data may be analyzed and presented for further consideration.

The software application may also include a feature that communicates with a processor of a geolocation and/or health status monitoring device, e.g., master device, to update software or firmware stored in the location, control, and status monitoring wearable device. For instance, the software application may update firmware periodically, or in response to a user command. Firmware updating may include obtaining, e.g., by download, an updated firmware version, determining a software/firmware version currently in a geolocation and/or health status monitoring device, transmitting the update firmware if the firmware version is different from the obtained firmware version, and causing the location and status monitoring device to use the transmitted firmware version. The geolocation and/or health status monitoring device may be updated wirelessly or may in some implementations be configured for wired connection. Such wired connection may also be used for download of data to a computer and/or for charging a battery of the location and status monitoring device. See for instance FIGS. 5C-5E.

The software application may also be configured to monitor a software repository for an update version of the software application. Upon detecting an update version, the software application may prompt a user to update the software and/or may update immediately, such as upon identification that an update is available. Alternatively, the software application may be configured to receive a notification of an update version, the notification being pushed from a software repository when an update version is available. For instance, as processing power, transmission efficiency, and cellular signal configurations improve, the device firmware may be upgraded with revised and/or improved configurations and/or algorithms that are designed for allowing the device components to more effectively perform their functions and take advantages of all of the surrounding technological advantages. In particular, technological advancements that are directed to increasing connectivity over greater distances and prolonged periods of time may be communicated to the device and implemented in the device software and/or firmware, such as with respect to the threshold distance separating one device from the other.

In some instances, the predetermined threshold distance between the geolocation and/or health status monitoring device and the control device may be about 30 meters or less, about 20 meters or less, or even about 10 meters or less, such as about 8 meters or 7 or 6 meters, 5 meters, 3 meters, a foot or less. In other instances, the predetermined threshold distance can be about 10 meters more or less. In still other implementations, the predetermined threshold distance can be about 50 or about 40 or about 30 or about 20 or about 15 meters or more or less. In some implementations, a user-configurable threshold distance can be set by the user through a user interface or other input device associated with or otherwise in communication with the controlling device.

As an example, a control function device can include one or more of software-based (e.g. a touch screen, a voice activated control, a keyboard, a trackball, a mouse, a stylus, or the like) and/or hardware based (e.g. physical buttons or switches, etc.) controls that can allow variation of the user-configurable threshold distance. Such controls can allow a user to configure the user-configurable threshold distance directly in terms of a distance or indirectly in terms of some other criteria (e.g., by providing choices based on factors and/or a menu of options), which correlate to an actual threshold distance. In some instances, the threshold distance can be based upon the available communications technology (e.g., a functional range over which a reliable wireless communication link can be achieved between the controller and the personal effect), the importance of the personal effect to which the location and status monitoring device is attached, or the like.

In other instances, the threshold distance can be based in part on the environment around the personal effect, for example, a location of the child or animal or other object within a given area of a park, airport, or the like. For example, in some instances, a triggering device at a particular location can trigger the device, e.g., bracelet, on the child or animal to cause transmission of a signal to notify a user of the child or animal's or object's presence or departure. Depending on implementation, the signal may be sent from a beacon, relay, cellular tower, or scanning device or from the bracelet directly to a user's controlling device or to an enrollee-accessible webpage that is configured for such purpose.

In some examples, a user may wish to know a precise geolocation of a child or animal wearing a geolocation and/or health status bracelet, pendant, or other wearable. Consistent with one or more implementations of the current subject matter, the controlling device may receive data from a corresponding location and status device indicating such location. In such cases, the geolocation and/or status monitoring device may employ location sensors, receivers, or transceivers. Such location sensors can optionally include one or more technologies such as a Global Navigation Satellite System receiver (GNSS). Exemplary GNSS systems that enable accurate geolocation can include the Global Positioning System (GPS) in the United States, Globalnaya navigatsionnaya sputnikovaya sistema (GLONASS) in Russia, Galileo in the European Union, and BeiDou System (BDS) in China.

Wireless signals from any signal emitter having a known location may be received by the device and used for calculating and/or otherwise determining or pinpointing location. Of particular use are signals that themselves include location information or a unique identifier that can be indexed to a known location. For instance, alternatively or in addition to navigation satellite information, location sensors and/or beacons consistent with this disclosure can include cellular signals, radio frequency (RF), and/or microwave power sensors, such as heat-based (thermistor or thermocouple power sensors) or diode detector sensors. RF and microwave power sensors can allow radio frequency triangulation with respect to known-location transmitters such as cellular communication relay locations (e.g. cell towers), or other devices with known positions. Such signals, for non-limiting example, maybe based on the Institute of Electrical and Electronics Engineers' (IEEE) 802.11 standards (WiFi), IrDA (Infrared Data Association), ZigBee® (communications based upon IEEE 802 standard for personal area networks), Z-wave, wireless USB, or the like, and may include an identifier such as a Media Access Control (MAC) and/or Internet Protocol (IP) address of the transmitting device, or other typically unique identifier.

Other exemplary RF and microwave signal sources that may be used to track and/or locate the geolocation/status monitoring device for determining location or proximity include those used for aviation, such as radar systems (e.g. high power radar or ground control radar for aviation), VHF omnidirectional radio range (VOR) stations, microwave landing systems (MLS), instrument landing systems (ILS), automatic dependent surveillance-broadcast (ADS-B), and ground control radios. RF signals from radio and television stations, as well as wireless utility meters for electricity, gas, and water can also be used. Depending on the type and strength of the RF or microwave signal that is detected, one or more antennas may be built into the bracelet, pendant, or other wearable. In some instances, the one or more antennas can be provided on the exterior of the bracelet or other object or just under the outer layer of the bracelet; in certain instances, the one or more antennas form a decorative design on the exterior.

For instance, a geolocation/status monitoring device may receive signals from two or more transmitting devices, where the signals include an identifier for the transmitter (e.g., Media Access Control (MAC) address), from which an absolute location of the transmitter can be determined by lookup. Analysis of the two or more signals can then be performed to calculate a location of the geolocation/status monitoring device. In some such examples, a location and status monitoring device may include a processing unit that coordinates determination of the location of the device, such as using RF fingerprinting of one or more RF signal generators and/or antennas. The processing unit may also facilitate synchronization between a geolocation and/or status monitoring device and a controlling device.

RF fingerprinting of radio frequency or microwave signals from an RF source and/or antenna can allow for more accurate triangulation by accurately identifying RF or microwave emitting sources having known locations by characteristics of those signals. In some implementations, multiple sensors and/or antennas for multiple types of RF or microwave signals can be used to identify and triangulate an accurate location. Geolocation and/or health status can be correlated with an RF fingerprint of multiple RF or microwave sources, and known correlations of RF fingerprints and geolocations can be stored in a database. When RF or microwave signals from multiple sources are received by sensors on the bracelet, pendant, or other wearable, the RF fingerprint can be determined and compared with the database in order to determine the geolocation and/or health of the child.

RF signal analysis for proximity may include measurement of the received signal strength (or amplitude) of the radio signal. In some implementations, proximity of location and status monitoring device can be determined by reference to an object, such as another location and status monitoring device, beacon, or a third-party controlling device. For example, a BLUETOOTH® Smart signal from a location and/or health status monitoring device may be analyzed to detect an approximate distance and direction from a controlling, beacon, or other device. In another example, proximity may be obtained using Doppler principles. That is, a transceiver in the bracelet or other device may send a radio, cellular, or other signal from the bracelet to an object, e.g., a beacon or relay, having a known location.

In such an instance, the signal, e.g., radio, signal is then reflected from the object back to the transceiver or other antenna. The returning RF waveforms may be detected by matched-filtering, and delay in the return of the RF waveform is measured in order to determine distance from the object. In still another non-limiting implementation, a magnetic or electric field may be analyzed to detect disturbances in the field caused by movement of a relatively large dielectric object (such as a person or personal effect). Sensors can passively (and thus at low power) detect changes in spatial potential within the field and thus provide position, movement, and direction within the field.

Geolocation can also be determined by using inertial sensors (e.g. accelerometers and gyroscopes; see infra) either in addition to, or in place of GNSS, RF fingerprinting, or other location systems. If suitable RF or microwave or laser signals are not available or have insufficient strength for detection, information from inertial sensors associated with the bracelet disclosed herein can be used to calculate relative location using dead reckoning with respect to a previous location, or absolute location with respect to a last-known absolute location. For instance, an inertial sensor data on the current angular velocity and the current linear acceleration of a child or animal and/or their movements can be used to determine the angular velocity and inertial position of a bracelet, pendant, or other wearable having such sensors. In some implementations, inertial sensors may be combined with a compass associated with the bracelet to increase accuracy of direction calculations.

A user may wish to link or associate multiple geolocation and/o status monitoring devices (e.g., multiple persons) to the same controlling and/or monitoring device. A user may additionally wish to link or associate multiple geolocation and status monitoring devices to each other. In such scenarios, the user may designate one location and status monitoring device to be a dominant device that communicates to the controlling device, while the other location and status monitoring devices communicate to the dominant device. Such linkages may be unidirectional or bidirectional.

An example of this would be the use of a location and/or health status monitoring device, such as a bracelet or mobile phone paired therewith, designated by a user to be the dominant device. Accordingly, in such an instance, the one or more geolocation and/or health devices may each include a digital logic circuit board arrangement that further includes a pairing device such as for pairing the geolocation/monitoring device(s) with a remote master device such as via a wireless communication channel. In such an instance, the pairing may be defined by a distance between the geolocation device(s) and the master device such that if the distance between the geolocation device and the master device exceeds a predetermined range, an alarm is set off in one or more of the geolocation device and the master device.

Particularly, where multiple geolocation devices are to be tracked, such as via a master controller, the user may have synchronized the dominant device, e.g., child's mobile phone, with the controlling device, e.g., parent's mobile phone. The bracelet(s) may communicate its location and/or status information to the master device, e.g., phone, which in turn communicates this information along with its own location and status to the controlling device or may directly communicate the same to the master device. Such an approach can allow use of lower power communication devices (e.g., Bluetooth® Low Energy [BLE, a.k.a. Bluetooth® Smart], ANT+, RFID, IrDA, Zigbee®, etc.) on the location and/or health status monitoring devices other than the dominant device, which can optionally include a higher power communication device such as a cellular transceiver or WiFi transceiver for communication over longer distances. In this manner, the bracelet may communicate with a dominant device can communicate with the controller device over longer distances and can communicate with the other geolocation and status monitoring devices associated with a plurality of children. In some implementations, a wireless mesh network may be used to allow the geolocation and/or monitoring devices to route data and signals efficiently to and from the controlling or dominant device.

Synchronization or association of the controlling device with a geolocation and health status monitoring device or between two or more geolocation and status monitoring devices may include an exchange of electronic data. The exchange of electronic data may notify an associated device (e.g., controlling or monitoring device) of a unique identifier for each of the other devices, or may provide a code shared in common by all of the associated devices. A controlling device or primary location and status monitoring device may use unique identifiers to individually communicate with any or all of several associated location and status monitoring devices, and may obtain device-distinguishable data from each associated geolocation and/or health status monitoring device. On the other hand, when all devices share a common code for identification, the controlling device may treat a group of location and status monitoring devices as a single unit. In such implementations, a controlling device may learn of, e.g., proximity or location from any one of the associated geolocation and/or health status monitoring devices. This may be useful and efficient in instances where all of the associated location and status monitoring devices are typically considered together, such as a group of children.

Implementations consistent with this disclosure may combine the use of unique identifiers and common codes in order to make use of the advantages of both schemes. A common code may alternatively be used to uniquely secure communications between the controlling device and geolocation and/or health status monitoring device(s). For instance, the common code/password/key/token may be used as a part of an encryption scheme such as wireless access protocol (WAP), wired equivalent privacy (WEP), Wi-Fi Protected Access (WPA), variants thereof, or other standard or proprietary security protocols permitting secured communications. Such security protocols may implement cryptography algorithms such as advanced encryption standard (AES), data encryption standard (DES), RSA, and the like. In addition, communications may implement compression algorithms and/or hashing functions in order to reduce the amount of data transferred and to ensure data integrity. The encryption schemes may be implemented using dedicated circuitry, e.g., an integrated circuit, and/or general purpose processors, and may further utilize processors, magnetic and/or solid state memory devices, electronic fobs, electronic dongles, SIM cards and the like, or any combination thereof.

Figure 2A:
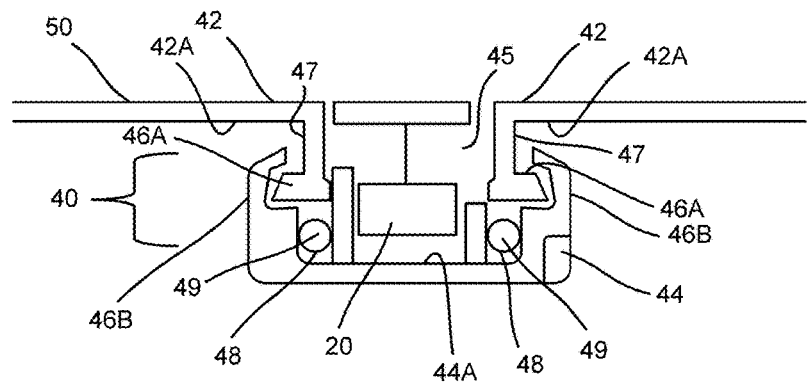
FIG. 2A is a cross-sectional view of an exemplary multi-part identity, geolocation, and/or health status monitoring apparatus of the disclosure, configured as a bracelet.
Figure 2B:
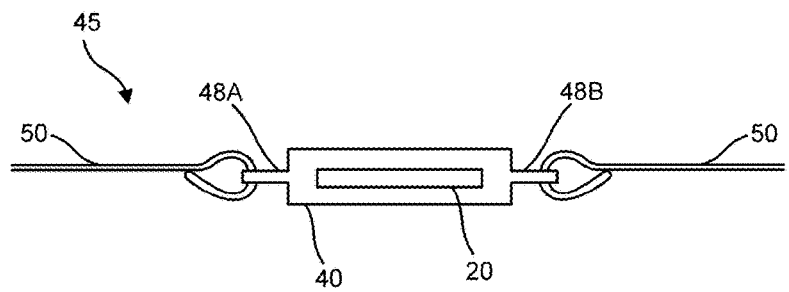
FIG. 2B is a side view of an exemplary identity, geolocation, and/or health status monitoring apparatus similar to FIG. 2A, but encased within a single material, configured as a multi-part bracelet.
Figure 2C:
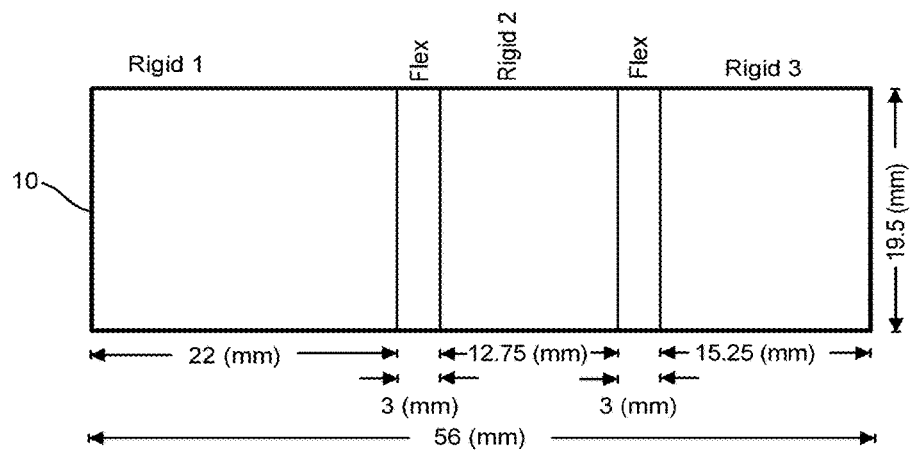
FIG. 2C is a top down view of an exemplary identity, geolocation, and/or health status monitoring apparatus, configured of as a bracelet.

As indicated above, and as can be seen with reference to FIGS. 2A-2C, in one aspect, the chipset 20 provided herein may be configured to function as a thin profile geolocation device for locating a person, animal, and/or object within a geographical region that is easy to use and simple to manufacture. In various instances, the device may further be configured to function as an identity, position, and/or health monitoring apparatus. In various instances, the chipset 20 has a thin profile, is lightweight, uses low energy, and may be curved, such as for ease of use, such as within the bounds of a curved piece of jewelry, such as a bracelet, for instance, a sports band.

Accordingly, with reference to FIGS. 2-5, such as FIG. 2A, the personal tracking and/or geolocation device may include an identity, position, and/or health monitoring chipset 20 that may be contained within a housing 40 that may be coupled with or otherwise configured for being removably attached to a secondary article 50, such as a necklace, bracelet, ring, keychain, or the like that may be worn by the user of the device 1. Hence, in various instances, the identity, position, and/or health monitoring chipset 20 may be included within a housing 40, which housing may include a single member having a first portion and a second portion that bends back on itself so as to encase the chip 20 between the first and second portions; or it may include a first member 42, e.g., a top member, and a second member 44, e.g., a bottom member, that when coupled together form the housing 40 within which the chipset 20 may be encased. In various instances, the housing may include a hinge member, which hinge member functions to moveably align the first and second portions, or separate top and bottom members, together in such a manner that the housing may be opened or closed, such as for insertion of the chipset 20 there between. In other instances, the top member 42 may be coupled to the bottom member, such as by being snapped together.

More particularly, the housing 40 may have a first portion or a first member 42, having a first (inner) surface 42A, and may further have a second portion or a second member 44, having a second (inner) surface 44A, such that when the first surface 42A is moved within closeable alignment with the second surface 44A, the first 42A and second 44A surfaces are separated from one another by a distance to form a chamber 45 there between, which chamber 45 is configured to securely retain the chipset 20 therein. In various instances, the housing 40 is of one piece, such as a one piece elastic band, that has been manufactured in a manner such that the chamber 45 is formed between a first portion 42A and a second portion 42B of the elastic band 40, the chip 20 is inserted therein, and the insertion opening is closed thereby permanently coupling the chipset 20 within the bounds of the band 40. In other instances, the housing 40 is a separate unit from a secondary article 50 to which the housing 40 may be removably coupled. In such an instance, the housing 40 may include retaining features 48A and 48B that function to allow the housing 40 to be coupled to the secondary article 45.

For instance, retaining features, e.g., attachment openings, 48A and 48B may be any feature configured for allowing the housing 40 to be coupled, such as permanently or removably coupled to a secondary article 40. Particularly, where the secondary article is a necklace or bracelet, a single or multiple retaining features 48 may be included as part of the housing 40, where the retaining feature 48 may be one or more loops or openings through which the necklace or bracelet 50 is threaded. In other embodiments, one or more of the retaining features 48 may be configured to be at least part of a buckle, a button, a zipper, a fastener, such as hook and loop fastener, a pin and loop fastener, a clip, or the like. In various instances, the retaining feature may be or otherwise include an adhesive.

Figure 5A:
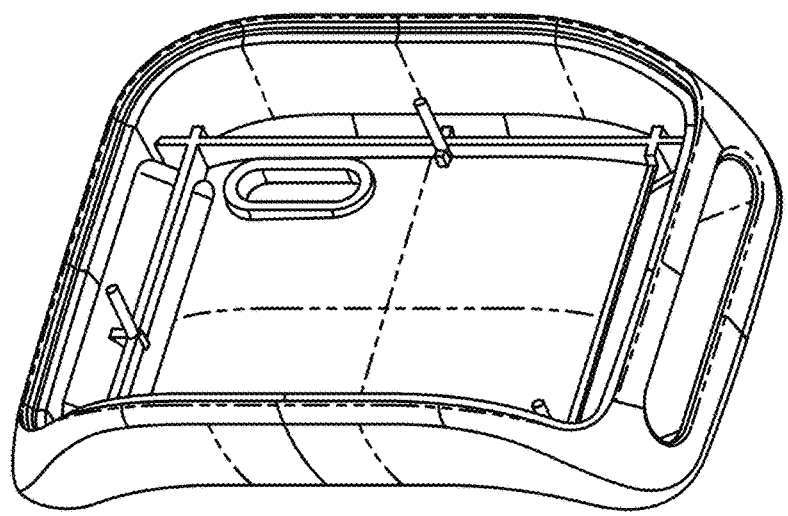
FIG. 5A presents a top down view of an interior of the housing for the identity, geolocation, and/or health status monitoring apparatus of the disclosure, such as where the housing has a depth of about 20 mm of less, such as 15 mm or less, for instance, 11 or 10 mm or less, or even 8 mm or less.
Figure 5B:
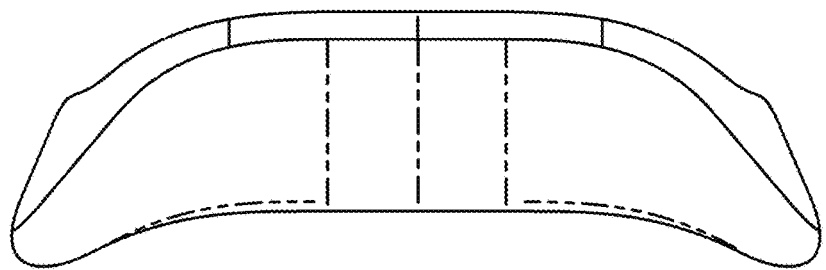
FIG. 5B presents a side view of the housing of FIG. 5A.
Figure 5C:
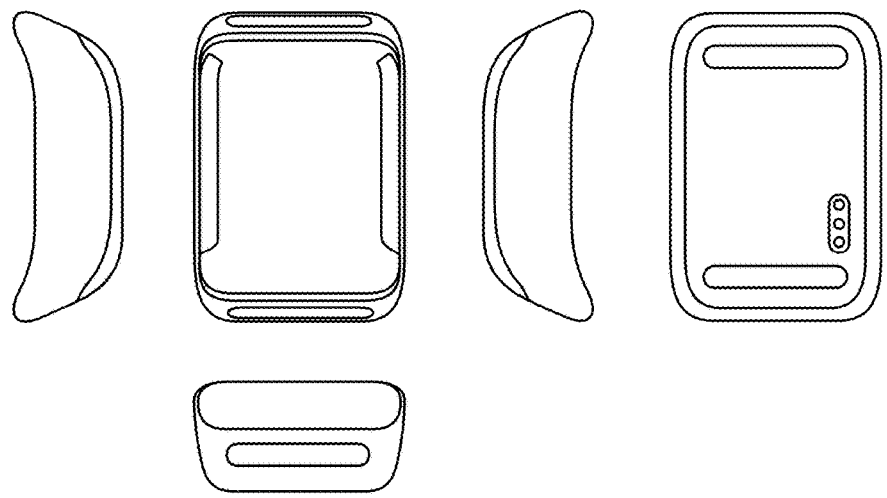
FIG. 5C presents different perspective views of the housing of FIG. 5A.
Figure 5D:
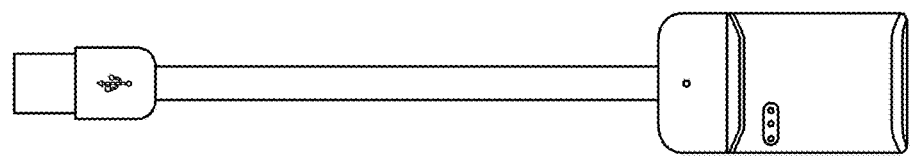
FIG. 5D presents a top-down view of a charger of the identity, geolocation, and/or health status monitoring apparatus of the disclosure.

In various instances, such as can be seen with respect to FIGS. 5A-5C, the housing 40 may be a waterproof housing. For instance, a portion or the entire PCB, RF antennas, chipset, including GPS and/or SIM, charging coil or antennas, and/or battery may be encased in a durable and/or waterproof material, such as by being molded, e.g., injection molded, therewith. Particularly, the PCB and internal componentry may be held in place by a small plastic wireframe piece while the case material may be molded around the entire assembly. In certain instances, the telephone chipset may be omitted, such as in favor of Bluetooth or other wireless, e.g., cellular, communications modules, because of it's added bulkiness. In other instances, one or more of these components may be included together on the chipset.

For instance, in certain embodiments, as indicated, the tracking, e.g., geolocation, and/or health status and monitoring device may be configured for performing a variety of communications. And as such, the device may be configured for connecting to a suitably configured communications network. A communications network may be any type of network for conducting remote communication between two devices, such as a cellular network, e.g., LTE cellular network, for instance, a GSM, CDMA, EDGE, WiMAX network, and the like. The cellular network may provide GPRS and/or SMS data services between a plurality of tracking and/or communication devices and/or a central server, a monitoring center, and/or a streaming audio, video, or other content provider.

For example, a monitoring and/or tracking device of the system may be connected to a paired, e.g., master, device, monitoring center, and/or streaming service provider through a web interface, such as over a home network, WIFI hotspot, or similar connection when such networks are accessible. In particular instances, the monitoring and/or tracking device may be communicably coupled to another such device through any suitable communication link, such as Bluetooth, Low energy Bluetooth, Zigby, and the like).

Particularly, the tracking and/or monitoring device may include a processor(s) and/or a cellular communications card, such as a subscriber identity card, or SIM card, that functions to provide and/or otherwise store cellular communications data, such as for providing cellular communications capabilities to the device. The device may also be configured to share a SIM card, or cellular capabilities with another device, such as a paired master controller, e.g., a cellular telephone. The cellular communications card may be configured for global system for mobile (GSM) communications. In such an instance, data may be digitally encoded prior to transmission, and in certain instances, the data may be split such as between 800 MHz, e.g., 824.04 MHz, and 900 MHz, e.g., 893.7 MHz, such as in accordance with a time-division multiple access (TDMA) wireless network protocol, and/or may be transmitted using a code-division multiple access (CDMA) wireless communications protocol, such as over a 2G, 3G, 4G, or 5G network, such as where the data may be multiplexed in such a manner that numerous signals may occupy a single transmission channel, such as for including one or more of location, cellular, and text data, for instance, such as at an ultra-high frequency, e.g., between 800 MHz and 1.9 GHz.

In particular instances, the cellular communications module may be configured for performing an analog to digital conversion of the communications data, such as where an audio input is first digitized into binary elements, prior to transmission, and then transmitted according to a defined code or pattern. Likewise, the receiving, e.g., paired communications device, e.g., master controller, may be configured for receiving and interpreting the signal, such as where its frequency response is programmed with the same code in a manner such that it may be followed along with the transmitter frequency. Accordingly, the processor of the health monitoring and/or tracking device may be communicably connected to a communications link, such as via a 3G or 4G or 4G/IMT, or even a 5G cellular internet connection, through which communications link various cellular communications may be provided.

Specifically, the processor may include programming that may be implemented in a wired and/or software based configuration so as to implement the cellular capabilities of the tracking and/or monitoring device, such as through a suitably configured wireless cellular transceiver and/or antenna. More specifically, the monitoring and/or tracking device may include electronics and a short and/or long-range wireless transceiver and associated antenna, which allow for short, medium, and/or long-range wireless voice communication, and data communications with peripheral devices, such as a master device or remote server. For instance, the antenna may be configured to transceive analog and/or digital signals.

For example, in particular embodiments, the processor may be programmed to pass through voice, text, and/or video communications received by the cellular transceiver to a voice-capable peripheral when such a peripheral is employed when communications on the companion device and are activated. Data received and/or generated by the device may be stored by the processor, such as in the memory, which can be non-volatile memory such as serial flash memory until required by the processor or until it is to be transmitted by the device. Particularly, the tracking and/or health monitoring device may be configured for tracking and/or monitoring a person, animal, or object, which may be configured as a bracelet, pendant, or watch, and as such, the watch and/or bracelet and/or pendant may include a transmitter adapted for sending communication, such as information in the form of data or pulses, e.g., pulses of known duration and intensity, a receiver, and one or more antennas to assist in the transmitting and receiving of data to and/or from a remote transmitter. In various instances, the receiver and the transmitter may have synchronized clocks to determine signal propagation time and distance. The device may also include an alarm that may be generated if a determined distance between the device and/or the status being tracked and/or monitored exceeds a preset value from the device, e.g., a paired device, such as a master control device, tracking and/or monitoring the tracked device.

In various embodiments, the wireless transceiver may be designed and implemented using any wireless communication standards such as Bluetooth, 802.11, Low Energy Bluetooth protocols, and the like. Hence, when a call or text is received over the suitably configured communications link, the processor directs audio/video/data to an output such as a speaker element, for listening/viewing/reading purposes, and may receive input from a user of the device speaking into a microphone element. Consequently, the processor may direct audio/video data obtained from the speaker/microphone to the communications link for transmission to its companion, e.g., paired, master device.

Particularly, in various embodiments, the cellular transceiver may be of the GSM/GPRS variety, and/or may include a SIM card. In such instances, the cellular transceiver may be configured to allow one-way or two-way voice, video, and/or data communication between the tracking and/or health monitoring device and the remote server and/or a master controller. Voice and/or video communications are further enabled by a direct connection between the cellular transceiver and an audio and/or visual codec, which encodes and decodes the digital audio/visual signal portion of the wireless transmission, and an associated speaker and/or microphone. Data communications may use a cellular data channel and/or a cellular control channel, which may make use of short message service (SMS) capabilities in the network. This configuration has benefits in that it provides redundancy for cellular systems for which service for both types of data communication is supported.

Likewise, the health monitoring and/or tracking device may include a GPS receiver (and associated antenna(s)) to receive signals transmitted by various GPS satellites. In such instances, the signal may be used to establish a geographical location of the device, and therefore, the person being monitored. For instance, in one embodiment, data from the GPS receiver is passed to the processor 401, which in turn processes the data to determine a location and associated time, and stores it in a memory, such as a serial flash memory pending transmission using cellular transceiver. Particularly, a GPS engine may be included wherein the GPS engine includes both a GPS receiver and the capability to process the GPS signal to produce a location determination and associated time indication. Using a stand-alone GPS engine frees processing bandwidth in the processor, thereby allowing the processor to perform other additional functions.

In some embodiments, the cellular transceiver may also be used to geographically locate the device such as through cell tower triangulation, or may be used to provide location information used in assisted GPS schemes. In particular embodiments, geographical location using cellular transceiver may be performed in addition to, or as substitution for the GPS receiver. In various embodiments, the tracking may involve a combination of a GPS positioning satellite system, e.g., beacon, a GPS receiver and transmitter with antenna, and a modern 3G or 4G or 5G, etc. internet protocol system with cellular network position tracking capabilities, such as to provide both two-way communication and tracking capabilities.

For instance, an individual's location may be determined via GPS data from a GPS Satellite sent to the GPS generator of the tracking device on the person being wearing the monitoring and tracking device. A second way of determining the location may be by tracking the device with 3G or 4G, etc. mobile communications and triangulation from multiple cellular, PCS, or mobile phone service transmitting towers. Either or both of these can be used together, in order to provide a more thorough and complete coverage of the device and wearer's location. For example, this may provide improved location capability in areas such as within buildings where GPS satellite coverage is not sufficient to provide useful location information, whereas the 3G or 4G or 5G mobile communication triangulation may be used to determine the wearer's position.

Specifically, in various embodiments, the receiver may be configured to integrate signals from one or more antennas, such as by using a CDMA or other detection protocol. For instance, in various instances, the antenna may be configured to transceive extremely low frequency signals, such as location signals, for example, ultrasound signals, such as for determining distance. Particularly, a distance measurement may be accomplished by an active communication between the paired units. In various embodiments, the transmitter and receiver can be an 802.11 transmitter and receiver, a Bluetooth or LE Bluetooth transmitter and receiver, and the like. Likewise, the network can be one of a local area network (LAN) and a wide area network (WAN), as well as a 802.11 network, a Bluetooth network, and a cellular network.

In various instances, the case material may be a Thermoplastic Elastomer (TPE), such as with a relatively low melting point, so as to prevent overheating the battery and electronics during assembly, while making the unit waterproof. In some instances, the housing material may be a rubber or plastic, such as a polypropylene or polycarbonate. In these and in other instances, the housing 40 may include a top portion or member 42, and a bottom portion or member 44 that when coupled together form a liquid proof, e.g., a waterproof, seal there between. In some instances, one housing member 42 may include a channel, such as a circumferential channel 48, and the other housing member may include an impingement member 47, such as for insertion into the channel. Such a configuration may assist in waterproofing the encasement. In certain instances, a sealing member 49 may be included, such as a compressible member or O-ring. FIG. 5A, for instance, presents a top-down view of a bottom encasement member to which a curved planar top encasing member may be attached, and FIG. 5B shows a side view with the top attached. FIG. 5C presents a plurality of perspective views of tops, bottoms, and side views. A suitably configured clasping mechanism is exemplified in FIG. 2A.

For example, as can be seen with respect to FIG. 2A, the top member 42 may have an impingement member 47, which in some instances, may have a clasping element, e.g., tooth, 46A associated therewith. Likewise, the bottom member 44 may include a channel 48 for receiving the impingement member 47, and may have a complementary groove 46B for receiving the clasping element 46A therein. The channel 48 of the bottom member 44 may include a plurality of wall members 44. The inner walls may bound the chamber 45, which in turn is configured for retaining the chipset 20.

Particularly, as exemplified in FIG. 2A, the bottom member 44 includes a channel 48. The channel includes an interior bounding member 46A and an exterior bounding member 46B, which bounding members form walls extending upwards, e.g., inwardly, from the second inner surface 44A of the bottom member 44, and which walls are separated one from the other by a distance that defines the width of the channel 48. The channel additionally includes a sealing member 49, such as a gasket, to seal the interior of the cavity from the exterior of the cavity. In this configuration, the top member 42 includes an impingement member or wall 47 that extends downwards, e.g., inwardly, away from the first inner surface 42A, and is configured for compressing against the gasket 49, thereby sealing the channel from the ingress of water, or other liquid, when the top member 42 is associated with the bottom member 44 and coupled together by the clasping mechanism 46. In this embodiment, the clasping mechanism 46A is associated with the impingement member 47, and its corresponding clasping member 46B, e.g., groove, is associated with the exterior bounding member 48B.

For example, the clasping or latching mechanism 46A is configured as a lip or tongue that at least partially or fully circumscribes the perimeter of the impingement member 47, and the clasping or latching mechanism 46B is configured as a groove that at least partially or fully circumscribes the perimeter of the bounding member 48, and is adapted to receive the lip 46A. In this manner, the impingement member and interior bounding members bound the chamber, and a circumferential seal may be established between the top 42 and bottom 44 members when they are coupled together, such by the lip 46A being received within the groove 46B. In other embodiments, the clasping mechanism need not be an internal clasping mechanism, but rather may be an exterior clasping mechanism such as a buckle or latch part of which is on the top member and the other part of which is on the bottom member. It is noted, that although various configurations have been set forth with respect to the above disclosure, these various configurations are not binding an can be interchanged among the various members and their component parts without departing from the scope of the disclosure. For instance, the impingement member 47 and the channel 48 may be positioned on the opposite, e.g., bottom and top, members. In a manner such as this, the circuit board 10, or chip 20, etc. may be positioned within the cavity 45 and be retained therein in a waterproof environment. Additionally, an adhesive may also be used to seal the top member 42 against the bottom member 44 to effectuate or at least participate in the effectuation of a strong sealing between the two members.

Additionally, as can be seen with respect to FIG. 2B, the housing 40, which may be attachable to or integrally a part of a secondary article, such as a bracelet or band 40, may include an external clasping mechanism 46. The clasping mechanism 46 may include a first portion 46A, e.g., associated with the top portion of member 42 of the housing, and may further include a second portion 46B, e.g., associated with the bottom portion or member 44, together the clasping mechanism portions 46A and 46B correspond with one another such that when operably associated with one another function to couple the top 42 and bottom 44 members together. Any suitable clasping mechanism can be employed for this purpose, but in some embodiments, may be a lip and groove, a tooth and opening, a buckle, a clip, and the like.

As can be seen with respect to FIG. 2C, in particular instances, the identity, position, and/or health monitoring apparatus 1 may include a circuit board 10 containing the above referenced micro-processing, GPS, SIM, and/or other functionality, which apparatus 1 may be configured so as to be worn by a user, such as a child whose location is to be monitored and/or tracked, and, thus, in various embodiments, the circuit board 10, or chip 20 containing the same, may be configured so as to be part of, or otherwise coupled with, a piece of adornment, such as a piece of jewelry, a piece of clothing, a key chain, collar, and the like. For instance, as seen in FIG. 2C, in various instances, the printed circuit board (PCB) may be made of a rigid, semi-rigid, semi-flexible, flexible material or a combination of the same. In certain instances, the PCB may be a combination of rigid 10a and flexible 10b materials, such as having three rigid sections separated by two flexible sections, so as to allow the micro-components to be securely mounted on the rigid sections, while allowing the flexible sections to flex so that the overall board may be able to bend, and/or otherwise twist, stretch, or to curve such as to bend and/or conform to the wrists of a wearer of the band, such as a small child.

In various embodiments, the rigid sections 10a may range from about 5 mm to about 50 mm, such as about 10 mm or 12.75 mm to about 40 mm, such as about 15 mm or 15.25 mm to about 35 mm, such as about 20 mm or 22 mm to about 30 mm, including about 25 mm in length, e.g., per section. Likewise, the flexible sections may be from about 1 mm to about 20 mm, such as about 2 mm to about 15 mm, such as about 3 mm to about 10 mm, such as about 5 mm to about 7 mm in length, e.g., per section. In certain instances, the width may range from such as about 10 mm or 12.75 mm to about 40 mm, such as about 15 mm or 15.25 mm to about 35 mm, such as about 19 or 19.5 or even 20 mm or 22 mm to about 30 mm, including about 25 mm in width. In particular instances, the entire length may be from about 25 mm to about 100 mm, such as 30 mm to about 90 mm, such as about 40 mm to about 80 mm, such as about 50 mm to about 70 mm, including about 55 or 56 mm to about 60 mm in length.

Particularly, the substrate 7 may be composed of one or more layers, such as conductive layers, e.g., of metal portions such as copper, that have been layered on top of an insulating layer, such as an insulating layer made of a glass epoxy. In various embodiments, the circuit board may include a top layer (GTL), such as a layer including the components and/or signal emitters of the device, a middle layer, such as a ground plane (G1) and/or a power/signal layer (G2), and/or a bottom layer (GBL) that may include one or more various system components, and the like. One or more of the layers may include a metal mask with one or more vias, such as a copper layer, e.g., about a half-ounce or 0.7 mls, and/or one of the layers may include a silkscreen or other non-conductive layer. In various instances, the entire PCB area may include a 2 layer flex PCB with rigid sections that may include an additional top and/or bottom layer that is rigid and/or which may be configured so as to contain the various components of the device, such as the electrical components. Hence, the rigid sections may include 4 layers, and in some instances, the signals between the rigid sections may be routed using one or more of the two or more flexible layers.

Figure 2D:
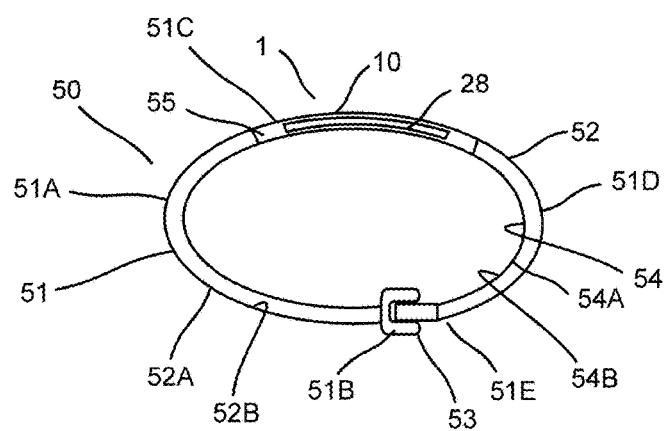
FIG. 2D is a side view of another exemplary identity, geolocation, and/or health status monitoring apparatus similar to FIG. 2B, but molded within a single material.

Further, as can be seen with respect to FIG. 2B, in various embodiments, the monitoring apparatus may be a part of a piece of jewelry, such as a necklace, a wrist bracelet, a ring (e.g., an ear, finger, belly, toe, ring and the like), an ankle bracelet, and the like. For example, as depicted in FIG. 2D, the identity, position, and/or health monitoring apparatus 1 is part of a bracelet 50. Particularly, in some embodiments, the monitoring apparatus may be a piece of adornment, such as bracelet 50. The bracelet 50 may include an identity, position, and/or health monitoring apparatus 1, as described above. The monitoring apparatus 1 may be a separate unit from the bracelet 1, which may be coupled with or otherwise attached to the bracelet 1, such as through an appropriately configured retaining element, or the monitoring apparatus 1 may be contained within the bounds of the bracelet 1. For instance, the bracelet 1 may include a first surface 52 and a second surface 54, which first and second surfaces are separated by a distance sufficient to allow the monitoring apparatus 1 to be retained there between. In various embodiments, the first or second surfaces may be the substrate upon which the electronic circuitry is printed. Particularly, the bracelet 50 may be composed of an elongated body member 51 having a proximal portion 51A and a distal portion 51D, which proximal and distal portions are separated one from the other by a medial portion 51C.

The bracelet 50 may be formed as a continuous loop and thus the proximal, medial, and distal portions may merge into one another, and thus definable only with reference to a secondary object, such as the identity, position, and/or health monitoring apparatus 1 that is associated with the bracelet 1. In other instances, the bracelet 50 may include a proximal end 51B and a distal end 51E, which proximal and distal ends may include corresponding clasping mechanisms 53 allowing both ends to be coupled to one another, such as around the wrist of a wearer of the bracelet 50. This clasping mechanism, along with all the other clasping mechanisms set forth herein may be any suitable clasping mechanism allowing the two separate portions to be joined together, so as to be capable of being joined, disjoined, and/or rejoined with one another. For example, the clasping mechanism may be a buckle, button, fastener, such as a hook and loop fastener, a pin and loop fastener, a tongue and groove fastener, a latch fastener, a clip, a tie, a screw with corresponding screw threads, a cam, and/or any other coupling mechanism sufficient for joining the proximal and distal ends together.

As indicated above, the bracelet 50 may form the housing 40 within which the monitoring device 1 is retained. Accordingly, the bracelet 50 may be configured so as to include a chamber 55 within which the monitoring device may be received. Particularly, the bracelet 50 may have a first surface 52 and a second surface 54, where the first surface 52 includes an exterior surface portion 52B and an interior surface portion 52A, and the second surface 54 includes an exterior surface portion 54B and an interior surface portion 54A. The interior surface portion 52A of the first surface 52 and the interior surface portion 54A of the second surface 54 may be separated from one another by a distance, which distance defines the expanse of the chamber 55 into which the monitoring device may be positioned. The monitoring device 1 may be inserted into the opening of the chamber 55 by various manners, such as by being comolded therewith.

As can be seen with respect to FIG. 2D, the bracelet 50 to which the monitoring device 1 is to be coupled is curved. Accordingly, in various embodiments, the printed circuit board 10 and/or the chip 20 that includes the monitoring functionality may also be curved. For instance, both the bracelet 50 and the substrate 7, e.g., the circuit board 10 or chip 20, may have a curve, such as a curve that corresponds to one another. Particularly, the bracelet 50 may have a curve that has an arc, such as an arc that ranges from 30 degrees to 360 degrees, and likewise the substrate 7 may also have a curve that has an arc, such as an arc that correspondingly ranges from 30 degrees to 360 degrees.

Additionally, in various embodiments, the identity, position, and/or health monitoring device 1 may be designed to have a thin profile. As such the bracelet, and/or the circuit board 10 containing the micro-processing function itself, may have an overall thickness that ranges from about 3 mm to about 30 mm, for instance from about 5 mm to about 25 mm, including about 8 mm to about 20 mm, such as up to about 10 mm or 15 mm and in some instances may be about 12 mm thick. In certain embodiments, the identity, position, and/or health monitoring apparatus 1 may include and/or may otherwise be coupled to an input/output module, one or more displays, and/or one or more sensors. In various instances, the circuit board may be a rigid or semi-flexible digital logic circuit board.

For instance, as can be seen with respect to FIG. 1A, the identity, position, and/or health monitoring apparatus 1 may include an input device that is operably coupled therewith. In such an instance, input, such as input from a user, or a person associated with the user, may be received in any form, including, but not limited to, acoustic, speech, or tactile input. Accordingly, a typical input device may include, but is not limited to, keyboards, touch screens or other touch-sensitive devices such as single or multi-point resistive or capacitive trackpads, voice recognition hardware and software, optical scanners, optical pointers, digital image capture devices and associated interpretation software, a Universal Serial Bus (USB) port, Secure Digital Input Output (SD/SDIO) port, flash drive port, lightning port, and the like. Additionally, the identity, position, and/or health monitoring apparatus 1 may include a display that is operably coupled therewith, which display may function as a typical output for the monitoring apparatus. A typical display may be any suitable display such as those that are similar to a smart phone or tablet computing retina display.

Figure 5E:
FIG. 5E presents a side view of the charging apparatus of FIG. 5D.

More particularly, as can be seen with respect to FIG. 5A, the housing member 40, in this instance the bottom member 44, includes an input and/or charge port 56. The charge port 56 may be of any shape, size, and/or configuration so as to receive an input and/or charge mechanism, such as a suitably configured input and/or charging device such as presented at FIGS. 5D and 5E. For instance, as can be seen with respect to FIG. 5D, a top down view of a suitably configured input and charging device 60 is provided. The charging device 2 includes an elongated member 57 having a proximal portion 57A and a distal portion 57B, the proximal end including an input, such as a male end plug portion, which in this instance is configured as a USB 58A, but may also have other suitable configurations, such as a two or three pronged electrical plug configuration. The elongated body 57 includes wiring for transmitting energy as well as data to thereby couple the geolocation and/or health status monitoring device 1 to a source of energy and/or data transmission. The distal portion including a receptacle for receiving the geolocation device 1 and including a charge relay 58B for being inserted through the housing and into the charge port 56 to thereby interface with the device, charge the same, and/or for the transference of data to and/or from the device 1. FIG. 5E presents a side view of the charge device 2 of FIG. 5D.

Figure 3:
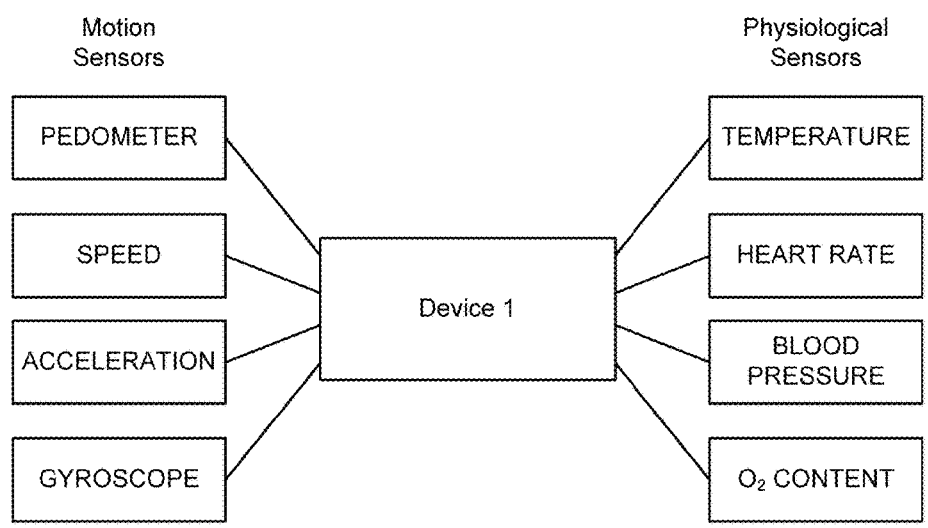
FIG. 3 is a diagram of various sensors that may be employed in conjunction with an exemplary identity, geolocation, and/or health status monitoring apparatus of the disclosure.

Additionally, as can be seen with respect to FIG. 3, in various instances, an identity, position, and/or health monitoring apparatus 1 of the present disclosure may include a sensing mechanism such as a sensor. A typical sensor may be any form of data collection mechanism capable of detecting a relevant characteristic, such as of a user or an environment of a user, and may be configured for transmitting that data to the microprocessor unit for processing and/or transmission and/or display such as to the user or an other third party, for instance, a parent, guardian, or medical personnel charged with taking care of the wearer of the circuit board.

For instance, in certain instances, the sensor may be a motion and/or orientation sensor, such as a distance measuring sensor, such as a pedometer, a speed or velocity measuring sensor, including an accelerometer, for example, a multi-axis accelerometer, a gyroscope, strain gauge, and/or a piezoelectric sensor, optical sensor, thermal and/or energy sensor, and the like. In various instances, the motion sensor may include sensors that detect instantaneous motion and/or sensors that detect velocity and the like for measurement of short duration movements or impulses. In further instances, the motion sensor may be one or more sensors that detect distance, speed, and/or velocity and the microprocessor, and/or the sensor hardware or software itself, may be configured to utilize that information about distances, passage of distance in relation to the passage of time, and/or the rate of such change so as to determine one or more other characteristics about motion, direction, and/or location. For example, information from such pedometers, distance, velocity, acceleration, orientation, and/or other inertial sensors associated with the monitoring apparatus can be used to calculate relative location, such as using dead reckoning with respect to a previous location, or absolute location with respect to a last-known absolute location. In such an instance, inertial sensor data on the current angular velocity and the current linear acceleration of an object may be used to determine the angular velocity and inertial position of a device having such sensors. In some implementations, inertial sensors may be combined with a compass associated with the device to increase accuracy of direction calculations.

Accordingly, the various sensors or data from such sensors may be used in combination to determine other relevant information. For example, examples of such sensor combinations can include a distance sensor, such as a pedometer, e.g., a calibrated pedometer, an altimeter, and/or a clock, or watch, a stopwatch, a timer, and/or a pendulum, from which data speed and/or acceleration may be determined. Impulse data may also be used in such a calculation, and hence, such sensor combinations could also include accelerometers, including multi-axis accelerometers, gyroscopes, and the like. Such accelerometers and/or gyroscopes may be MEMS-based, nano-scale based, piezoelectric, piezoresistive, and the like.

Other distance sensors can include a GPS receiver or other sensors that utilize wireless signals to determine position, relative location, and direction, such as cell phone tower signals, which used with a suitable device, and the like. Sensors that detect distance from a fixed object through electromagnetic detection, optical detection, sonic detection, and the like, may also be employed. Combining these position sensors with a time marking sensor, such as a clock or timer or stopwatch, or the like, can help a monitoring entity observe how movements of the user vary over a single movement or sequence of movements, or over a period of time such as over an event that may last days, weeks, or months. In certain instances, one or more internal or external sensors may be employed such as where the configuration of the sensors may be placed so as to indicate the position of a person, animal, or object, and possibly relative position of limbs or portions of the person's body, may be useful in determining and/or monitoring vectors related to the direction of movement. Hence, in various instances, various sensors may be internal to the device and/or worn, and/or external to the device and/or worn for the determination of location, position, orientation, motion, direction, as well as speed, acceleration, as will as ascent and decent and the rate of change in such motions and/or directions.

In various embodiments, one or more of the included internal or external sensors may be configured so as to be a physiological data collector that may be configured so as to collect physiological data, such as data associated with a person, e.g., child or adult, and/or his or her state of health and/or performance in an activity, such as an activity requiring mental or physical exertion. For example, the sensor may be a physiologic sensor, such as a temperature gauge or thermometer, so as to measure the temperature of the user and/or his environment; a heart monitor, so as to measure the heart rate of the user; a blood pressure monitor, to measure the users blood pressure; a blood glucose monitor, to measure blood glucose of the user; as well as one or more sensors for sensing and/or determining one or more of: ambient or body temperature; heart rate; activity (steps, elevation); bodily chemical composition, e.g., glucose, insulin, cholesterol, steroids, Hormone levels, etc.; air pressure; blood pressure; blood O2/CO2 level; humidity; magnetometer or form of compass; accelerometer; gyroscope; proximity; light level; carbon monoxide; smoke/particulates; Personal Lightning Detector (EMP); and the like.

Accordingly, in various embodiments, an identity, position, and/or health monitoring apparatus is provided wherein the device includes an integrated circuit, such as an FPGA, ASIC, CPU, or the like, such as a micro-controller or microprocessor, such as a 32 bit Ultra-Low Power ARM Cortex or Intel Cortex. The microprocessor may include a memory or may be otherwise operably connected to a memory, such as various low power serial NAND flash ICs. Additionally, the microprocessor may include a communications module that includes a transmitter and or a receiver, and/or may be operably coupled to the same. In various embodiments, the microprocessor may include or may otherwise be coupled to one or more sensors, such as one or more sensors related to determining geo-location, relative motion and/or direction, one or more health related conditions, as well as one or more characteristics of movement, such as speed, acceleration, and the like.

In such an instance, the integrated circuit, e.g., microprocessor may be configured so as to be operably coupled with one or more sensors, receivers, and/or transmitters for the purpose of better determining and/or communication such data. For instance, as described in greater detail herein below, in various instances, the microprocessor may be coupled to a receiver and/or other sensor that is configured for receiving a GPS or cellular signal so as to determine a position, location, and/or motion, and may further be coupled to a transmitter for transmitting data related to a determined position, location, and/or motion, such as over a radio frequency, or a cellular network, to a third party for the monitoring of the same. For example, the microprocessor may be coupled to a radio transmitter configured for transmitting data, such as over an operating range from about 2.4 to about 2.485 GHz frequency. In certain particular embodiments, the transmitter may include one or more of WIFI, Bluetooth®, Low Energy/Smart (BLE), ANT+, RFID, IrDA, Zigbee®, and the like.

Figure 4:
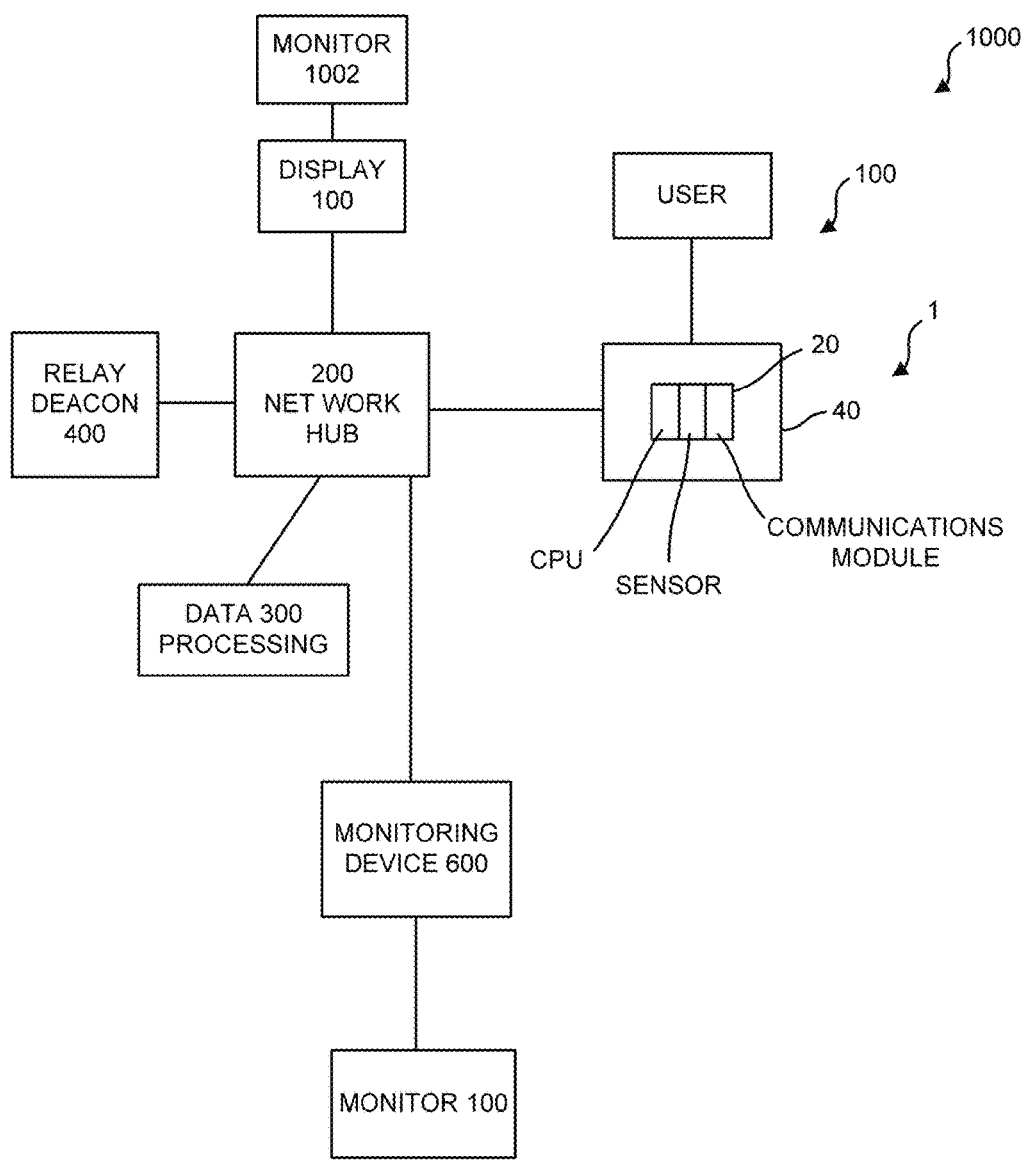
FIG. 4 is a diagram of an exemplary system employing the exemplary identity, geolocation, and/or health status monitoring apparatus of the disclosure.

As can be seen with respect to FIG. 4, in another aspect, a system for determining and/or displaying information about a user, his or her position and/or location, and/or a state of his or her condition of health is provided. In various implementations, the system 1000 may include one or more of an identity, position, and/or health monitoring apparatus 1, as described above, a user 100 of the system 1000, such as a person to carry or otherwise be coupled with the monitoring apparatus 1, and may include a network 200, a data processing server unit 300, one or more external sensors 400, one or more external relays, or beacons 500, and/or one or more second or third party monitoring devices 600 such as a second or third party computing devices, such as a desk or laptop computing device, having a display, and/or a mobile computing device, such as a tablet, mini-tablet, of mobile cellular phone based or other handheld computing device.

Accordingly, in various embodiments, the system 1000 may include an identity, position, and/or health monitoring apparatus 1, such as that described above, which may include one or more of a microprocessor, a memory, a communications module, an input/output port, a battery, and/or one or more internal and/or external sensors. In such an instance, the monitoring device 1 may be contained within a housing, such as within the bounds of a bracelet, ring, keychain, or the like, as described above, which may be worn, such as by a child, adult, or other animal or object 100 the tracking of which may be desired, such as by a parent or health monitoring agency 1001 wanting to ensure the safety of the child, animal, and/or object 100. In particular, the device 1 may include a display mechanism and may be configured so as to function at least in part to display the identity of the user and/or a condition of the users health. As indicated, in various instances, the device 1 may contain a communications module that not only includes a receiver, such as a GPS receiver, such as for determining the location of the device and/or or a person, animal, or object associated with the device, but also may include a transmitter, such as for transmitting such position and other data over a network 200 to a suitably networked receiving device 600, such as a third party tracking and/or monitoring device, such as a computer.

Consequently, the system 1000 may be configured to track and/or monitor the user 100, such as a child, and/or the condition of the user and/or his environment, and communicating that information to a second party 1001, such as a parent of the child, or other third party 1002, such as a health care professional or government agency interested in monitoring and/or tracking the user. Hence, in such instances the monitoring device 1 of system may include a transmitting device configured for transmitting data about the user, his or her location, position, movement, and/or condition, and/or environment to a receiver, such as a computing device 600 that is suitably configured for receiving a transmission, for instance, a signal, such as a digital signal, from the transmitter of the monitoring device. Additionally, the system may include a network 200, such as a cellular, WIFI, or other network interface that is configured for effectuating the transfer of data from the transmitter of the monitoring device 1 to the receiver of the computing device 600. In various instances the system may include a data processing unit 300, for processing the data prior to or after transmission. Further, in some instances, the system may include a viewing system 700, such as a display screen, for instance, a liquid crystal display (LCD), light emitting diode (LED) display, plasma display, or the like.

Therefore, in action, the user 1001 of the identity, position, and/or health monitoring apparatus 1, whether it be a person such as an adult or child, or it be an animal, or an object, the tracking and/or monitoring of which is desired, is coupled with the monitoring apparatus 1. The monitoring apparatus 1 is synced over the network 200, e.g., via WIFI, BLUETOOTH®, or a cellular connection, to the monitoring device 600, which monitoring device may be a handheld electronic device, such as a mobile smart phone of a monitoring agent 1001, such as the spouse of the using adult or parent of the using child and/or the owner of the animal or object. Once synced the monitoring device 1 may play a subservient role to the monitoring device 600, which monitoring device 600 may play a master role.

As such, the relationship between the master device 600 and the subservient device 1 may be defined in many different ways. For instance, the master device 600 may set up a perimeter a given distance, e.g., X feet, away from the master device, such that if the servant device 1 approaches and/or exceeds that distance, an alarm can be set to go off warning the master device 600 that the servant device 1 is approaching the perimeter and/or has breached the same. The alarm can be an auditory, a tactile, e.g., vibratory, and/or a visual alarm that may increase in intensity and/or frequency as the distance of the servant device 1 away from the master device 600 increases. In a manner such as this a parent in control of the master device 600 may be warned when his or her child moves a given distance away from the parent. In such an instance, the master device 600 may be configured so as to periodically ping the servant device 1 in such a manner that the master device is capable of determining the distance between the two and/or whether that distance is increasing or decreasing and/or at what rate that increase or decrease is occurring.

This configuration may be useful so as to preserve the battery life of the device 1 in that it may remain in a sleep or quiet mode while within the boundary set up by the master device 600, thus only having to respond to queries sent by the master device. For instance, as described herein a wearable device of the disclosure, may be configured for safety only or may include additional features, such as entertainment and/or communication features, allowing for enhanced usability, but at the cost of battery life. Particularly, this functionality allows for additional fun and/or entertaining uses, but in order to minimize the chance that this additional functionality might compromise the safety features of the device, such as by draining the battery to the point that the safety functionality no longer works, a mechanism for shutting down non-essential, e.g., non-safety functionality, may be included.

Such essential functionality may include emergency locating, monitoring, tracking, and or communication functionality, especially with respect to devices configured to be used by children and the elderly, thereby allowing parents, guardians, and/or a monitoring service to keep in contact with the device and associated person in possession thereof. Hence, a primary function of the device may be selected so as to allow a guardian or monitor to track the location, status, and/or condition of the wearer, get alerts from the device for dangerous events or conditions the wearer may be experiencing (e.g., if they fall, their heart or blood pressure starts raising, temperature is too high, too low, entering locations they should not be in, and the like), and, in some instances, may allow for continued emergency communication between the wearer and the guardian and/or monitor.

Examples of non-essential functionality may include time determining functionality, non-guardian text or SMS messaging, music playing, internet searching, game playing, video watching, display functionality, voice activation, and the like. Thus, the device may be configured for distinguishing between essential and non-essential functionality, such as where the essential functionality may be determined by the wearer, the guardian, and/or by the system itself, but will typically include the safety features such as locating, monitoring, tracking, alerts, and possibly communication only with guardians and/or monitors, while the non-essential functionality may be the functions that the wearer likes to use, but do not involve the guardian and/or monitor in relation to monitoring the wearer. The essential functionality may be determined by the device itself based on one or more conditions of the device or the user, such as a current battery level, a current/determined time, current location, and/or status of the device or wearer in determining if non-essential functionality is allowed. If not allowed, there will be an indication to the wearer when they try to use this functionality, such as a warning beep. Such essential vs. non-essential functionality may be pre-set as a default, which may then be configured by the user or a guardian thereof. For instance, the user and/or guardian may be able to customize the rules with respect to setting the essential versus non-essential functionality settings, but in particular instances, the essential functionality may include communication functionality. As indicated, communication between the master device, e.g. the guardian and/or monitoring computing device, and the servant device may take place over network 200, which network connection can be established directly between the devices, such as through a Infra-red or Bluetooth® or LE Bluetooth® connection, or indirectly such as over a WIFI, internet, and/or cellular connection.

In various instances, the system 1000 may include one or more relays 500A, such as one or more satellites, such as a global positioning satellite. For instance, in various implementations, once the perimeter has been breached, several actions may then take place. For example, an alarm cascade may be initiated at the subservient 1 and/or master device 600, the servant device 1 may be switched from passive mode to active mode, and relay and/or beacon tracking, such as through a suitably configured relay or beacon, such as a GPS satellite 500A may be initiated. In such a manner as this the servant device 1, and the person, object, or animal to which it is attached may be monitored tracked and/or monitored. Additionally, dependent on the type, number, and placement of the various sensors that may be associated with the device 1, internally and/or externally, the distance, speed, acceleration, direction, altitude, and orientation of the device 1, and/or device wearer, may be determined, tracked, and/or monitored. In further embodiments, one or more external sensors, such as beacons 500B, may be set up throughout a given zone, such as within a localized area, such as a school, a library, a mall, a given geographical region, such as a town, a city, and the like, which beacons 500B may be configured to connect to the servant device 1 over the network 200 so that the position and/or direction of travel of the device 1 may be determined, for example, in addition or substitution for said GPS tracking.

Any suitable device capable of sending out a signal to a secondary or tertiary device, receiving a signal back therefrom, and communicating that data, such as over network 200, to an additional device, e.g., a monitoring and/or tracking device, such as master device 600, may be used. More particularly, a beacon 500B may be a satellite, a cellular tower, a WIFI enabled device capable of sending out a request for identification signal, or other device that has specifically been designed to perform the function of monitoring such subservient devices 1 within a predefined region. For instance, such beacons 500B may be distributed throughout a given location or geographical region, and together they may function to generate a perimeter, or layers of perimeters, surrounding the designated location or geographical region. In such an instance, the beacons may be configured to electronically communicate with one another, and/or may be configured for communicating with one or more subservient 1 and/or master 600 devices within the perimeter, and/or one or more master devices within or without of the region, such as over network 200.

In various instances, the subservient device 1 and/or master monitoring device 600 may include a unique code, such as a radio frequency identification (RFID) code, identifying that device, such that any and all servant devices, master devices, relays, and/or beacons, and the like may be distinguished from one another. For instance, the transmitting signals can be coded in one or more ways so as to include a unique identifier of the signal generator. Such signals may include location information and may also include a unique identifier that can be indexed to a known location, such as for enhanced monitoring, tracking, and/or data collection. For example, navigation satellite information, e.g., such as from a relay 500, and/or location sensor information, such as from a beacon 500, may include radio frequency (RF) and/or microwave powered sensors, such as heat-based (thermistor or thermocouple power sensors) or diode detector sensors. RF and microwave power sensors can allow RF triangulation with respect to known-location transmitters, such as cellular communication relay locations (e.g., cell towers), or other beacon functioning devices with known positions. Such signals, for example, may be based on the Institute of Electrical and Electronics Engineers' (IEEE) 802.11 standards (WIFI), IrDA (Infrared Data Association), ZigBee® (communications based upon IEEE 802 standard for personal area networks), Z-wave, wireless USB, or the like, and may include an identifier such as a Media Access Control (MAC) and/or Internet Protocol (IP) address of the transmitting device, or other typically unique digital or analog identifier.

Other exemplary RF and microwave signal sources that may be used as a relay and/or a beacon and/or employed by the system for determining a location of the subservient device 1, such as for determining its location and/or proximity to said relay or beacon, or other known identifying feature or landmark, include RF signals, such as from radio and television stations, as well as wireless utility meters for electricity, gas, or water, which can also be used. For example, subservient device 1 may receive signals from two or more transmitting devices, where the signals include an identifier for the transmitter (e.g., Cellular Tower Identification Number, Media Access Control (MAC) address, and the like), from which an absolute location of the transmitter can be determined, such as by lookup. Analysis of the two or more signals can then be performed to calculate a location of the subservient device 1, such as by a data processing unit 300, as described below. Particularly, the subservient 1 and/or master monitoring device 600 may include or otherwise be coupled with a processing unit 200 that can be configured to coordinate the determination of the location of the device, such as using RF fingerprinting of one or more RF signal generators. The processing unit 200 may also facilitate synchronization between the subservient device 1 and the master monitoring device 600, as well as between subservient device 1 and a server or central hub 200.

Accordingly, in various embodiments, such RF signal analysis may be used for geolocation, and/or for determining the proximity of one or more subservient devices 1 to one or more fixed position relays or beacons 500, and/or determining the distance between other associated monitoring and/or tracking devices 1, 600. In various instances, such determinations may include the measurement of the received signal strength (or amplitude) of the radio signal. For instance, in some implementations, proximity of a device 1 and/or 600 may be determined by reference to a relay or a beacon 500, such as another location device, a master monitoring device 600 (such as mobile smartphone), or a fixed relay receiver or transceiver or beacon 500.

For example, a Bluetooth® Smart signal from the identity, position, and/or health monitoring apparatus of the disclosure may be analyzed to detect an approximate distance and direction from a master monitoring device 600 and/or relay and/or beacon 500. In another instance, proximity may be obtained using Doppler principles. In such an instance, an antenna and/or transceiver attached to the monitoring apparatus 1 may send a radio signal from the user to an object, such as a beacon, having a known location. The radio signal is then reflected from the beacon back to the transceiver. In various instances, the beacon, relay, or master device 600 containing a transceiver may send out a radio signal to the subservient device, and the location of the subservient device may be determined. In such instances, the returning RF waveforms may detected, e.g., by matched-filtering, and delay in the return of the RF waveform may be measured so as to determine the distance from the object, and thereby determine its location, such as by triangulation. In a manner such as this several associated or different subservient devices may be tracked and/or monitored at the same time and/or in the same location or geographical region.

Accordingly, once synced within a given perimeter set up by one or more relays, beacons, or other such devices of known location 500B, if the subservient device 1 leaves the perimeter a warning cascade, as described above may be initiated. In other instances, such relays and/or beacon(s) may be configured such that if a servant 1 device enters a proximity of the beacon and syncs there with it, the device 1 is identified, the direction, velocity, and/or other data, such as data related to travel, health, and/or environmental, and other such data about the device 1 and/or the subject or object coupled to the device 1, may be determined, and/or communicating such as to a monitoring device 600.

Hence, in various instances, the system 1000 may include a database and/or data processing unit, which data processing unit 300 may function to receive data pertaining to one or more subservient devices 1, such as provided by one or more subservient devices 1 themselves, one or more relays or beacons 500, one or more master devices 600, and the like; process and compile that data; and then to transmit that transformed data to a receiving device, such as master device 600. In certain instances, the data processing system may be adapted to process the location, physical, physiological, and/or environmental data, e.g., generated by one or more of the subservient 1 and/or master devise 600, such as according to one or more first set of characteristic and/or characteristic generation programs, and determine a second set of compiled characteristics based on the one or more characteristic generation programs, which set of characteristics may represent one or more of a collection of processed data such as related to location, geographical, physical, physiological, and/or environmental data.

Additionally, in particular instances, the system 1000 may include an artificial intelligence module 700 such as may be associated with the database and/or data processing module 300. For instance, data generated by one or more of the system components, such as one or more devices 1, may be received and/or stored in a database, operably coupled to the data processing unit, such as for storage and/or processing thereof. The data, for example, may be processed by the data processing unit 300, which, in various instances may include an artificial intelligence analysis module. Particularly an artificial intelligence (AI) module may be included such as where the AI module is configured to collect, collate, review, and analyze the collected data, such as from one or more data collecting devices, as herein described, such as to determine patterns and/or to make predictions as to the movements or health status of the tracked person, pet, or object, and/or a condition thereof.

For example, an AI module, e.g., coupled to a server, may be included, such as where the server may include one or more processors adapted for receiving data, examining the data to determine relative patterns, and to make predictions in view of the data analysis. Such predictions may be directed to movements, health, location, and/or other associated information of a person, animal, and/or object associated with the geolocation and/or health monitoring device of the disclosure. Such patterns may be related to a single tracked and/or monitored person, pet, or object, e.g., related to a set of regular movements through known and/or previously visited locations or conditions over time, or multiple people being tracked and/or monitored the conditions of which are compared to a group average or known reference sets. In such an instances, irregular movements and/or conditions, e.g., outside of determined patterns, may signal a warning to indicate a deviation in pattern. Such a warning may indicate a risk of an irregular movement, such as in the case of an abduction, or an irregular condition, such as in the case of a health risk.

Particularly, in various instances, the tracking and/or health monitoring device of the system may be configured for being tracked and/or monitored by a system, such as where the system includes an artificial intelligence module that is configured for determining the movements and/or health characteristics of the individual wearing or otherwise associated with the device. Accordingly, as indicated, in various instances, the various devices and systems, as well as their methods of use, as disclosed herein may be employed so as to track and/or monitor a subject, such as a child or adult or even an animal wearing the tracking and/or monitoring device. In such instances, it may be useful for the overall system to keep records, or stores, of data for the subject being tracked and/or monitored, such as through a variety of environments and/or conditions, especially with respect to places the subject or object regularly visits, devices to which it typically pairs, health condition parameters for the subject, such as, regular heart rate, blood pressure, blood sugar/insulin levels, blood oxygen, carbon dioxide, or alcohol levels, state of attentiveness or alertness, and/or other health parameters, and the like.

In various instances, these regular environments and/or conditions may form patterns, which patterns may be recorded and tracked within the system, such that when a pattern is broken, the tracking and/or monitoring master device may be alerted to the change in the pattern. In particular instances, this tracking and/or monitoring may be performed by the system in such a manner so as to keep track of the pattern, such as by generating one or more data structures that may be queried so as to answer one or more questions, such as is this present location, direction of travel, and/or condition of the subject a recognized element. If so, then the system status quo may be mainlined, but if not, corrective measures may be taken by the system, such as by sounding an alarm, and/or sending a message to the tracking and/or monitoring control unit or system.

More particularly, the system may be configured such that it may be queried, automatically, e.g., by itself, or by an other party. For instance, the system may be queried such that it may be asked whether a region or condition or any other relevant factor, e.g., a factor X, is within a given prescribed range, and if not, then one or more corrective procedures may be implemented, such as for the activation of an alert, or an alarm, or sending a message, such as to the paired tracking control device and/or $3^{rd}$ party monitoring system. Specifically, in various embodiments, for answering such queries, a data architecture may be structured and searched.

In a typical architecture of such a system, such as for performing a search query, for instance, a database of regular events, factors, regions of travel, and/or conditions may be sampled over time, and their results may then be categorized and saved within the data structure. Accordingly, in various instances, the data structure may be a relational database, such as a Structured Query Language (SQL) database, which may be implemented via a relational database management system. For instance, in one implementation, the SQL database may be a table based database, such as where one or more tables form a structure wherein data may be stored, searched, relations determined, and queries answered.

Particularly, in various embodiments, a table based database may be presented, searched, and used to determine relationships from which answers to one or more queries may be determined. For instance, typically, SQL databases have a relational architecture. These constructions may be represented by a table structure. A series of tables, for instance, may then be employed by which correlations may be made in an iterative fashion. For example, with respect to whether a certain location or condition of a subject is within a predefined or determined range, a first correlation may be made with respect to the subject's normal locations and/or health conditions as determined over a set of samples, and another table may then be employed to correlate the subject's predetermined acceptable locations and/or medical conditions.

A key may be used to correlate the tables, which key may be accessed in response to question prompt or command. The key may be any common identifier, such as a name, a number, e.g., a RFID number, cellular identification number, a phone number, and the like, by which one or more of the tables may be accessed, correlated, and/or a question answered. Accordingly, without the key it becomes more difficult to build correlations between the information in one table with that of another. A further data architecture that may be used to structure a database is a data tree, where various data elements may be stored in a compressed, but correlated fashion, and/or in a hash table, as described herein above.

In other instances, a graph based architecture may be structured and used to determine the results for one or more queries. Particularly, a knowledge graph architecture may be employed to structure the database, so as to enhance the performance of computational analyses executed using that database. Such analyses may be employed so as to determine whether a given location to where a subject or object associated with the tracking device, e.g., wearing the same, is located or traveling to is within a routine pattern or not, and likewise for determining whether a given health parameter is within a normal or routine range. Accordingly, the sophisticated algorithms employed herein, are adapted for structuring the infrastructure of a relational database so as to enable more efficient and accurate searching such as via performing graph based analyses, as well as for performing table or tree based analyses.

For instance, a child wearing the device may travel in a regular pattern of locations and events, which patterns and events may form data points within the tables, trees, and/or graphs employed by the artificial intelligence module disclosed herein. Likewise, the pairing of the tracking and/or monitoring devices, with other known devices, may also form data points, from which a pattern of relations may be determined. Hence, if a pattern of pairing does not occur or is otherwise broken, a corrective measure may be initiated. Such events may also include a sampling of health data sets may be collected so as to form a normal range of a subject's conditions, wherein if the subject's condition falls outside of that range, the system may initiate a corrective action.

Consequently, in one aspect, a device, system, and method of using the same to build a searchable, relational data structure, such as described herein, is provided. Particularly, in one instance, the devise, systems, and methods disclosed herein may be employed so as to generate and/or otherwise collect data, such as data pertaining to one or more locations or geographical directions of travel or orientations and/or health conditions being monitored. Accordingly, in one embodiment, methods for building and structuring a database are provided. For instance, in a first step, data may be collected, cleaned, and then be prepared for analysis. In various embodiments, the data may be labeled and/or categorized. And once the database is structured, it may then be populated with data, in accordance with determined or inferred relationships. Such relationships may be notional or effect based.

More particularly, in certain instances, a machine learning protocol, as disclosed herein, may be employed so as to determine relationships between data points entered into the database. Such relationships may be determined based on known facts, and as such the learning may be supervised learning, e.g., such as where known factors may be used to label, categorize, and store data, such as location and/or travel and/or health related data. In other instances, the learning may be inferred, such as in an unsupervised learning. For instance, in certain instances, the data to be stored may not be known, relationships between the data may not have been determined, and the query to be answered may also not be identified.

In such instances, the data to be stored is unsupervised, and as such, patterns in data to be stored and their relationships, such as commonalities between data points, may be determined, and once determined such patterns may then be used in forming the architecture that structures the data storage. For instance, where a subject, e.g., a child, wearing the device, breaks a pattern, but in such a manner that corresponds with another known pattern, rather than signaling an alarm the system may rather infer the acquisition of a new pattern. Likewise, a known sequence of patterns may be used to infer that if events A and B in a known sequence may be followed by event C such that if event C does not happen as predicted, an alarm may be set off.

At the heart of the platform, therefore, may be a graph database, which gets its information from one or more devices and/or subjects being tracked and/or monitored. For instance, such data may be generated and received by the system, such as from a child wearing the device, and/or the locations to which he or she travels, and/or which may be generated by the biomonitor and/or biological tracking functions of the device. Hence, in various instances, machine learning may take place by configuring the system to instantly recognize how an output was achieved based on the type and characteristics of the input received. Specifically, in various instances, the present system may be configured to learn from the inputs it receives and the results it outputs, so as to learn to draw correlations more rapidly and accurately based on the initial input of data received.

Hence, once the A/I machine learns the behavior, the learned behavior may then be applied to a second type of data, such as an inference engine, that is used to answer one or more unknown variables. There are several different types of relationships that can be determined. For instance, relationships may be determined based on their effects, e.g., they are effect based; or they may be determined based on inferences, e.g., relationships that are unknown but determinable. Specifically, a relationship between two subjects, locations, and/or conditions of one or more subjects may be inferred based on various common effects observed between them. These unknown relationships may be determined and/or used in predictive models by generating the knowledge graph.

For example, in various instances, the locations and/or health conditions commonly experienced by the subject wearing the device may form nodes of a knowledge graph, and for each time a subject travels from one known node to another, a relationship between the two nodes may be determined and strengthened, such that predictions may be made from which the system may determine that if the subject is at one given node at one time, it may be predicted that the subject will subsequently be traveling to the other joined node. However, if such an event does not occur, such as within a predicted timeframe, a corrective measure may be initiated. The subjects medical or health conditions may also be employed as nodes within the knowledge graph, from which relationships with respect thereto may be determined. Other known, e.g., effect based, data points may also be generated, or otherwise entered into the system and may be used to generate one or more nodes, e.g. a constellation of nodes, which may then be used in the determination of relationships.

Additionally, once the knowledge graph architecture has been constructed, it can continually be updated and grown by adding more and more pertinent data into the knowledge structure, such as data received from any relevant source of information provider pertaining to the subject(s) under examination, and building more and more potential nodes and/or relationships. In various embodiments, the system may be configured for being accessible by the subject and/or a third party having the appropriate access permissions. In such an instance, the user may access the A/I module, e.g., via a suitably configured user interface, upload pertinent information into the system and/or determine the relevant nodes by which to answer an inquiry, e.g., such as is this location or direction of travel authorized or otherwise expected.

Any suitably configured artificial intelligence machine containing the appropriate programming may be used by the system to implement that artificial intelligence module. For instance, a suitably configured AI module may implement a machine learning protocol, where the processing system recognizes a pattern, makes a prediction, receives the results data, and analyzes the results data to better achieve more accurate predictions moving forward. Particularly, the server may be configured for performing natural language processing, information retrieval, knowledge representation, automated reasoning, electronic database searching, pattern recognition, and the like. Such algorithms may be configured in a hardwired and/or software form, such as employing DeepQA software, Apache UIMA, Java, C++, Prolog, and the like. More particularly, the server may be a SUSE Linux Enterprise Server. In particular instances, the server may be a Watson computing platform.

Further, as described herein, the system and/or A/I module may be configured for monitoring the system operational parameters, generally, and/or the components of the system or tracking and/or monitoring device, and may trigger alerts for an individual or object associated with the device. The character of alerts triggered can vary based on the type of preferences and/or the system operational parameters employed. For instance, the alerts may include: an alarm to indicate a low battery life, an alarm may be sounded when the tracking and/or monitoring device leaves a certain predefined perimeter from the master device and/or when the connection is disconnected due to long distance and/or transitions from one mode of tracking, e.g., from one communications link, to another; or when a condition of an individual changes beyond a prescribed or determined limit. Additionally, an alarm may indicate an incoming message has been received, a change in the status of the device, or that there is a change in an individual wearing the device, such as a change in health status, or a stress level. For example, the alarm may be a distress alarm for when a user desires to draw attention to themselves, such as when a change in position and/or orientation, e.g., a fall alarm, occurs, and the like. The alarm may be manually operated or automatic, such that if a given predefined condition occurs, such as a fall, a drop in a health parameter, or the like, the monitor automatically sets off the alarm. Additionally, in certain instances, the A/I module may be configured for providing voice recognition, sentence completion, location identification, such as by compiling a plurality of data elements, such as with regard to data elements such as those disclosed herein, and/or for providing a virtual assistant, such as a voice activated personal assistant, to assist in the functioning of the device. The A/I module may also be configured for making predictions with regard to movements of the device based on collected and/or historic data.

In such instances, the along with the alarms various communications and/or other associated data may also be generated, and once triggered may then be transmitted to a master controller, central server, and/or a third-party monitoring agency. Such data transmission may be obtained and transmitted over a communications link, such as a cellular link, e.g., via the cellular network provider, a WIFI link, a Bluetooth connection, and the like, as described herein. For instance, in various embodiments, the monitoring and/or tracking device may be connected to a paired device, e.g., through a cellular network connection, or to a remote server, such as through an internet connection, through which connections the device can remotely communicate with and/or be controlled by with the master controller and/or third party monitoring system, such as over any cellular or Internet connection, such as through cellular or an internet provider. The internet provider may also send the information through a cellular service provider, such as via cellular satellites, and through such satellites position can be triangulated via a cell tracking system. Additionally, a GPS satellite may be employed to provide GPS position information that can also be used for determining the location information.

Accordingly, in such embodiments, the tracking and/or monitoring device may be a wristband, such as a bracelet or watch, having an antenna, which may be coupled to a suitably configured amplifier. As indicated, a GPS transceiver may also be included so as to receive GPS information. A general or dedicated cellular processor may also be provided so as to allow communications over the cellular network. In particular instances, the antenna may be a directional antenna, e.g., a YAGI type antenna, in the tracking and monitoring device so as to allow the locating and/or tracking device to determine which direction the tracked unit is in, e.g., with respect to the master control device and/or a $3^{rd}$ party monitoring and/or tracking service.

In various embodiments, the device may include a button, which button may be configured as a panic button, that can be configured to allow a user wearing a tracked and/or monitored unit to alert the tracking and/or monitoring person, e.g., a parent, to a dangerous situation that the wearer of the device may be in. Likewise, the same or different button may be configured as a paging button to output a paging signal, call, or text, e.g., SMS, to or from a tracked and/or tracking unit. Further, in various embodiments, the monitoring and/or tracking device may include a photo and/or video camera, and in such instances, the camera may be configured for taking pictures and/or video, which pictures and/video may then be transmitted over the cellular and/or internet network connection to the master control device and/or central server and/or third-party monitoring device. This functionality may be activated via voice command or trigger activation, e.g., by the user of the monitoring device, or may be activated remotely by the master controller and/or remote third-party user. In various instances, these pictures and videos may be used to better determine the location and/or status, e.g., health status, of the tracking device and/or person or animal wearing the device.

Such data transmissions could originate from the device itself to a monitoring device and/or server center, or may be directed from the monitoring device/center to the monitoring and/or tracking device, such as for monitoring, tracking, and/or for the purpose of activating or configuring the device. The configuration may be such that it orientates the device's cellular circuitry so as to enable cellular transmission and receipt, such as for enabling cellular communications. Particularly, in various instances, the monitoring and/or tracking device may include a triggering element, such as a button, that when activated, e.g., be depression, the device may call a predefined number. In certain instances, the trigger may be voice activated, and may be used to call a preselected or a voice entered number. Such as for real-time talking, for sending messages, texts, SMS, and the like.

Particularly, the device may include a call button to accept an incoming call, or to make an outgoing call. The call button may be programmed to call the master controller, a monitoring center, or one of several other contacts to assist the monitored user. In various embodiments, a plurality of real or virtual buttons may be included so as to control a variety of operation parameters and functionality. For instance, the communications button, when activated, may be configured to call or send a message or data to one or more preselected numbers, and in some embodiments the user may select those numbers from a list or speak a voice command to dial a pre-designated number. Hence, the processor may be further configured to accept voice commands via an included microphone such as upon activation of the call button, such as via voice or mechanical activation, and route communications to a requested destination. In certain instances, the transmission may be immediate, or it may be queued for delivery if given conditions are met. Accordingly, in various instances, through the cellular communications link, the tracking and/or monitoring device may be capable of talking to, or otherwise communicating with, e.g., via the cellular communications link, to a master controller and/or to a monitoring center. In certain embodiments, when triggered, e.g., by a monitored user, the button may be a "help" button, which causes a paired device to contact a monitoring center.

As indicated, such alerts could be audible and output through an included speaker, could be in the form of a vibrating alert, or could be silent and sent to control device/monitoring center which will respond accordingly, and such communications may be audible, text, recording, video, and/or data, e.g., meta data, and the like. In certain embodiments, the tracking and/or monitoring device may, but need not include, a display screen, such as a light emitting diode, such as an LED, OLED, and the like. Hence, the display screen may be any suitable screen, such as a capacitive sensing touch screen. In particular embodiments, the display may be configured for receiving user inputs, such as for allowing navigation through a plurality of menus, e.g., presented at the display interface, and may further be configured to display various indicators, such as signal strength of a cellular network, GPS network strength, and/or incoming and outgoing messages. The display screen may also display a battery power indicator, a Bluetooth connection indicator, date and time, and audio mode indicator, as well as function and status indicators.

Accordingly, in one aspect, presented herein is a system configuration and method for handling a communication between the tracking and monitoring device and the master control device or $3^{rd}$ Party monitor, such as where the communication button is triggered, such as by an individual wearing the monitoring device. For instance, a communications interface, e.g., a button, such as a help or call button on the device, may be activated. In such an instance, communications transfer may be initiated, such as where a call is placed.

Particularly, the call may be received directly by the master control device, e.g., of a parent, or by a central server and/or then directed to a master control device and/or a 3$^{rd}$ party monitoring server. In various embodiments, the communication may be direct with the master controller and/or the 3$^{rd}$ party monitor, such as without going first through the central server. Upon receipt of the communication, the monitoring device and/or its user may be authenticated. For example, the RFID of the device, and/or the user ID, e.g., device subscriber ID, may be received and examined, such as for authentication and/or determination purposes. Geolocation and/or other data, such as metadata and/or status data, may be transmitted from the monitoring device to the server and/or directly or indirectly to the master controller and/or 3$^{rd}$ party monitor. Once authenticated, the data may be examined and/or transmitted to the master controller and/or the third-party monitor by the central server. The data may then be compiled, examined, and one or more operations initiated. Specifically, in various embodiments, as disclosed herein above, the central server may include an artificial intelligence module that is configured for analyzing the received data, making one or more determinations with respect thereto, and thereby initiating one or more actions that are to be implemented by the system.

Accordingly, once the nature of an emergency has been determined, the system may then contact the appropriate emergency facilities, so as to notify them of the emergency, if appropriate. For instance, the monitored user may have specific health concerns which are already known, for which the system is monitoring. In other instances, the system may be monitoring the device user to determine if there has been a change in one or more status indicators being tracked by a device of the system or the system generally. For example, if there is a change in orientation or position of the user, such as due to a fall, this may be determined by the system and reported thereby.

In such instances, the system may be configured for not only determining a condition of the user wearing the monitoring device but also their location, such as by mapping their last known location. Specifically, a user of the tracker or the master controller may activate a trigger of either device so as to send or receive location data of the either device, which data may then be transmitted to the central server and/or 3$^{rd}$ party monitoring device. Particularly, when a button of the device is activated, geolocation data, such as from the GPS engine, may be transmitted from one device or system to the other. And in certain instances, the receiving device may display a graphical user interface that displays the location of the transmitting device. In addition to the present location data, a historical list of location data may also be identified and transmitted. In particular instances, the quickest route from one device to the other may be determined and displayed on the map. If no emergency is identified, either by the system or 3$^{rd}$ Party monitor, or the like, information may simply be reported back and forth between one or more of the monitoring and tracking device, the master control device, and/or the monitoring service.

In such a manner, a plurality of subservient devices 1 may be tracked and the identity, condition, and/or location and/or position of the servant devices 1 may be determined and/or monitored. In various instances, the receiving device may be a master controller device configured to control the functioning of one or more of the beacons, relays, subservient devices, and/or the sub-master devices. Accordingly, in certain instances, synchronization between one or more of the devices of the system 1000 may be desired. In such an instance, synchronization or association between the one or more devices of the system may include an exchange of electronic data. The exchange of electronic data may notify one or more of the associated device (e.g., the master monitoring device 600 such as a smartphone) of a unique identifier, e.g., RFID, for each of the other devices, or may provide a code shared in common by all of the associated devices.

Such devices may use unique identifiers to individually communicate with any or all of several associated devices of the system, including various relays 500A, beacons 500B, and/or other subservient 1 and/or monitoring devices 600, and may obtain device-distinguishable data from each associated device. In various instances, all of a group of devices may share a common code for identification, such as all the subservient or master devise within a given system, in such an instance, a master controlling device may treat the group of devices sharing a common identifier as a single unit. In such implementations, a controlling device may learn of proximity or location from any one of the associated subservient devices. This may be useful and efficient in instances where all of the associated devices are typically considered together, such as when belonging to members of the same family that move together.

In various instances, a common code/password/key/token, etc. may be used as a part of an encryption scheme, such as wireless access protocol (WAP), wired equivalent privacy (WEP), WIFI Protected Access (WPA), variants thereof, and/or other standard or proprietary security protocols permitting secured communications. Such security protocols may implement cryptography algorithms such as advanced encryption standard (AES), data encryption standard (DES), RSA, and the like. In addition, communications may implement compression algorithms and/or hashing functions in order to reduce the amount of data transferred and to ensure data integrity. The encryption schemes may be implemented using dedicated circuitry and/or general purpose processors, as described herein, and may further utilize processors, magnetic and/or solid state memory devices, electronic fobs, electronic dongles, SIM cards and the like, or any combination thereof.

As indicated above, in certain instances, the system may be configured for transmitting and/or displaying the various data collected, processed, and/or compiled, as discussed herein, using the techniques described herein. Particularly, the system disclosed herein may make use of one or more of a geolocation device, such as that described above, a network, a data processing unit, one or more external sensors, e.g., a beacon or relay, and/or a receiver, such as a computing device, e.g., a mobile computing device, to collect and compute various data. In various instances, such data may be transmitted and/or displayed to a second and/or third party, such as a second or third party interested in identifying, monitoring, and/or tracking the user and/or the user's activities and/or health.

For instance, it may be useful to display such information to one or more users of the system, and hence in various instances, the system 1000 may include a display 700, such as a display configurable for displaying a picture or other graphical representation of the set of data characteristics measured. For example, in some embodiments, the set of characteristics may be adapted to represent one or more of the physical location, state, manner of movement, and/or a physiological condition of one or more users 100 of one or more monitoring devices 1. Such data may be stored, such as in a memory of one of the monitoring and/or tracking devices, and/or may be transmitted to one or more other devices. If displayed, the data may be displayed using any suitable device, such as a display of a desktop or mobile computing device, such as a liquid crystal display (LCD) or a Light Emitting Diode (LED) or the like. The resulting displayed material may be presented in a variety of ways including quantitatively, qualitatively, comparatively, in the form of a chart, in the form of a table, and/or in the form of a graph or other graphic.

In another aspect, as can be seen with respect to FIG. 5, a wearable geolocation and/or status monitoring device 1 is provided. In various instances, the geolocation device 1 may have a thin profile and/or may be waterproof, and in certain instances, may be configured for locating a human, animal, or object within a defined geographical region. Particularly, the geolocation device 1 may include a substrate, such as including a housing 40, such as a flexible and/or an elastomeric housing 40 that is sized and adapted for being worn, such as about a neck or limb of a human or an animal. In particular instances, the elastomeric housing 40 may have a circumferential portion 43 such as a portion that bounds a first surface 42 and a second surface 44 spaced apart from the first surface to form a chamber or cavity 45, e.g., a waterproof cavity, that is bounded by the circumferential portion 43. For instance, in one embodiment, the first surface 542 is separated from the second surface 43 of the elastomeric housing 40 by a thickness, such as a thickness of about 3 cm or 2.5 cm or 2 cm or less, such as about 1.5 cm or 1.2 cm or less, for instance, about 10 mm or less, such as about 8 mm or less, for instance, from about 1 mm to about 3 mm or to about 5 mm or about 6 mm, or more so as to have a low profile when worn about the limb, e.g., of the human. In one implementation, the size dimensions may be about 45 mm×31 mm×9 mm, in a compact pendant like configuration. In particular instances, the device may be lightweight, such as less than about 0.200, or less than about 0.150, or less than about 0.100, or less than about 0.50 or about 0.25 ounces. For instance, in one implementation, the device may weigh about 0.67 ounces.

The geolocation and/or status monitoring device 1 may include a flexible, rigid, and/or semi-flexible or semi-rigid digital logic circuit board arrangement 10 that may be contained within the cavity of the flexible housing 40. The digital logic circuit board arrangement 10 may include a substrate 7 having an elongated body defined by a circumferential portion, the circumferential portion bounding a first surface and a second surface of the elongated body, the first surface being opposite the second surface by a thickness that is sized and adapted for being positioned within the cavity 45 of the elastomeric housing 40, such as a thickness of less than about 20 mm or less, such as less than 15 mm or less, for instance, less than about 10 mm or about 5 mm or about 3 mm or less.

In various instances, the elongated substrate 7 forms a rigid, semi-rigid, semi-flexible, and/or a flexible digital logic circuit board arrangement 10 that may be a single unit or a plurality of units, such as including one or more rigid circuit board portions that may be connected one to another, such as by flexible or semi-flexible circuit sections of the elongated substrate 7. Particularly, in particular instances, a rigid, semi-rigid, semi-flexible, and/or flexible digital logic circuit board arrangement 10 may be provided, which may be contained within the cavity 45 of the elongated body of the substrate 7. Accordingly, in one instance, a semi-flexible digital logic circuit board arrangement 10 including a plurality of rigid circuit board portions connected by one or more flexible portions may be provided, such as where the digital logic circuit board arrangement 10 may include an integrated circuit, such as a processing unit (CPU/GPU) 12, such as a CPU 12 that is in communication with a communications module 16, which may include a GPS receiver, a memory 14, and/or a battery 18.

Additionally, in various instances, the digital logic circuit board arrangement 10 may further include a pairing device 17 for pairing the geolocation device 1 with a remote master device 600 via a wireless communication channel. In such an instance, such pairing may be implemented within a defined distance, such as between the geolocation device 1 and the master device 600 such that if the distance between the geolocation device 1 and the master device 600 exceeds a predetermined range, an alarm may be set off in one or more of the geolocation device 600 and the master device 600. Further, in additional embodiments, the digital logic circuit board arrangement 10 may include one or more of a SIM card, a geolocation receiver, and a communications module, such as where each of the CPU/GPU, the geolocation receiver, and the communications module may be mounted to at least one of the plurality of rigid circuit board portions and/or to a flexible circuit board portion.

In such an instance, the communications module 16 may include a global positioning satellite (GPS) receiver (or other geolocation receiver) and/or a radio frequency (RF) transmitter, a cellular transmitter, a WIFI transmitter, a Bluetooth transmitter, and/or a low energy Bluetooth transmitter 19. Particularly, in terms of functioning, the CPU 12 may be configured to receive geolocation data, such as from the geolocation receiver, or other location identification asset, such as based on the received geolocation data, e.g., relative to the geographic region. Further, based on the received and computed data, the CPU may select one or more of the RF transmitter, cellular transmitter, WIFI transmitter, Bluetooth transmitter, or low energy Bluetooth transmitter to transmit the signal, such as to the one or more master controlling device 600.

In this manner, the geolocation device 1 may be tracked through a range of geographical regions, coming into contact with a number of different signal identifiers and/or generators, and in doing so, signals may be generated and sent to and from the device based on which transmission mechanism is best suited for performing the transmissions, based on a multiplicity of relevant factors, such as energy consumption, signal strength, speed of motion, directionality, altitude, presence and positions of various beacons, other paired and/or location devices, and the like. In such a manner, transmission from the geolocation device may be implemented by a multiplicity of the included communications elements 19, e.g., transmitters, such as sequentially, e.g., from one transmitter to another, such as from one or more of an included radio frequency (RF) transmitter to a cellular transmitter to a WIFI transmitter to a Bluetooth transmitter and/or to a low energy Bluetooth transmitter depending on which transmitter may be more effectively and/or efficiently employed, e.g., as determined by the CPU/GPU, given the circumstances at the time of transmission and/or relevant battery and/or signal strength.

Accordingly, in a further aspect, a method for monitoring and/or tracking a person or an object is provided. The method may include one or more of providing a geolocating device, such as that set forth above, attaching the geolocating device to a person, animal, or an object to be monitored and/or tracked, and employing a receiver to monitor and/or track the person, animal, or object, such as over a network joining the two. More particularly, the method may include providing the geolocating device and employing the system described above to monitor and/or track the person, animal, or object. In various instances, as indicated above, the system may include a relay, such as a beacon, that is configured to receive a signal from the geolocating device so as to thereby determine the location of the device, and further transferring that information, such as via the network, to the receiver so as to thereby allow a third party to monitor and/or track the position and other data collected by the device.

Yet another aspect of the instant technology is a method for determining a set of characteristics of a user of the geolocation device, which in this instance may be configured as an identity, position, and/or health monitoring apparatus, e.g., geolocation device. The method may include one or more of the following steps. First, the method may include receiving directional, movement, environmental, and/or physical, e.g., health, data associated with the user, animal, or object of the device, such as where the directional, movement, environmental, and/or physical data may be collected by at least one sensor or other data collector that is associated with the user and/or his or her environment and/or the device itself. Further, the method may include receiving, processing, and/or transmitting the directional, movement, environmental, and/or physiological data associated with the user and/or their activity and/or their environment. In various instances, the processing of the data may be in accordance with one or more characteristic generation programs, and may include determining and/or associating various elements of the sensed and/or transmitted data based on the one or more characteristic generation programs. In particular instances, the method may include transmitting the raw and/or processed data over a communications network to one or more devices that may be paired with the geolocation device(s), such as by being associated with a common network. Particularly, in certain embodiments, the method may further include transmitting the set of characteristics to a data processing and/or artificial intelligence system over a wireless communication network, such as in an efficient and optimally effective manner.

Figure 6:
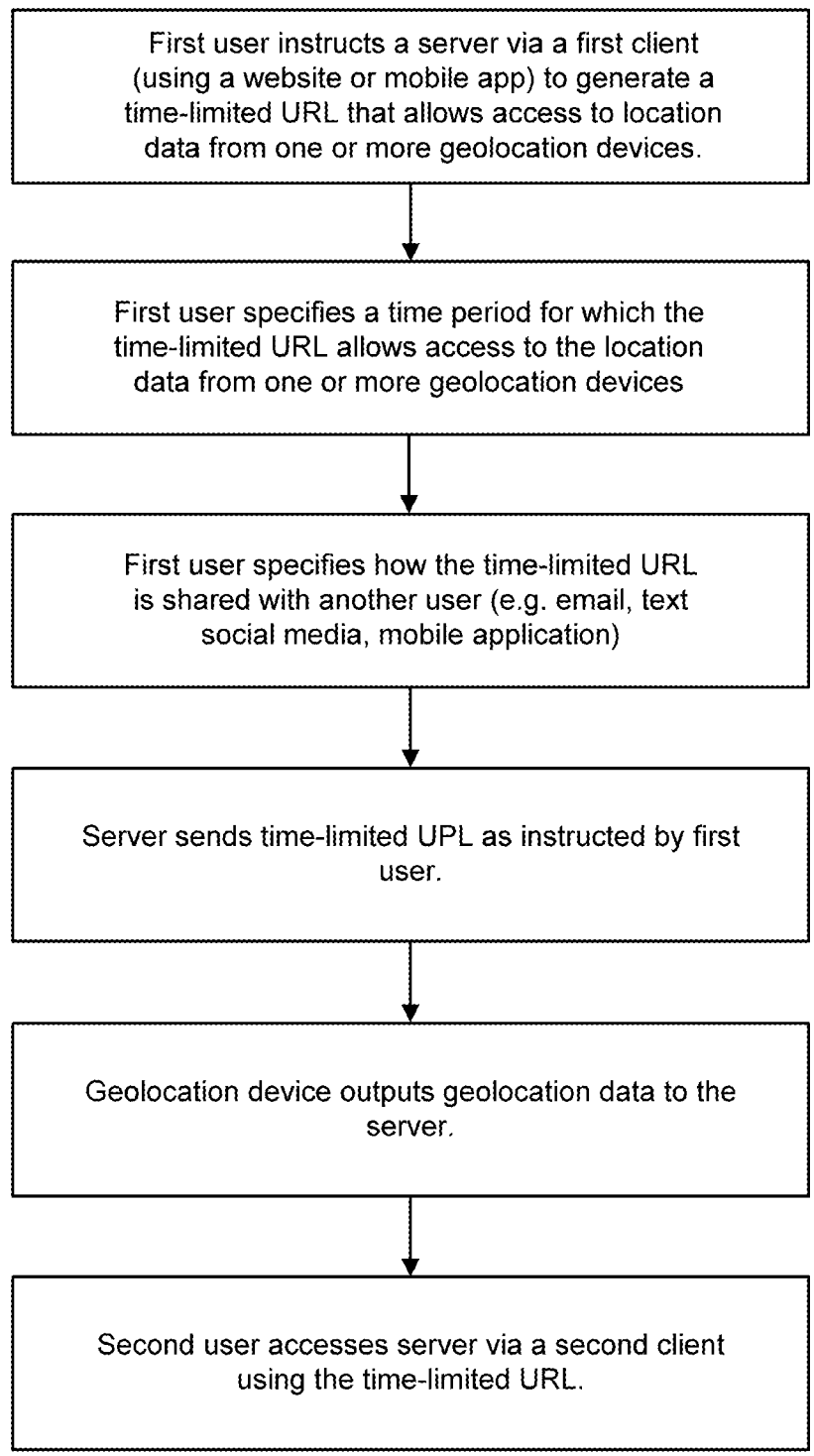
FIG. 6 presents a flow diagram for enacting a time limited URL protocol for locating a user of the identity, geolocation, and/or health status monitoring apparatus of the system.

Accordingly, in one aspect, as can be seen with respect to FIG. 6, a method for allowing the geolocation device to be tracked over time and/or position may be provided. For instance, in various embodiments, a system and/or a method for creating time-limited access to and/or from the geolocation data is provided. For example, a system may be provided wherein the system includes a geolocation and/or health monitoring and/or environmental sensing device, as herein described, a server, such as a cloud based server, and/or a third party client device, such as a computer or mobile computing device, and/or a pattern analysis computing hub, such as including an associated database and/or AI server. In various instances, the system may further include a geolocation determining device, such as a beacon, cellular tower, global positioning satellite, geolocation station, and/or other positioning determining device that is capable of connecting to and/or otherwise communicating with the geolocation device of the disclosure. As such, in particular instances, the geolocation device may be configured to include a pairing device for pairing the geolocation device with another geolocation determining device, such as a beacon and/or geolocating station, so as to generate geolocation data, and may further allow the pairing of the geolocation device with a further, e.g., controlling, or other associated device.

Accordingly, in various instances, a method of using the system may be provided wherein the wearable geolocation device as described herein may be used to both generate location and/or other user selectable data, e.g. location, environment, and/or health data, and send that generated data to one or more of third party devices, such as a master controller and/or other party device, such as to allow a first person to locate and/or monitor a second person or animal, and/or object wearing or otherwise associated with the geolocation device. For example, the method may include providing a geolocation and/or environment and/or health monitoring device, e.g., configured as disclosed herein, for generating geolocation and/or other data, for instance, location and/or health information of the person or animal wearing the geolocation device.

A location-receiving and/or status monitoring device, e.g., master controller, may also be provided for receiving signals and data from the geolocation device. Additionally, a server, e.g., a cloud based server, may be provided and configured for receiving the geolocation and/or other environmental and/or health related data generated by the geolocation or other location determining device, and processing the generated geolocation and/or other status data to produce location, e.g., secure location, and/or other results data, which may be processed, e.g., directly or by a central processing hub, and sent to a third party device. In particular instances, the processing may include generating a unique key, such as a unique key for associating the geolocation and/or status monitoring device, e.g., which may be configured as a bracelet or pendant, with the geolocation, environmental, and/or health status data generated and/or to be transmitted. In certain embodiments, the unique key may be configured as and/or otherwise associated with a time-limited uniform resource locator (URL), which may be configured for the secure accessing of the generated and/or transferrable data. In specific implementations, the URL may be used to allow a parent or guardian or medical assistant, and/or government authority to access the generated geolocation, health, and/or environmental data of the person, animal, or object associated with, e.g., wearing, the device, which URL may be accessed for a given period of time.

Accordingly, the geolocation and/or receiving and/or other controlling devices may include a location or other signal emitter so as to generate and/or transmit geolocation and/or other environmental and/or health status data, and/or a receiver for receiving the generated and transmitted signals, so that the various data signals may be generated by the wearer's device, and be sent to the receiver's, e.g., a requester's, device that is configured to request and receive the geolocation and/or other data from the geolocation device. Such location and/or other data may be directly provided to the receiving device, so as to be immediately accessible to the receiving device, or indirectly such as by sending an accessible link, e.g., over a secure network, to the receiving device, thereby allowing an operator to click on and activate the link and thereby be granted access to the location, environmental, and/or health status information.

The method, therefore, may also include providing a server configured for receiving the geolocation data generated by the geolocation device, the server for processing the geolocation and other data to produce a secure uniform resource locator ("URL") for accessing the geolocation data, and transmitting the processed geolocation data to a master control device or third-party or other requester device. In such an instance, a unique key generator may be included such as where the unique key is generated and configured for associating the geolocation device, e.g., bracelet or pendant, with the geolocation data, such as in a secure manner so as to produce the secure location and/or other results data. Hence, in various instances, a time-limited URL may be generated from and/or associated with the unique key so as to provide secure access to the geolocation data by the accessor's device.

Additionally, a time indicator may also be generated, such as where the time indicator is configured for indicating a time period during which the generated time-limited URL is allowed to be accessed, so as to allow the geolocation data to be securely received and viewed. Further, the method may include associating the time indicator with the generated time-limited URL, and transmitting the time-limited URL, e.g., computer link, to the receiving and/or controlling and/or third party device, thereby allowing an accessing party, such as a parent, health care professional, governmental agency, or other concerned third party to locate a person, animal, or object, as well as their health and/or environmental data, by accessing, e.g., by "clicking", on the transmitted time-limited URL.

Accordingly, in one use model, a system as disclosed herein, may be provided so as to allow a user, such as a first user, e.g., a parent requesting location information of another "second" user, such as a child wearing the device, to access geolocation data, e.g., location, environment, and/or health data, of the child wearing the geolocation device, and/or allow a third party user to receive accessible information regarding the location and other information. Hence, in various embodiments, a method for using the system may be provided, such as where in a first step, a first user instructs a server, e.g., via a first computing client, for instance, using a website, mobile application, the geolocation device itself, or the like, to generate a time-limited URL that allows access to location data from one or more second users having, e.g., wearing, one or more geolocation devices.

For instance, a downloadable application or "app" may be provided for allowing a user of a paired device, e.g., a mobile or desktop computing device, to identify and track and/or communicate with the health monitoring and/or tracking device of the system. Particularly, the app may be configured for allowing live tracking, e.g., for real time viewing and/or tracking, such as regardless of where the device is and/or how fast it is moving. Specifically, the device may be configured for communicating with the paired, or other tracking, device the speed, bearing, and/or level or other characteristics of activity being engaged in by the device holder. Additionally, the device may provide the ambient temperature and/or change in temperature of where the device is located. In that regard, the history of location, distance, direction, speed, activity levels, temperature, of the device and/or wearer may be recorded, data pertaining thereto stored, and/or transmitted to a network coupled monitoring device, such as a paired device. One or more alerts may also be initiated of the health monitoring and/or tracking device, if it moves in a manner outside of preset parameters, such as beyond a selected distance, speed, acceleration, orientation, temperature rise or fall, and the like.

Hence, in one implementation, in a second step, the first or second user may then specify a time period during which the time-limited URL allows access, e.g., to a first and/or third party, to the location data from one or more geolocation devices being worn by one or more secondary users, animals, and/or objects to be tracked. Further still, in a third step, a user may then specify the mode of transmission of the time limited URL to be sent, such as from the server to the first or third or other party's client computing device, such as via email, text message, social media account, e.g., Facebook, Twitter, or other mobile application, and the like. In a next step, the server will receive these and other inputs, determine the geolocation data, and then, in a further step, send the link, e.g., URL, to the geolocation data to the selected user in accordance with the selected mode of transmission. Upon access of the link, e.g., by the requesting or third party, the system will signal the geolocation device to update and/or forward geolocation data to the server, and that information will be revealed to the requesting and/or receiving party, such as by sending coordinates, an address, a position location within a range of position locations, an icon on a map, and the like.

In various instances, the provided access to the secure location and/or other results data, e.g., via the time-limited URL, which allows secure access to the geolocation data, e.g., which may be realtime data, may be restricted. For instance, the requesting party may need to be verified to ensure that access is authorized, such as by having the requestor input a pass code, answer one or more security questions, and/or the like. Additionally, the access may be restricted for a constrained period of time and/or number of accesses or updates. As such the method may include generating a time and/or access indicator, such as a time and/or number indicator for selecting and/or indicating a time period and/or number during which the generated uniform resource locator (URL) allows access to the geolocation and/or other data, e.g., to the requesting person or third party.

Hence, when the time or number limited URL is accessed by the third party computing device, the geolocation and/or other data, from the one or more geolocation devices of the system, is exposed for a limited period of time and/or accesses, and when the determined or selected period is completed the time-limited URL is dissociated from the geolocation data. In certain instances, the time and/or number period may be predetermined and/or selected, such as from a menu of options of times and/or access numbers, and the method may include associating the time and/or access number indicator with the generated time-limited URL. Once a status update has been generated and the access rights determined, the URL may then be transmitted to the requesting device thereby allowing the authorized requestor to locate the person, animal, or object, such as by accessing the transmitted time-limited URL. Finally, once the time and/or number period has been reached, the time/number-limited URL is dissociated from the geolocation data, e.g., when the time period of the time indicator is completed.

Accordingly, in various instances, in particular iterations one or more users can share the location of one or more given bands, such as via a web link accessible from a mobile application or website. For instance, an app and/or a website can be accessed, via a link, by a user, where the user can select a particular geolocation device to be accessed, and a request may be sent to the device where the device will either automatically send a location, environmental, and/or health status update, e.g., via the link, or may prompt for the device user to authorize and thereby allow the update to be sent. In such a manner, the device user may select to share the device's location and/or other status, such as via an email application and/or a social media interface, e.g. such as Facebook, Twitter, and the like. Additionally, the system and/or device may allow the user can select a time limit for the sharing, such as 4 or 8, or 16 or 24 hours, 1 or 2 or more days, or a week, or a month, etc. In various embodiments, such updates, especially those updating a social media platform with a status update, can be used by the processing server to analyze and/or predict future locations and/or health and/or environmental condition statuses. Any associated social media platforms can be analyzed and/or tracked, such as FACEBOOK®, TWITTER®, INSTAGRAM®, FLICKER®, SMS®, WHATSAPP®, and the like.

More particularly, during use, each of the paired devices may access the same application allowing one device to share a link with the other device, such as via sharing a link to a suitably configured website. In such an instance, the website may present a map, e.g., of a geographic region, or otherwise show the geolocation device as well as its tracking history and/or its current location information of the selected device, such as during the duration of the sharing period. Such data may also include health and/or environmental condition data. However, once the time limit expires, the link and/or website will no longer be updated. In various instances, the site may have an "Update Now" button to allow users to get the most up to date location information. In various instances, one or more of these features can be used in a variety of different user tracking applications and for a variety of different purposes, such as for sharing a child's location with a guardian, parents, grandparents, siblings, and the like while the child is staying with them or away from home, allowing for the sharing of location data for someone taking care of the child, such as at an all-day activity, and even for monitoring sporting events such as cross country, running, or bicycling events.

In particular embodiments, the request for location and/or other status information from the geolocation and/or health and/or environmental condition monitoring device may be sent to the geolocation device as a request for access, which request and/or acceptance may be automatic or may be subject to being accepted or rejected by the user, such as by the user pressing a button and/or via a haptic gesture. For instance, in various embodiments, as can be seen with respect to FIG. 7, a method for using a haptic gesture to request and/or accept transmission of real-time geolocation and/or environmental and/or status data, such as from a geolocation device, e.g., for a limited period of time, so as to allow a first person to locate and/or get a status update for a second person, animal, or object wearing or otherwise associated with the geolocation device is presented. For example, in various implementations, the device may be configured for providing real-time tracking, monitoring, and alerts, as well as voice enabled activation and message transmission, streaming music, and broadcasting, e.g., targeted broadcasting, such as of location and/or activity tracking. Particularly, in certain implementations, the device may be configured for performing voice calls and messaging, such as via a virtual assistant and/or real-life help center, like a monitoring center.

Specifically, in various embodiments, a method for requesting and/or authorizing access to real-time geolocation and/or status data, such as from a geolocation device, as herein disclosed, is provided. In certain instances, one or both of the request and/or the authorization may be made by performing a haptic gesture so as to request and/or authorize transmission of real-time geolocation data from the geolocation device, e.g., for a limited period of time, so as to allow a first person to locate and/or track a second person, animal, and/or object wearing, or otherwise being associated with the geolocation device. In such an instance, the haptic gesture may be any suitable gesture such as a movement of a limb in a prescribed motion, or arrangements of motions, and/or may include interacting with a real or virtual button or switch present or presented on a requesting and/or authorizing device.

For instance, a requestor desiring to learn of the location and/or status of a person, animal, or object associated with a geolocation device of the disclosure, may press, or otherwise manipulate, a button, or representation thereof, e.g., presented on a screen, such as a touch screen, of a computing device that is paired to the geolocation device, and thereby cause the requesting device to send a request either directly or through an intermediary server device, such as a cloud based server device, to the geolocation device. Likewise, once the geolocation device receives the request, e.g., from the requesting computing device, the geolocation device may then send back, either directly or through an intermediary server, the geolocation and/or status information automatically or once authorized, such as by the wearer of the geolocation device, such as by using a haptic gesture.

For example, the wearer of the geolocation device may receive the request for geolocation and/or other status information, such as by an auditory, visual, vibratory, and/or other alarm system notifying the wearer of the geolocation device that a request for information has been received, which request may be responded to by the device sending the requested information back to the requesting automatically, or the device may be configured so as to require a response, e.g., a gesture, from the wearer of the device prior to sending the requested response. Such a response may, for instance, may be a haptic gesture such as a gesture described above.

Additionally, in various instances, a method for tracking and/or monitoring, such as on an as needed basis is provided. For instance, the CPU of the master controller and/or an associated CPU/GPU of the geolocation device may be configured for allowing real time tracking of the geolocation device, such as through a tracking and/or monitoring application, e.g., software, of the devices. Specifically, through the tracking application, a user of a master controller device may activate the application, as herein described, and thereby initiate a real-time tracking and/or monitoring protocol, so as to enable the geolocation device to send periodic location and/or status updates, e.g., via the software application, and thereby allow the master controller device to track, e.g., real-time, the movements and/or health and/or environmental conditions of the person or animal or object wearing or otherwise associated with the geolocation device. Particularly, by activating the tracking and/or monitoring application, the tracker will monitor the movement and conditions of the geolocation device and begin sending continuous updates (e.g., at about 1, or 2, or 5, or 10, or 15, or 30, or 45 updates in a given period, such as seconds, minutes, hours, and/or days) on the bands position, speed, activity, and/or status, e.g., health, of the user.

Particularly, in various embodiments, the master control, e.g., control, device and/or the geolocation and status monitoring device may include a display screen or other mechanism for presenting a user interface on the device. In such instances, the user interface may be a simple push and hold tracking/monitoring button, or it may be a virtual representation of a button such as on a touch screen or other surface of the device. In this instance, to get continuous updates, the "button" simply needs to be activated, so as to give X seconds of continuous tracking and/or monitoring, where X may be measured in seconds, minutes, and/or hours, so as to enable the best possible tracking when needed, without using battery or other resources when not needed.

Figure 7:
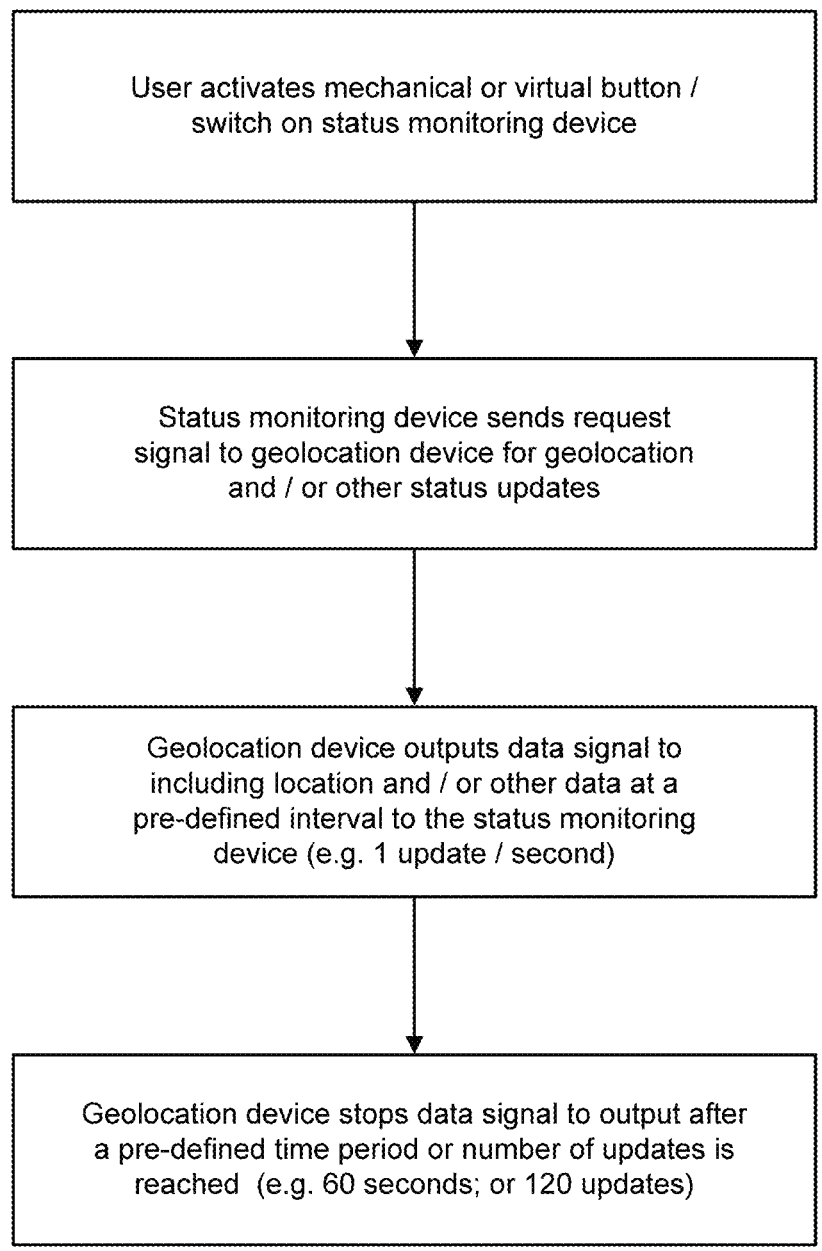
FIG. 7 presents a flow diagram for enacting a data transfer between the identity, geolocation, and/or health status monitoring apparatus and a control device of the system.

Accordingly, as can be seen with respect to FIG. 7, the method may include providing a geolocation, environmental, and/or health monitoring device, as herein described, that is configured for generating geolocation, environmental, and/or health status data, such as location and/or health information, of a person, animal, or object associated with the device. A master controller for pairing with the geolocation device may also be provided, such as where the master controller device may be a health status monitoring device and the like. Particularly, the geolocation and/or status monitoring device, as well as the master control device, may include compatible wireless communications modules, such as a communications module coupled to a touch-sensitive display or mechanical button or other switch for receiving a haptic contact and/or movement by a user.

Hence, when a first user of a requesting device that is paired with the geolocation device desires information from the geolocation device, the user may perform a haptic gesture. In certain instances, the requesting device may be a mobile computing device that may be configured so as to function as a master controller. Further, in various embodiments, the master controller may be a status monitoring device, which may be configured for being activated, such as by a haptic gesture. The haptic gesture may simply be a movement in a predetermined configuration or may be a gesture that effectuates the manipulation of a mechanical button or switch, or a representation thereof of the device, so as to activate the button or switch and thereby send the request for information to the geolocation and/or status monitoring device so as to signal the geolocation device for location and/or other status updates.

Likewise, upon receipt of the request, and if required upon authorization thereof, the geolocation device may output a data signal including the requested location and/or other environmental and/or health status information, such as at a predefined time, interval, and/or for a predetermined length of time. Particularly, in various embodiments, the controlling status monitoring device may be configured to receive a haptic contact signal, from a user, where the haptic signal is indicative of a gesture applied to the device, such as to a touch-sensitive display, to signal the request for a first amount of information for a pre-determined time period.

In response to the haptic gesture, the controlling device may then transmit a first wireless signal from the controlling status monitoring device to the geolocation device in response to the haptic contact, thereby requesting the geolocation device to transmit geolocation data to the status monitoring device, such as at a pre-determined time interval and for a pre-determined time period. In response thereto, the geolocation and/or health status monitoring device may then output a second wireless data signal containing the requested information back to the status monitoring device, e.g., in response to the first wireless signal, such as where the second wireless signal may include location, environmental, and/or health status information of the geolocation device, wherein the wireless signal is transmitted in accordance at the predetermined time and/or with the pre-determined time interval. Once the geolocation device has sent the second signal at the designated time and/or for the determined time period, the geolocation device may then cease to transmit the wireless signal from the geolocation device to the status monitoring device, e.g., when the pre-determined time period ends.

Figure 8:
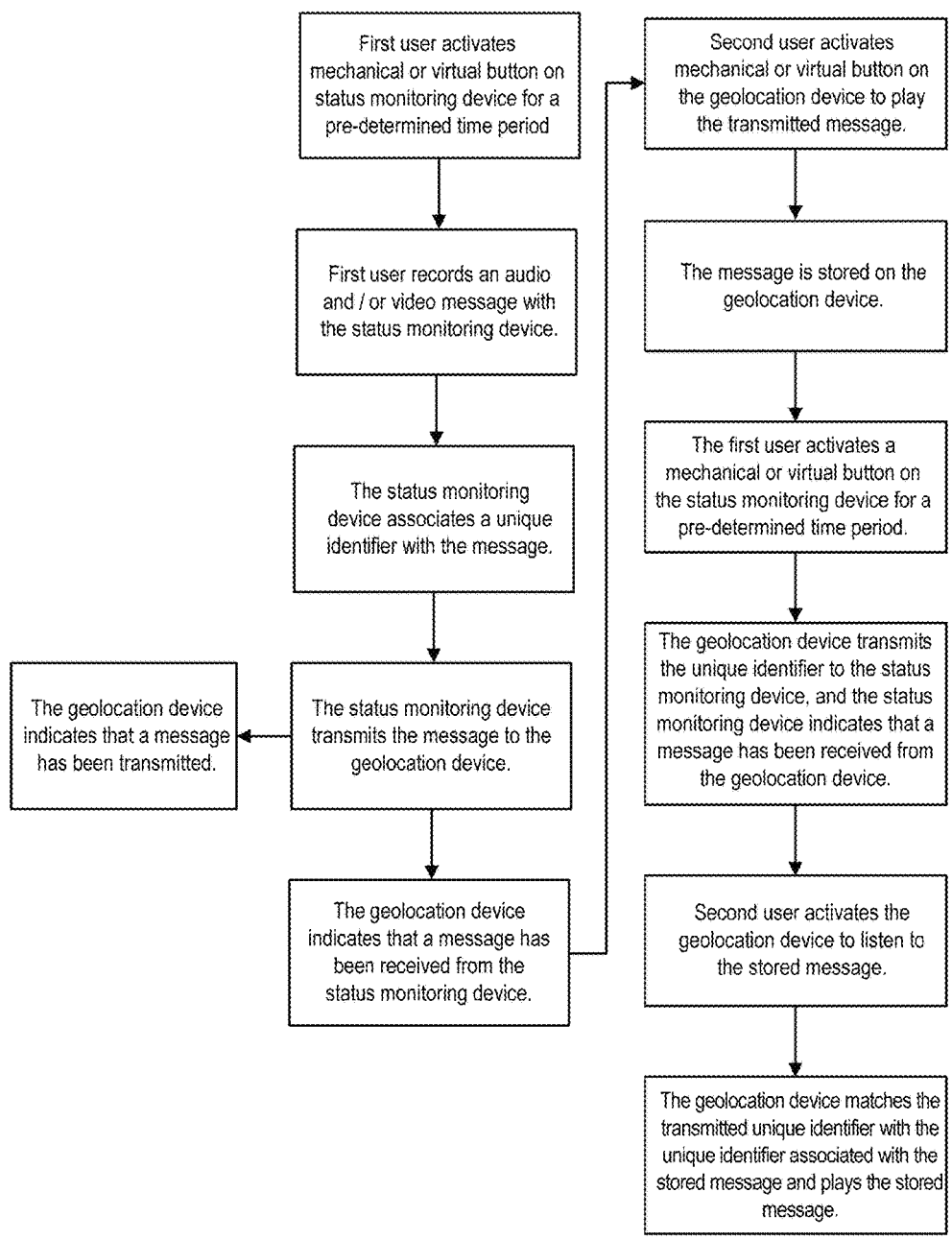
FIG. 8 presents a flow diagram for enacting a first communications protocol between devices of the system, such as be the transmitting of recorded messages.
Figure 9:
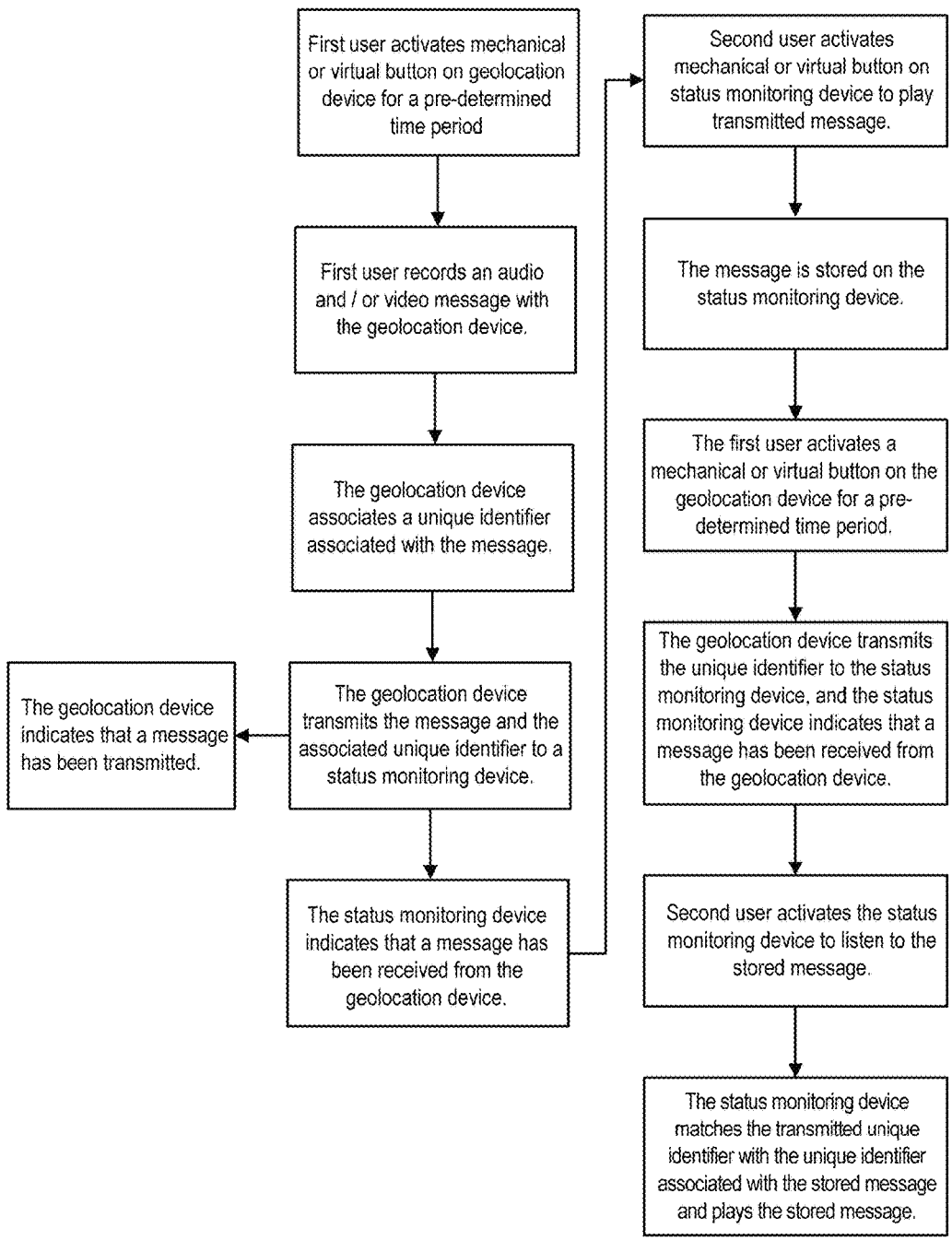
FIG. 9 presents a flow diagram enacting a second communications protocol between devices of the system.

Further, in various embodiments, as set forth in FIGS. 8 and 9, a method for transmitting messages between, e.g., to and/or from, a master control device and a paired geolocation device worn by a person is provided. For instance, in various embodiments, one or both of the control and/or the geolocation device may include a communications module that may include a camera, video camera, microphone, and/or a speaker, and/or may include a screen or other surface that is capable of displaying a sent and/or a received message. The message may be received and encoded in such a manner that it may be configured for being sent remotely from one device to the other. In various embodiments, the geolocation, environmental, and/or health status monitoring devices may include a geolocation receiver unit, e.g., GPS receiver, for receiving signals from a location signal emitter, e.g., global position satellite or beacon, so as to generate the geolocation data.

For example, a first user, e.g., of the master controller device or geolocation device, may activate the device, such as via manipulating one or more real or virtual buttons or switches, such as via a haptic gesture, and either speak or type a message to be recorded and/or encoded, e.g., digitally coded, by the device. The message, therefore, may be a spoken, e.g., audio message, and/or a video and/or a text message, and may be configured for being transmitted. Consequently, in various instances, the method for transmitting messages may include generating a unique identifier, e.g., by the controlling monitoring device or the geolocation device, and associating the unique identifier with the recorded and/or encoded message, which message may then be stored on the control status monitoring and/or geolocation devices, e.g., prior to transmission.

Once recorded and/or encoded and/or stored, the message and/or unique identifier may be transmitted wirelessly from one device, e.g., a master status controlling device, to the other, e.g., a geolocation, environmental, and/or status monitoring device. When received, the receiving device may then indicate, e.g., via an indicator such as an alarm, that a message has been received from the other, e.g., paired, device. Likewise, the transmitting device may indicate that the message has been sent, received, and/or listened to or read by the receiving device. Further, the receiving device may automatically display and/or play the message, or it may be stored on the receiving device upon receipt, available to be played or displayed upon authorization and/or activation. For instance, the method may include the receiving of the unique identifier separately and/or concurrently from the message and storing of the transmitted message and/or the unique identifier on the receiving device in a manner that the transmitted message is able to be reproduced on the speaker or a display of the receiving device, such as when a touch-sensitive real or virtual button is activated on the device.

Hence, once received an indicator may be activated on the receiving device to communicate to a user that a message is available for playback. Thus, when desired, the device user may then enter an authorization code or otherwise activate the playing and/or displaying of the message. Particularly, the user may activate the playing and/or displaying of the message such as by performing a mechanical and/or haptic gesture so as to actuate a mechanical and/or virtual button or switch. Where authorization and/or a unique identifier has been included with the message, the authorization and/or unique identifier may then be determined to be correct, e.g., the unique identifier transmitted matches the unique identifier associated with the stored message and/or the device and/or security code entered, then the message may be played and/or otherwise displayed. Particularly, the method may include reproducing the stored message on the speaker and/or display of the receiving device, such as when a touch-sensitive button is activated on the device. In certain instance, prior to reproduction, the unique identifier transmitted from the transmitting device to the receiving device will be compared to the unique identifier encoded with the message, and/or otherwise present on the receiving device, and if the identifiers match then the message will be played, displayed, or otherwise made available.

Specifically, with respect to FIG. 8, in one use model, a method for using a system of the disclosure for transmitting messages between a status monitoring device and a geolocation device is provided. For instance, in various instances, a method to provide simple and secure voice messaging between the tracking device, e.g., a guardian(s) mobile computing device running the tracking application, and the tracked device, e.g. a geolocation device as disclosed herein. In such an instance, the guardian, e.g., using the tracking device, can access and use a downloaded tracking application to record a short voice or video message that is to be sent to one or more selected tracking device(s), such as a compressed data file, which message may be played or shown on the speaker or a display configuration of the device. Likewise, upon receipt of the message, the child wearing the tracked device can then press a button or interact with a display of the device so as to activate and/or play the message. In particular instances, the system components can be configured such that the child's tracked device may signal the guardian's tracking device that the child pressed the activator to play the message.

Further, in various instances, the guardian can also select a recently sent message so as to have it reactivated or sent again or may select from a menu of pre-recorded messages and thereby have it played again on the child's tracked device without sending the compressed file again. Likewise, in a similar configuration, the child can press and hold the button, or activate a display screen and/or microphone, on the device to record a short message that can be sent to guardian(s) device, in like manner, as a compressed data file. In such instances, the application of guardian's device will then indicate and/or play the message from the child. In particular instances, all messages may be stored in the cloud, and will be available to guardian(s) and/or children for playing, downloading, sharing with friends, or posting to social media sites.

Accordingly, the method may include providing a geolocation device, e.g., having a speaker and/or a touch-screen or other display, that is further configured for being able to receive an input of a message or other such data. In various embodiments, the message may be a recorded message or video or may be a text message, such as entered via a keyboard or virtual keyboard. In certain embodiments, once input the message may be associated with a unique identifier that is configured for authenticating the veracity of the message and its source. Once recorded and/or associated with an authentication code, e.g., unique identifier, the message may be transmitted wirelessly, such as from the controlling device to the geolocation device. Once the message and/or unique identifier is received, the geolocation device may either immediately present the message or store the recorded message and the unique identifier on the geolocation device. Where the recorded message is stored, the device is able to reproduce the message on demand and present it on the speaker or display of the geolocation device, such as when a button is activated on the geolocation device.

With respect to transmitting the message wirelessly from the tracking status monitoring device to the tracked and/or monitored geolocation device, the signal may include both the message and/or a unique identifier, for identifying the sender of the message and the device to which it is sent. Hence, once the message and/or unique identifier is received, the receiving device, e.g., geolocation device, may indicate that a message has been received, is available for playback, and may need to be authorized and/or a "button" activated before the message is presented at the geolocation device. Specifically, in various embodiments, the unique identifier may be transmitted from the sending device, e.g., the status monitoring device, and may be compared to the unique identifier on the receiving device and/or associated with the received message so as to determine that it matches the unique identifier, e.g., associated with the stored recorded message on the geolocation device. Accordingly, once indicated and/or authenticated on the receiving, e.g., geolocation, device the stored recorded message may be reproduced on the display and/or speaker of the geolocation device when the device, e.g., button, is activated, that is if the unique identifier transmitted from the status monitoring device matches the unique identifier of the stored recorded message and/or the unique identifier of the device itself.

Likewise, with respect to FIG. 9, in another use model, a method for transmitting messages between a tracked geolocation device and a tracking status monitoring device may be provided. In such an instance, the method may include providing a geolocation device and associating a unique identifier with a recorded message on the geolocation device. Once a message is recorded, e.g., by the geolocation device, and/or a unique identifier associated therewith, the recorded message and/or the unique identifier may be wirelessly transmitted to the controlling, e.g., status monitoring, device either separately and/or together. Once received the recorded message and/or the unique identifier may be stored on the status monitoring device. As such, the recorded message may be able to be reproduced on a speaker or display of the tracking status monitoring device, such as when a mechanical or virtual button is activated on the status monitoring device.

Particularly, in either instance, the transmitting may involve the sending of a signal wirelessly from the geolocation device to the status monitoring device, such as where the signal includes one or both of the message and/or unique identifier. Once received by the controlling status monitoring device an indicator and/or alarm on the status monitoring device may be activated, such as where the indicator and/or alarm communicates to a user that a recorded message is available for playback. Additionally, in various embodiments, to ensure the security of the transmission, a unique identifier may be transmitted from the geolocation device, and it may then be determined if the unique identifier associated with the message is the same as the unique identifier sent separately from the sending device to the receiving device and/or associated with the receiving device itself. If the unique identifier associated with the stored recorded message and/or on the tracking status monitoring device matches, then the stored recorded message may be reproduced on the speaker and/or display of the status monitoring device, e.g., when a mechanical or virtual button is activated on the status monitoring device, such as if the unique identifier transmitted from the geolocation device matches the unique identifier of the stored recorded message and/or status monitoring device itself.

In various instances, the messages may take the form of reminders, and/or one or both the status monitoring controlling and/or the geolocation devices may include a calendaring functionality that can be updated by the interaction of one device with the other in accordance with the methods herein disclosed so as to update the calendaring functionality. For instance, in various instances, a method for setting a reminder is provided, such as for allowing a master controlling device to set up a reminder for a person wearing the geolocation device, or vice versa. Specifically, once paired, one or more of the devices may include a calendaring function that is accessible by the other device, such that the one device may set up tasks and/or reminders on the other device and/or set alarms for reminding the user of the set up tasks. For example, in one embodiment, a method for allowing a guardian, having a master controlling device, to access a geolocation device, of a child, so as to setup events for child and/or to set up alarms so as to remind the child of the set up events.

In such an instance, each event may be recorded and/or played as an audio prompt from the geolocation device. Various sound and/or tactile effects can also be used. In certain instances, when setting up such a calendared event and/or a reminder of the same, guardians can record either an individualized audio prompt, or can select one or more from a set of pre-recorded messages, such as from a menu of options. Such actions can take place using an "app," or other software, set up on the paired master controller and/or geolocation device. Any particular event and/or reminder may be set up, such as wakeup alarms, school bus alarms, bed time alarms, class or school event alarms, and the like. These events and/or alarms may be setup and managed via the master controlling device being paired with the geolocation device, such as by using compatible applications, e.g., a mobile/phone application.

Additionally, in various instances, a method for event based location sharing is provided. For instance, one or more devices of the disclosure may include programming and/or otherwise be configured so as to allow one or more persons and/or groups of people to share their locations with one another, either collectively or individually, for a prolonged or short period of time, such as for a pre-defined time and/or event, such as for a meeting, for a meal, or any type of gathering. In such an instance, the event will typically have a location and time period associated with the particular event. Such events may also be recurring, scheduled events. In particular embodiments, the invitees and/or attendants selected for event updates may be from a list of potential attendees, or may be those who have opted in, such that once a member of the group has opted into the event, then their location can be shared with all the other members of the group who have opted in, e.g., for the set time for the set event. Optional periods of time reminders and other messaging and/or updating may be provided for before and/or after the event. Additionally, once the event has started, continuous updates may be sent out to group members so as to allow other group members to know who has already arrived at the event location, and who may be late to the event. Also, group members may message one another reminders or any changes in timing or location.

Accordingly, in an exemplary use model, using a suitably configured device of the disclosure a user could setup a meeting at a restaurant at a given time on a particular day, and then send invites to a group of friends or associates who would then be invited. All of the recipients that accept the meeting, e.g., receive an invite message and respond affirmatively to opt in, will be added to the meeting and would thereby will be pushed notifications, messages, and updates from the other group members and/or about the meeting, and would also thereby allow themselves to be tracked by other meeting attendee's and/or to track other meeting attendees prior to and/or after the meeting. For instance, at some designated time period prior to the meeting, e.g., 3 or 2, or 1 hour or less prior to the meeting, any meeting attendee using the app, e.g., who has accepted the invite and/or opted in can view the meeting in the application and/or see the current location of all of the meeting attendees, and/or send messages to a specific attendee or all the attendees. This may continue to up to 1 or 2 or 3 or more hours post meeting, or in some instances, after the meeting, the attendees may no longer be able to view the other attendee's locations and/or send messages or updates.

Further provided herein is a new way of sharing and/or showing location information. For instance, in a basic use model, a tracking application of the disclosure can be configured so as to determine and/or show and/or provide location information, such as for one or more users of the system on a map, which map may include one or more indicators for display on the map so as to indicate the position and/or location of each person, animal, object, or a given asset's location. In another embodiment, a method of showing, sharing, or otherwise providing event and/or location information for events, such as where in addition to or instead of showing locations on a map, a grid of time and distance, e.g., for all tracked persons, animals, and/or items may be provided. Particularly, the place and/or time could be a set of coordinates and/or an estimated time of arrival and/or the distance from the event. In such an instance, if a display is provided, the display can be color and/or greyscale coded to quickly indicate who will be early, who has already arrived, who should arrive on time, who might be slightly late, those who will be very late, and/or the like.

Additionally, in another aspect, in various instances the wearable device may be configured for sharing location and/or health monitoring information, in other instances, the wearable device may be configured for streaming music. Particularly, in various instances, the device and system may be configured for tracking and/or monitoring and/or receiving music data, such as in a streaming format. For instance, employing the communications module of the device, a user may connect with a central server, from which server one or more music applications may be downloaded and consequently uploaded onto the device or to a database of the system. For example, the device may be preconfigured with or otherwise be configured for downloading a music streaming application, which downloadable application, or "app", may present a portal through which the device may be connectable to a music based web-server.

The music based web server may be configured as a music delivery service. The music delivery service may be configured for selecting and transmitting music, in the form of one or more data packets, which when received by the device may be compiled and/or listened to by the user via one or more associated speakers and/or headphones, such as wireless, Bluetooth headphones. The music data may be transmitted via the app to the monitoring and/or tracking device as discrete packets, or may be transmitted in a streaming fashion. For example, the streaming music based app may present a user interface, if the device includes a display screen, and/or may simply be configured to be activated and/or controlled by voice command. Additionally, in particular embodiments, the streaming music app may be configured for adapting the monitoring and/or tracking device for being activated by voice commands.

Once activated, the device, through the app, may be configured for receiving the transmitted music, such as in streaming fashion, so as to enable the device to play music. As such, in particular instances, the music based web server transmits music to the device by using a streaming technology, which may send songs collectively or in sequence one by one for a predetermined time. In various embodiments, once the user identifies and/or selects music based on his/her preferences, the streaming music server may then retrieve the selected music, or other music the server programming determines to be appropriately associated with the same, from a database, and then transmits that data, via the communications module, to the remote tracking and/or monitoring device for listening.

Figure 10:
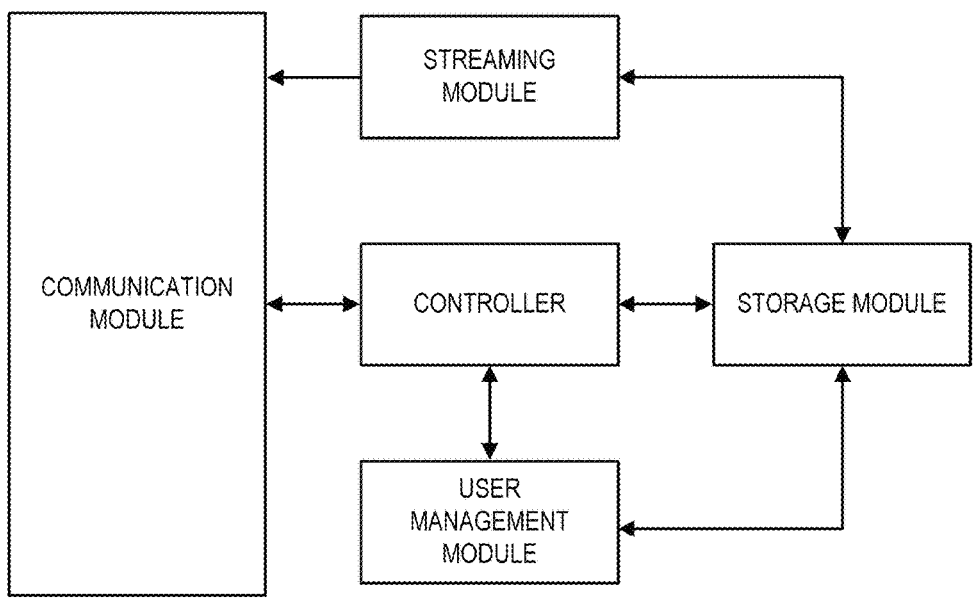
FIG. 10 presents a system diagram for another embodiment of a system of the disclosure, such as for the transmission and/or streaming of data, such as music, video, or other such information.

Particularly, as depicted at FIG. 10, the streaming music system may include an external server, which remote server may include or otherwise be associated with a controller, a streaming module, a storage module, a user management module, and/or a communication module all of which may be associated with the wearable device, such as via an appropriate transmitter and/or receiver and antenna. The controller, therefore, may be configured to control the streaming operations of the wearable device and/or an associated music streaming or downloading server. For instance, the controller may be configured to control the exchange of data and other information between the device and the server, such as over a network, such as an internet or cellular network. For example, the controller may control the streaming module to provide the downloadable and/or streaming music to one or more users who requests music be streamed through the communication module of the wearable device.

Under the control of the controller, the streaming module streams the music content to the corresponding requesting device or devices, if coupled, paired, and/or otherwise synced thereof. When two or more coupled or synced devices request to receive the same music stream, the server and/or streaming module may then stream the same music content to a second device as the music content streamed to a first device. In so doing, the streaming module streams the music content to the two or more requesting devices separately.

The storage module may store one or more music files, such as music files that have been uploaded and/or downloaded, e.g., from the server, user preferences, and/or control parameters and/or control programming so as to control the operations of the server, and a data storage for storing data generated in the program execution. For example, the storage module may store the music content for playing and/or streaming, and user identification, and/or authorization information for the streaming service and/or other social network data. The user management module, in this instance, may be configured to determine whether device and/or user registers requesting communication with one another and/or the music system are authorized to so communicate and/or for streaming music to be played, such as by considering registration information stored to the storage module.

Once authorization is confirmed, the controller prompts the activation of the communication and/or streaming music system allow data transfer between the devices and system components, such as for communication and/or streaming purposes. Hence, the communication module will then effectuate the transmission and receipt of signals to and from user devices, such as over any suitable networked system, such as via cellular, WIFI, internet, radio frequency, and the like. In various instances, the central server may include, or may otherwise be associated with, the streaming module, which may be integral to the wearable device, for streaming the music content thereto. Also, the streaming module may be included in a transmission module for transmitting the content. More Particularly, the system may include a central server, which central server is configured for associating a streaming music system with the monitoring and/or tracking device of the system.

As such, the system may include a remote music system, which music system may include a music server, having a controller for directing the operations of the server, such as with respect to receiving a user preference from a user, generating a play list based on the user preferences, pulling the music data files associated with the generated play list from a database, compiling and packaging the music files for transmission by a server side communications module, and transmitting the music to one or more monitoring and/or tracking devices, such as through the central server or directly to the device, e.g., a device side communications module, for playing thereby. For instance, as can be seen with respect to FIG. 10, the music system may include a storage module, a streaming music module, a user management module, and/or a control module, such as a microprocessor configured for controlling the interactions between the user device and the streaming music system.

Accordingly, the music system may include a streaming music module that is configured for transferring one or more music files, such as by effectuating one or more streaming music protocols, and consequently the system may include a storage module, including a memory and/or a memory cache, for storing the downloadable and/or streaming music files. The system may also include a user management module that is configured for eliciting and storing user preferences, such as via an automated interview, configuring user profiles, determining user play lists, e.g., based on determined user preferences, and/or generating various connections between users based on user interactions with the system. In various instances, user preferences may be configured using voice commands, in response to an audible menu of options, or may be configured by accessing a user account online at a user interface at a client computer, which configurations may then be applied to the monitoring and/or tracking device, such as through a wired, e.g., USB, or wireless connection.

In particular embodiments, a method for sharing user preferences and/or music content, and/or other data may be provided such as through a music service, for instance, based on connection to a social network and/or between members of the social network. Particularly, in various instances, the monitoring and/or tracking device may be connectable to one or more social media network systems, such as for sharing tracking information, status data, and/or various content related data, e.g., likes and dislikes, music preferences, SMS or text messages, or even music and/or video or digital photo content, and the like. Such data may be transmitted over a network, such as a cellular network, WIFI, BLUETOOTH®, or other wireless or wired connection.

More particularly, in such instances, as disclosed above, the device may be configured for connecting to and communicating through a transceiver, such as via one or more of LTE cellular connectivity, GPS, WIFI, BLUETOOTH®, and the like, such as for both activity tracking and music downloading and streaming. Specifically, the device may include a SIM card and/or may be configured to share a phone number with a synced cellular telephone, and consequently may have a telephone number, for receiving and placing calls, such as via voice command, and may have connectivity via a cellular telephone service such as T-MOBILE'S DIGITS®, AT&T NUMBERSYNC®, VERIZON®, SPRINT®, and the like. Likewise, the device may be able to connect to one or more streaming music services, such as SPOTIFY®, PANDORA®, and the like.

As such the device may have a narrow or wide as well as a high bandwidth so as to stream high quality audio, and in some instances, video. For instance, the bandwidth may range from about 100 kbps to about 125 or 250 or about 500 or even 1000 kps or more, so as to ensure smooth and reliable playback. Likewise, in such instances, the processor and memory may be configured for encoding and/or decoding high quality streaming audio, and in some instances video. And in some instances, the GPS and activity tracking and/or monitoring, so as to provide precise activity and/or sports tracking and/or monitoring.

In various embodiments, the BLUETOOTH® capability may be configured such as to allow audio control to provide connectivity to any standard wireless Bluetooth headset and/or microphone, such as for making calls and listening to music. Likewise, received text messages can be converted to audio for playback, and in other instances, may be connectable with other communication apps such as WHATSAPP®, FACEBOOK MESSENGER®, and the Like®. The tracking and monitoring device may also be connectable to various digital assistants, such as those powered by GOOGLE®, AMAZON®, and the like, such as for answering questions that the wearer of the device, such as a child, may have and ask. Through one or more of these connectivities a mapping app may be accessed such as through verbal command so as to receive audio directions. Hence, in various embodiments, the health monitoring and/or tracking device may be configured for not only tracking an individual, but for monitoring the health status thereof, as well as for streaming music to the device.

Accordingly, when a user of the tracking and/or health monitoring device desires to listen to music, an activation sequence may be initiated, such as by triggering a button or making a voice command, so as to thereby activate the streaming music system, such as via a downloadable application, which application once activated, the components of the device, e.g., communications module, may connected to and access the streaming service to enable the streaming of data, e.g., music data, from the service to the device. In this instance, a remote central network server may function as an exchange for data and information between the device and the streaming music server, and/or the device may connect directly with the streaming music server, such as through a downloadable app of the device, whereby music may then be downloaded and/or streamed to the device.

Hence, once activated the server may then stream the music content requested by the device to the tracking and/or monitoring device for the playing thereof. Status and/or preference and/or other information may also be exchanged between the device and server, e.g., music or other authorized server, in this manner. In various instances, a plurality of the tracking and/or monitoring devices, as well as one or more master control devices may be paired and/or otherwise synced in such a manner that the streaming music and/or other transmittable data may be shared together.

For instance, in such an instance, the streaming music may be played simultaneously on the linked device, such as in a synced fashion, so that two or more users, such as two users each having a separate but synced tracking device may listen to the music, or other data, together, even though they are located remotely from one another. Additionally, voice or text messages may be sent to synced devices, such as through cellular, WIFI, Bluetooth, and/or RF transmission. In various instances, any audio, visual, or audiovisual content can be downloaded or streamed to these portable electronic devices. As indicated above, the tracking and/or health monitoring device may be configured so as to be tracked and/or monitored across one or more regions, such as across a multiplicity of regions. These regions may, in turn, be covered by one or more cellular towers, internet service providers, WIFI or BLUETOOTH®, connections, radio frequency transmitters, and the like.

For example, a cellular, internet, and/or RF network may be used to transmit and receive various communication and/or media content to a tracking and/or monitoring device. As such, a plurality of transceivers may be provided and/or linked across one or more regions so as to be in communication with one another, such as via a central server that acts as a communication and/or content source. Such transceivers may each be associated with a certain geographic region or "cell," where together all the cells within a given region may make up a service area. Hence, the tracking and/or monitoring device(s) may travel within a first service area or cell, but then may cross from one geographic region into another and another and another, during the course of a tracking and/or monitoring event and/or communication transmission.

Consequently, one or more transceivers may be provided so as allow the device to be tracked and/or monitored, and/or music to be streamed over remote distances to the device(s) across a wide range of regions, while the device may be switched from one transceiver to another corresponding to the geographic region occupied by the portable electronic device at any given time. In this way, continuity of content stream and/or music playback may be provided through the various geographical regions to the portable electronic device. In various embodiments, the paired and/or master control device, such as the device monitoring the tracking device, may be tracked and/or monitored throughout one or more regions and/or may stream music in like manner, such as while remaining in communication with the portable electronic monitoring and/or tracking device as either device moves between the various geographic regions of the service area(s).

Further still, also provided herein are auxiliary devices and/or methods that may be used in conjunction with the geolocation tracking and/or status monitoring devices disclosed herein. For example, in one use model, a device and/or method for tracking a human or animal is provided. For instance, where tracking a human is provided, the geolocation device may be associated with a watch style wristband or a necklace, such as where the band or necklace includes a power reserve, e.g., a battery unit or one or more other fuel cells, that is configured for charging the geolocation and/or health status monitoring device. For instance, the battery may be configured with a number of fuel cells in a compact package that is specially configured so as to provide 3, or 4, or 5, or 7, or 10 days or more of battery life.

Likewise, when tracking an animal, such as a dog, the geolocation device may be associated with a collar and/or leash such as where the collar and/or leash includes a power reserve, e.g., a battery unit, that is configured for charging the geolocation and/or health status monitoring device. Such charging may be conducted through a wired or wireless connection, such as through induction and/or other wireless charging modality, such as A4WP, Qi, and the like. Particularly, in various instances, the wristband, necklace, and/or leash may include one or more fuel cells that are coupled to a charge port via one or more wires, such as where the device housing may be reinforced so as to prevent stress from being exerted on the wires, chargeports, and/or other associated charging apparatus, e.g., fuel cells.

More particularly, the wristband, necklace, leash, and/or other like attachment unit functions for its intended purposes, as well a power reserve capable of supplying a charge to the geolocation tracking unit. For instance, where a charging instrument is provided, such as configured as a leash, the leash will function as a normal, e.g., retractable, pet leash, but while connected or otherwise associated to the pet's collar will provide power for charging any rechargeable geolocation device on the pet's collar. Specifically, the charging device may be configured for being retained within the leash and/or collar and may include charging ports, surfaces, transmitters, or other charging connections for the geolocation devices, and optionally a standard USB, e.g., Type A, connector may be provided so as to also charge other devices.

Hence, the leash, or other suitably configured associated element, such as the wristband, or necklace, or the like may be configured so as to allow owners to charge associated geolocation and/or device(s) on the person's or pet's charge reserve, e.g., collar, where the tracking or other device can be charged just by its association with the reserve, e.g., collar/leash, such as by just giving the pet a short walk everyday on the leash. Particularly, the system can be configured such that by connecting the leash to the pet's collar the charging of any compatible device on the pet's collar may be started. Of course, an additional charging can take place such as by plugging the device in to a typical charging outlet, such as via the charger provided. The battery, rechargeable battery, and/or fuel cells may be replaced as needed.

In various instances, the leash or other element may include a light, such as a flash light element. Likewise, the leash or other element may include a Bluetooth, e.g., Low Energy Bluetooth, tracking functionality, such as with an audible alarm so as to allow easy locating of the leash, collar, or other element from a master controller, e.g., smart phone. The leash and/or collar may also include a waste bag dispenser. In certain instances, the leash and/or collar may have a secure connector to the pet's collar that provides a strong connection to the collar without putting stress on the power connection.

Some or all of the steps and operations associated with the techniques or methods introduced here may be performed by hardware components or may be embodied in non-transitory machine-executable instructions that cause one or more general purpose or special purpose computer processors programmed with the instructions to perform the steps. The machine-executable instructions may be stored on a computer-readable or machine-readable medium. The steps may be performed by a combination of hardware, software, and/or firmware. In some cases the machine-executable instructions may be downloaded from a server, from a website, and/or from an application store or an app store. For instance, the device, e.g., bracelet, firmware may be upgradeable, such as using a BLE connection to a computer, smartphone, or other network enabled device. In such an instance, the computer, smart phone, bracelet, or other network enabled device may communicate through a suitably configured app, such as a smart phone app for directing the operations of the bracelet.

While this disclosure contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods, apparatuses, devices, and systems are described herein in detail with reference to certain versions, it should be appreciated that other versions, methods of use, embodiments, and combinations thereof are also possible. Therefore the spirit and scope of the appended claims should not be limited to the description of the embodiments contained herein.

The phrases "in some embodiments," "according to some embodiments," "in the embodiments shown," "in other embodiments," "in some examples," "in some cases," "in some situations," "in some configurations," "in another configuration," and the like, generally mean that the particular feature, structure, or characteristic following the phrase is included in at least one embodiment of the present invention and/or may be included in more than one embodiment of the present embodiments. In addition, such phrases do not necessarily refer to the same embodiments or different embodiments.

The term "about" is used herein to refer to +/−10% of a given measurement, range, or dimension unless otherwise indicated.

The invention claimed is:

1. A wearable thin profile geolocation device for tracking and/or monitoring a human or pet within a geographical region, the geolocation device comprising:

a housing having an elongated body, the housing comprising: a first and a second elongated member, each of the first and second elongated members being defined by a respective first and second extended surface portion and a circumferential portion, the circumferential portion including a latching member, the latching members for allowing the first elongated member and the second elongated member to be coupled together to form the housing, the housing having a waterproof cavity in between the first and second extended surface portions of the first and second elongated members; and a semi-flexible digital logic circuit board arrangement contained within the cavity of the housing, the semi-flexible digital logic circuit board arrangement having one or more rigid circuit board portions connected by one or more flexible portions, the digital logic circuit board arrangement being positioned in the cavity of the housing, one or more of the rigid circuit board portions of the digital logic circuit board arrangement including a central processing unit (CPU) or graphics processing unit (GPU), a geolocating module, a communications module, a memory, and a battery, the CPU or GPU being operably connected to the geolocating module, the communications module, the memory and the battery, the CPU or GPU including an artificial intelligence (A/I) module, the A/I module configured for receiving a user command regarding the implementation of a function, interpreting the user command regarding the function, and directing the CPU or GPU to perform the commanded function, wherein the commanded function pertains to one or more of determining a location, a direction of travel, a health status, or an environmental condition of a person or pet wearing the geolocation device, and transmitting via the communications module the determined location, direction of travel, health status, and/or environmental condition to a computing device coupled via a wireless network to the geolocation device such that if the location, direction of travel, health status, and/or environmental condition is beyond a predetermined parameter, an alarm is set off in one or more of the geolocation device and the coupled computing device.

2. The wearable thin profile geolocation device according to claim 1, wherein the digital logic circuit board is curved or articulated.

3. The wearable thin profile geolocation device according to claim 2, wherein the first and second elongated members comprise one or more of a plastic, rubber, polypropylene, and a polycarbonate.

4. The wearable thin profile geolocation device according to claim 1, wherein when the first elongated member is coupled to the second elongated member to form the housing, the housing has a thickness, wherein the thickness ranges from 3 mm to 20 mm.

5. The wearable thin profile geolocation device according to claim 4, wherein the geolocating module comprises a GPS receiver.

6. The wearable thin profile geolocation device according to claim 5, wherein the communications module is configured for connecting to a cellular or internet network.

7. The wearable thin profile geolocation device according to claim 6, wherein the communications module comprises one or more of a radio frequency (RF) transmitter, a cellular transmitter, a SIM card, a WIFI, a Bluetooth transmitter, and a pairing device.

8. The wearable thin profile geolocation device according to claim 7, wherein the A/I module is configured for predicting one or more of the location, the direction of travel, the health status, or the environmental condition of the person or pet wearing the geolocation device.

9. The wearable thin profile geolocation device according to claim 8, wherein the predicting involves analyzing and compiling historical data, the historical data pertaining to one or more of previous location data, previous direction data, previous health data, and previous environmental data.

10. A wearable thin profile geolocation device for tracking and/or monitoring a human or pet within a geographical region and for playing music, the geolocation device comprising:
   a housing having an elongated body, the housing comprising: a first and a second elongated member, each of the first and second elongated members being defined by a respective first and second extended surface portion and a circumferential portion, the circumferential portion including a latching member, the latching members for allowing the first elongated member and the second elongated member to be coupled together to form the housing, the housing having a waterproof cavity in between the first and second extended surface portions of the first and second elongated members; and
   a semi-flexible digital logic circuit board arrangement contained within the cavity of the housing, the semi-flexible digital logic circuit board arrangement having one or more rigid circuit board portions connected by one or more flexible portions, the digital logic circuit board arrangement being positioned in the cavity of the housing, one or more of the rigid circuit board portions of the digital logic circuit board arrangement including a central processing unit (CPU) or graphics processing unit (GPU), a geolocating module, a communications module, a music module, a memory, and a battery, the CPU or GPU being operably connected to the geolocating module, the communications module, the music module, the memory and the battery, the CPU or GPU including an artificial intelligence (A/I) module, the A/I module configured for receiving a user command regarding the implementation of a music function, interpreting the user command regarding the function, and directing the music module to initiate or terminate the playing of music, wherein the initiating of the playing of music includes one or more of playing music stored in the memory or launching a streaming music application.

11. The wearable thin profile geolocation device according to claim 10, wherein the CPU or GPU is further configured for determining a location, a direction of travel, a health status, or an environmental condition of a person or pet wearing the geolocation device, and transmitting via the communications module the determined location, direction of travel, health status, and/or environmental condition to a computing device coupled via a wireless network to the geolocation device.

12. The wearable thin profile geolocation device according to claim 11, wherein if the location, direction or travel, health status, and/or environmental condition is beyond a predetermined parameter, an alarm is set off in one or more of the geolocation device and the coupled computing device.

13. The wearable thin profile geolocation device according to claim 12, wherein the initiating of the playing of music comprises the launching of the streaming music application, wherein the streaming music application is a downloadable app that has been installed on to the geolocation device.

14. The wearable thin profile geolocation device according to claim 13, wherein the launching of the streaming music application results in the communications module connecting to a remote streaming music service via a wireless cellular or internet connection for receiving musical transmissions therefrom.

15. The wearable thin profile geolocation device according to claim 14, wherein the music to be played comprises user selected music.

16. A wearable thin profile geolocation device for communicating and tracking and/or monitoring a person within a geographical region, the geolocation device comprising:
   a housing having an elongated body, the housing comprising: a first and a second elongated member, each of the first and second elongated members being defined by a respective first and second extended surface portion and a circumferential portion, the respective circumferential portions including latching members, the latching members for allowing the first elongated member and the second elongated member to be coupled together to form the housing, the housing having a waterproof cavity in between the first and second extended surface portions of the first and second elongated members; and
   a semi-flexible digital logic circuit board arrangement contained within the cavity of the housing, the semi-flexible digital logic circuit board arrangement having one or more rigid circuit board portions connected by one or more flexible portions, the digital logic circuit board arrangement being positioned in the cavity of the housing, one or more of the rigid circuit board portions of the digital logic circuit board arrangement including a central processing unit (CPU) or graphics processing unit (GPU), a geolocating module, a communications module, an artificial intelligence module, a memory, and a battery, the CPU or GPU being operably connected to the geolocating module, the communications module, the A/I module, the memory, and the battery, the A/I module being configured for receiving a user command regarding implementation of a communication operation, interpreting the user command regarding the communication operation, and initiating the communication operation, wherein the communication is directed to a computing device coupled via a wireless network to the geolocation device.

17. The wearable thin profile geolocation device according to claim 16, wherein the communications module comprises one or more of cellular or voice over internet (VOIP) communications capabilities, through which cellular or VOIP communications capabilities the communication operation is initiated and/or conducted.

18. The wearable thin profile geolocation device according to claim 17, wherein the cellular communications capabilities are effectuated through a SIM card.

19. The wearable thin profile geolocation device according to claim 16, wherein the A/I module is configured for determining a location, a direction of travel, a health status, or an environmental condition of the person being associated with the geolocation device.

20. The wearable thin profile geolocation device according to claim 19, wherein the communications module is further configured for transmitting one or more of the determined location, direction of travel, health status, and/or environmental condition to the computing device.

* * * * *